United States Patent
Horwitz et al.

(10) Patent No.: US 10,010,595 B2
(45) Date of Patent: Jul. 3, 2018

(54) LIVE RECOMBINANT BOOSTER VACCINE AGAINST TUBERCULOSIS

(71) Applicant: The Regents of the University of California, Oakland, CA (US)

(72) Inventors: Marcus A. Horwitz, Los Angeles, CA (US); Qingmei Jia, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 6 days.

(21) Appl. No.: 14/520,163

(22) Filed: Oct. 21, 2014

(65) Prior Publication Data

US 2015/0056242 A1  Feb. 26, 2015

Related U.S. Application Data

(62) Division of application No. 13/704,133, filed as application No. PCT/US2011/040550 on Jun. 15, 2011, now abandoned.

(60) Provisional application No. 61/355,052, filed on Jun. 15, 2010.

(51) Int. Cl.
| | | |
|---|---|---|
| *A61K 39/02* | (2006.01) |
| *C07K 14/35* | (2006.01) |
| *C07K 14/195* | (2006.01) |
| *A61K 39/04* | (2006.01) |
| *C12N 1/20* | (2006.01) |
| *C12N 1/36* | (2006.01) |
| *A61K 39/00* | (2006.01) |

(52) U.S. Cl.
CPC .............. *A61K 39/02* (2013.01); *A61K 39/04* (2013.01); *C07K 14/195* (2013.01); *C07K 14/35* (2013.01); *C12N 1/20* (2013.01); *C12N 1/36* (2013.01); *A61K 2039/522* (2013.01); *A61K 2039/523* (2013.01); *A61K 2039/545* (2013.01); *A61K 2039/5555* (2013.01); *A61K 2039/55566* (2013.01); *A61K 2039/6037* (2013.01); *C07K 2319/40* (2013.01)

(58) Field of Classification Search
None
See application file for complete search history.

(56) References Cited

U.S. PATENT DOCUMENTS

| | | | |
|---|---|---|---|
| 6,471,967 B1 * | 10/2002 | Horwitz ................. | A61K 39/04 424/184.1 |
| 7,026,465 B2 | 4/2006 | Skeiky et al. | |
| 2004/0197343 A1 | 10/2004 | Dubensky, Jr. et al. | |
| 2005/0281841 A1 | 12/2005 | Kopecko et al. | |
| 2009/0263418 A1 | 10/2009 | Speelman-Van Der Wel et al. | |

OTHER PUBLICATIONS

Brockstedt et al., "Listeria-based cancer vaccines that segregate immunogenicity from toxicity". PNAS, vol. 101, No. 38, Sep. 21, 2004, pp. 13832-13837.
Yan et al., "Selected prfA* Mutations in Recombinant Attenuated Listeria monocytogenes Strains Augment Expression of Foreign Immunogens and Enhance Vaccine-Elicited Humoral and Cellular Immune Responses". Infection and Immunity, vol. 76, No. 8, Aug. 2008, pp. 3439-3450.
International Search Report and Written Opinion of the International Searching Authority for International Application No. PCT/US2011/040550 dated Apr. 6, 2012.

\* cited by examiner

*Primary Examiner* — Robert A Zeman
(74) *Attorney, Agent, or Firm* — Gates & Cooper LLP

(57) ABSTRACT

Embodiments of the invention comprise an improved vaccine for generating an immune response and preventing or treating mycobacterial diseases such as *tuberculosis* in humans and animals. Embodiments of the invention also comprise a method for using the vaccine against such mycobacterial diseases.

20 Claims, 9 Drawing Sheets iMFI of cytokine-producing r30 specific CD4+ T cells (TBm010)

iMFI of cytokine-producing 30p specific CD4+ T cells (TBm010)

LIVE RECOMBINANT BOOSTER VACCINE AGAINST TUBERCULOSIS

CROSS REFERENCE TO RELATED APPLICATIONS

This application is a divisional application that claims the benefit under 35 U.S.C. § 120 of now abandoned U.S. patent application Ser. No. 13/704,133, filed Dec. 13, 2012 which claims priority under Section 119(e) from U.S. Provisional Application Ser. No. 61/355,052, filed Jun. 15, 2010, the entire contents of which are incorporated herein by reference.

STATEMENT OF GOVERNMENT SUPPORT

This invention was made with Government support under AI031338, awarded by the National Institutes of Health. The Government has certain rights in the invention.

1. Field of the Invention

The present invention relates to methods and compositions of matter that are useful for preventing or reducing the possibility of infection caused by Mycobacterium tuberculosis, the agent of tuberculosis, and infection by other pathogenic strains of mycobacteria in humans and/or animals including Mycobacterium bovis and Mycobacterium leprae.

2. Background

Around the world, intracellular bacteria are responsible for millions of deaths each year and untold suffering. Tuberculosis, caused by Mycobacterium tuberculosis, is a leading worldwide cause of death from an infectious disease, with millions of new cases and deaths reported each year. Initial infections of M. tuberculosis almost always occur through the inhalation of aerosolized particles as the pathogen can remain viable for weeks or months in moist or dry sputum. Although the primary site of the infection is in the lungs, the organism can also cause infection of the bones, spleen, meninges, and skin. Depending on the virulence of the particular strain and the resistance of the host, the infection and corresponding damage to the tissue may be minor or extensive.

While M. tuberculosis is a significant pathogen, other species of the genus Mycobacterium also cause disease in humans and animals and are clearly within the scope of the present invention. For example, M. bovis is closely related to M. tuberculosis and is responsible for tubercular infections in domestic animals such as cattle, pigs, sheep, horses, dogs and cats. Further, M. bovis may infect humans via the intestinal tract, typically from the ingestion of raw milk. The localized intestinal infection eventually spreads to the respiratory tract and is followed shortly by the classic symptoms of tuberculosis. Another important pathogenic vector of the genus Mycobacterium is M. leprae which causes millions of cases of the ancient disease leprosy. Currently, there is no effective vaccine to prevent it. A vaccine to prevent leprosy would potentially have widespread use in endemic areas such as India and Brazil. Other species of this genus which cause disease in animals and humans include M. kansasii, M. avium intracellulare, M. fortuitum, M. marinum, M. chelonei, M. africanum, M. ulcerans, M. microti, and M. scrofulaceum. The pathogenic mycobacterial species frequently exhibit a high degree of homology in their respective DNA and corresponding protein sequences and some species, such as M. tuberculosis and M. bovis are highly related.

With regard to alveolar or pulmonary infections by M. tuberculosis, the guinea pig model closely resembles the human pathology of the disease in many respects. Accordingly, it is well understood by those skilled in the art that it is appropriate to extrapolate the guinea pig model of this disease to humans and other mammals. As with humans, guinea pigs are susceptible to tubercular infection with low doses of the aerosolized human pathogen M. tuberculosis. Unlike humans where the initial infection is usually controlled, guinea pigs consistently develop disseminated disease upon exposure to the aerosolized pathogen, facilitating subsequent analysis. Further, both guinea pigs and humans display cutaneous delayed-type hypersensitivity reactions characterized by the development of a dense mononuclear cell induration or rigid area at the skin test site. Finally, the characteristic tubercular lesions of humans and guinea pigs exhibit similar morphology including the presence of Langhans giant cells. As guinea pigs are more susceptible to initial infection and progression of the disease than humans, any protection conferred in experiments using this animal model provides a strong indication that the same protective immunity may be generated in man or other less susceptible mammals. Accordingly, for purposes of explanation only and not for purposes of limitation, the present invention will be primarily demonstrated in the exemplary context of guinea pigs as the mammalian host. Those skilled in the art will appreciate that the present invention may be practiced with other mammalian hosts including humans, mice and domesticated animals.

The only currently available vaccine, Mycobacterium bovis strain Bacille Calmette-Guérin (BCG), is of variable efficacy. Many studies have failed to demonstrate significant protection (see, e.g. Fine (1989). "The BCG story: lessons from the past and implications for the future." Rev Infect Dis 11 Suppl 2: S353-9). A large carefully conducted meta-analysis has estimated the potency of BCG to be approximately 50% (see, e.g. Colditz, et al. (1994). "Efficacy of BCG vaccine in the prevention of tuberculosis. Meta-analysis of the published literature." JAMA 271(9): 698-702). Despite its variable efficacy, several hundred million doses of the BCG vaccine are still administered to humans each year. Hence, a better vaccine or a vaccine that improves the potency of BCG by even a small amount could have a tremendous impact on the disease incidence.

A previous study examined the use of M. tuberculosis major extracellular proteins for immunizing against tuberculosis (see, e.g. Horwitz, et al. (1995). "Protective immunity against tuberculosis induced by vaccination with major extracellular proteins of Mycobacterium tuberculosis." Proc Natl Acad Sci USA 92(5): 1530-4). Another study examined a prime-boost vaccination strategy for boosting the level of protective immunity conferred by a prime vaccine such as BCG or recombinant BCG (see, e.g. Horwitz, et al. (2005). "Enhancing the protective efficacy of Mycobacterium bovis BCG vaccination against tuberculosis by boosting with the Mycobacterium tuberculosis major secretory protein." Infect Immun 73(8): 4676-83). In this study, the prime vaccine consisted of BCG or a recombinant BCG and the booster vaccine consisted of an M. tuberculosis major extracellular protein in adjuvant. Boosting BCG with such a vaccine enhanced the level of protective immunity conferred by BCG alone.

Other investigators have used various heterologous vectors to deliver M. tuberculosis proteins as booster vaccines for BCG, for example, adenovirus and modified vaccinia Ankara (see, e.g. McShane, et al. (2004). "Recombinant modified vaccinia virus Ankara expressing antigen 85A boosts BCG-primed and naturally acquired antimycobacterial immunity in humans." Nat Med 10(11): 1240-4; Williams, et al. (2005). "Boosting with poxviruses enhances *Mycobacterium bovis* BCG efficacy against *tuberculosis* in guinea pigs." *Infect Immun* 73(6): 3814-6; Santosuosso, et al. (2006). "Intranasal boosting with an adenovirus-vectored vaccine markedly enhances protection by parenteral *Mycobacterium bovis* BCG immunization against pulmonary *tuberculosis.*" *Infect Immun* 74(8): 4634-43; Vordermeier, et al. (2009). "Viral booster vaccines improve *Mycobacterium bovis* BCG-induced protection against bovine *tuberculosis.*" *Infect Immun* 77(8): 3364-73; Xing, et al. (2009). "Intranasal mucosal boosting with an adenovirus-vectored vaccine markedly enhances the protection of BCG-primed guinea pigs against pulmonary *tuberculosis.*" *PLoS One* 4(6): e5856). However, such vectors are difficult to produce because the viruses have to be grown in cell culture. Moreover, the efficacy of these virus-vectored vaccines as booster vaccines for BCG has not been high, especially with routes of administration other than intranasal. These vaccines have given little or no protection in the more challenging guinea pig model.

Therefore, a safe and effective vaccine against *M. tuberculosis* or other species of the genus *Mycobacterium* that is more potent than the currently available vaccines is sorely needed. There is also a need for a booster vaccine or a vaccine that can improve the potency of the currently available vaccines by even a small amount. The disclosure provided herein meets this need.

SUMMARY OF THE INVENTION

Current commercially available vaccines are of limited efficacy against pulmonary *tuberculosis*. The present disclosure provides a vaccine and method for preventing, reducing the possibility of or treating *tuberculosis* in humans and animals that is more potent than the current commercially available vaccines and methods in protecting against pulmonary *tuberculosis* and dissemination of bacteria to the spleen and other organs. The present disclosure also provides a vaccine and method for preventing, reducing the possibility of or treating leprosy and other mycobacterial diseases. Moreover, the present invention provides a booster vaccine that is surprisingly and unexpectedly more potent than a protein-in-adjuvant vaccine or an adenovirus-based vaccine. In addition, the present disclosure provides a vaccine that is easier and cheaper to manufacture than both virus-vectored vaccines, which must be grown in tissue culture cells and then purified, and protein-in-adjuvant vaccines, where the protein needs to be purified. The vaccine described in the present disclosure can simply be grown in broth culture—no purification is necessary.

The invention disclosed herein has a number of embodiments. A typical embodiment comprises a composition of matter that includes attenuated *Listeria monocytogenes* that expresses a *Mycobacterium tuberculosis* polypeptide, for example the 30 kDa antigen 85B protein (SEQ ID NO: 4). In such compositions, the *Listeria monocytogenes* is attenuated by inactivation (e.g. via deletion) of one or more genes so that it does not express a functional protein such as a ActA protein (SEQ ID NO: 1) and/or a InlB protein (SEQ ID NO: 2). In certain embodiments of the invention, attenuated *Listeria monocytogenes* expresses prfA protein having a G155S substitution mutation (SEQ ID NO: 3). In some embodiments of the invention, the composition comprises one or more agents commonly used in vaccines such as a pharmaceutically acceptable carrier.

While the 30 kDa antigen 85B protein (SEQ ID NO: 4) is a commonly discussed embodiment of the invention, other proteins, either alone, or in combination can be expressed in the attenuated *Listeria monocytogenes*. Such proteins include: *Mycobacterium tuberculosis* 12 kDa fragment of 16 kDa membrane protein (SEQ ID NO:5); *Mycobacterium tuberculosis* 14 kDa MPT53 protein (SEQ ID NO: 6); *Mycobacterium tuberculosis* 16 kDa MPT63 protein (SEQ ID NO: 7); *Mycobacterium tuberculosis* 23 kDa SOD protein (SEQ ID NO: 8); *Mycobacterium tuberculosis* 23.5 kDa MPT64 protein (SEQ ID NO: 9); *Mycobacterium tuberculosis* 24 kDa MPT51 protein (SEQ ID NO: 10); *Mycobacterium tuberculosis* 32 kDa antigen 85A protein (SEQ ID NO: 11); *Mycobacterium tuberculosis* 32 kDa antigen 85C protein (SEQ ID NO: 12); *Mycobacterium tuberculosis* 45 kDa MPT32 protein (SEQ ID NO: 13); *Mycobacterium tuberculosis* 58 kDa glutamine synthetase protein (SEQ ID NO: 14); *Mycobacterium tuberculosis* 71 kDa HSP 70 protein (SEQ ID NO: 15); *Mycobacterium tuberculosis* 10.4 kDa EsxH protein (SEQ ID NO: 16); *Mycobacterium tuberculosis* 14 kDa alpha crystalline homolog protein (SEQ ID NO: 17); *Mycobacterium tuberculosis* 47 kDa isocitrate lysate protein (SEQ ID NO: 18); *Mycobacterium tuberculosis* 7.6 kDa hypothetical protein (SEQ ID NO: 19); *Mycobacterium tuberculosis* 80 kDa glcB protein (SEQ ID NO: 20) *Mycobacterium tuberculosis* 110 kDa can protein (SEQ ID NO: 21); and *Mycobacterium tuberculosis* 9.9 kDa ESAT-6 protein (SEQ ID NO: 22). A wide variety of combinations of proteins can be expressed in various embodiments of the invention. For example, in certain embodiments of the invention, one or more latency associated proteins (e.g. SEQ NOS: 17-19) are expressed in combination with one or more of the other proteins disclosed herein (e.g. SEQ NOS: 4, 6-16 and 20-22).

In certain embodiments of the invention, the *Mycobacterium tuberculosis* 30 kDa antigen 85B protein is fused in frame with a heterologous protein sequence. Optionally, for example, the *Mycobacterium tuberculosis* 30 kDa antigen 85B protein is coupled to a heterologous protein sequence comprising the N-terminal 100 amino acids of the ActA protein. The protein expression can further be controlled by constructing expression cassettes to include certain regulatory sequences. In one illustrative embodiment of the invention, the expression of the *Mycobacterium tuberculosis* 30 kDa antigen 85B protein is controlled by an ActA promoter.

Another embodiment of the invention is a method of generating an immune response to a specific polypeptide, for example a *Mycobacterium tuberculosis* polypeptide such as the 30 kDa antigen 85B protein (SEQ ID NO: 4). Such methods include immunizing a mammal with a composition of matter disclosed herein, for example one comprising attenuated *Listeria monocytogenes* constructed to express *Mycobacterium tuberculosis* 30 kDa antigen 85B protein so that an antibody and/or a cellular immune response to *Mycobacterium tuberculosis* 30 kDa antigen 85B protein is generated. In an illustrative embodiment of invention, the *Listeria monocytogenes* does not express a functional ActA protein (SEQ ID NO: 1); does not express a functional InlB polypeptide (SEQ ID NO: 2); expresses prfA protein having a G155S substitution mutation (SEQ ID NO: 3); and expresses *Mycobacterium tuberculosis* 30 kDa antigen 85B protein (SEQ ID NO: 4). While the 30 kDa antigen 85B protein (SEQ ID NO: 4) is a commonly discussed embodiment of the invention, other proteins, either alone, or in combination can be expressed in the attenuated *Listeria monocytogenes* to generate an immune response.

Those of skill in this art understand that the immunization methods disclosed herein can be combined with other methodological steps. For example, certain embodiments of the invention include the step of further comprising immunizing the mammal with *Mycobacterium bovis* strain Bacille Calmette-Guérin (BCG). Typically in these embodiments, the BCG is used in a primary immunization and the attenuated *Listeria monocytogenes* is used in a booster immunization. In such embodiments of the invention, the mammal can be immunized intradermally, intranasally, orally, subcutaneously, percutaneouly, intramuscularly, intravenously, or by another conventional route of vaccine delivery.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE DRAWINGS

Referring now to the drawings and figures in which like reference numbers represent corresponding parts throughout.

DETAILED DESCRIPTION OF THE INVENTION

Figure 1:
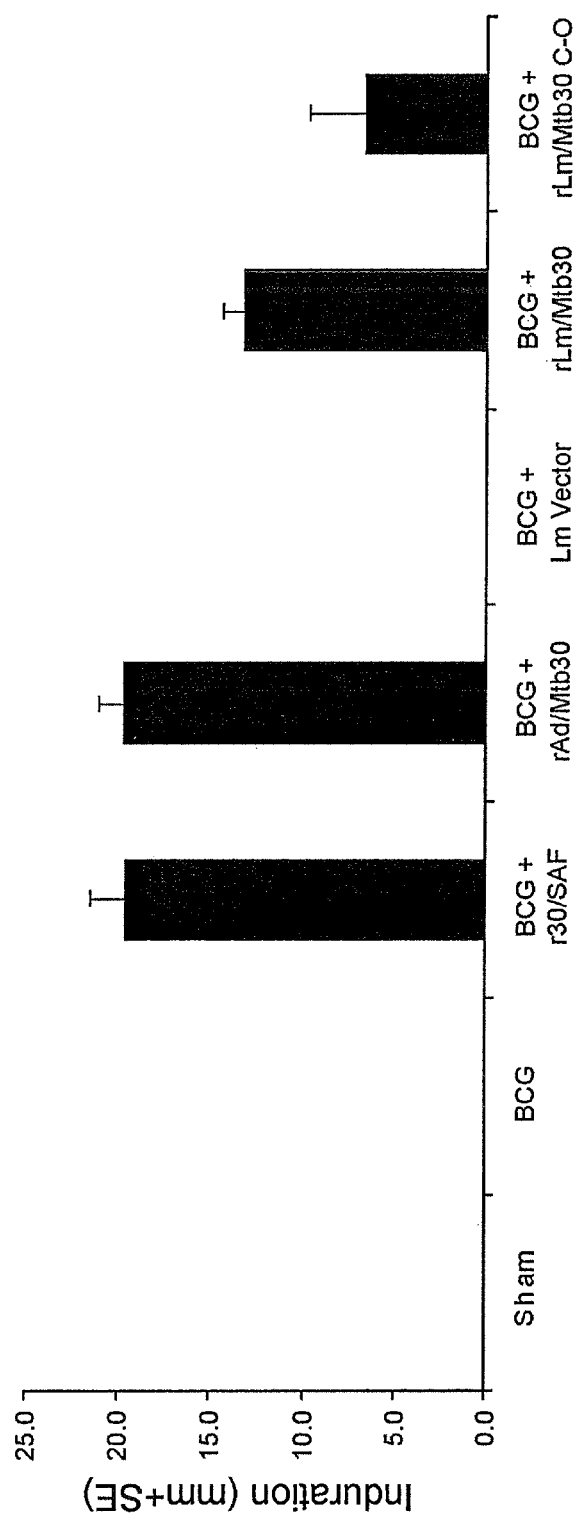
FIG. 1 is a graph illustrating measured diameters of induration (mm±SE) of guinea pigs after being injected intradermally with 10 μg of purified recombinant *M. tuberculosis* 30 kDa major extracellular protein (Antigen 85B; r30). As described herein under Experiment 1, guinea pigs were first immunized with various vaccines and then tested for cutaneous delayed-type hypersensitivity (c-DTH) to purified recombinant *M. tuberculosis* 30 kDa major extracellular protein (r30).

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. As appropriate, procedures involving the use of commercially available kits and reagents are generally carried out in accordance with manufacturer defined protocols and/or parameters unless otherwise noted.

In the following description of the typical embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

In one aspect of the present disclosure, a novel vaccine vector comprising attenuated *Listeria monocytogenes* is described. In one embodiment, a vector comprising attenuated *Listeria monocytogenes* is used by itself as a primary vaccine or vaccinating agent. In another embodiment, a vector comprising attenuated *Listeria monocytogenes* is used for delivering *M. tuberculosis* proteins as a booster vaccine for another *tuberculosis* (TB) vaccine, such as BCG or recombinant BCG. In a further embodiment, a vector comprising attenuated *Listeria monocytogenes* is used for delivering mycobacteria proteins, such as proteins from *Mycobacterium bovis* and *Mycobacterium leprae*, as a primary or booster vaccine or vaccinating agent. Unexpectedly, utilizing a vector comprising attenuated *Listeria monocyto-* genes for delivering mycobacteria proteins as a booster vaccine induces greater protective immunity than boosting with just the purified proteins in adjuvant or boosting with a recombinant adenovirus encoding the same proteins.

Attenuated *Listeria monocytogenes* can be used as vectors to deliver *M. tuberculosis* major extracellular proteins, which include but are not limited to the 30 kDa major secretory protein (Antigen 85B), 32A major secretory protein (Antigen 85A), 32B major secretory protein (Antigen 85C), the 23.5 kDa major secretory protein (a.k.a. MPT64), the 16 kDa major secretory protein, the 23 kDa subunit mass superoxide dismutase, the 58 kDa subunit mass glutamine synthetase, the 71 kDa subunit mass heat shock protein, the 12 kDa subunit mass exported fragment of the 16 kDa alpha-crystallin protein, and the 14 kDa secreted protein, etc. Such extracellular proteins have been shown to be immunoprotective against *M. tuberculosis* (see, e.g. Horwitz, et al. (1995). "Protective immunity against *tuberculosis* induced by vaccination with major extracellular proteins of *Mycobacterium tuberculosis.*" Proc Natl Acad Sci USA 92(5): 1530-4).

In one exemplary implementation of the present disclosure, BCG is utilized as a first vaccine with a booster vaccine being a recombinant attenuated *Listeria monocytogenes* expressing the *M. tuberculosis* 30 kDa major secretory protein, a.k.a. Antigen 85B or r30 (rLm/Mtb30). In the Examples described herein, boosting with rLm/Mtb30 has been compared with boosting with purified *M. tuberculosis* 30 kDa major secretory protein in adjuvant or boosting with a recombinant Adenovirus expressing the *M. tuberculosis* 30 kDa major secretory protein. Surprisingly, this method of immunization is found to induce significantly greater protective immunity than boosting with just the purified *M. tuberculosis* protein in adjuvant or boosting with a recombinant adenovirus encoding the same protein.

In another aspect of the present disclosure, a composition of matter is described that is useful for preventing or reducing the possibility of infection caused by *Mycobacterium tuberculosis*, the agent of *tuberculosis*, or infection by other pathogenic strains of mycobacteria in humans and/or animals including *Mycobacterium bovis* and *Mycobacterium leprae*. Administration of the composition of matter comprising attenuated *Listeria monocytogenes* expressing a major extracellular protein induces a cell-mediated immune response to the recombinant major extracellular protein. This subsequently protects against infection by *M. tuberculosis* or other mycobacterial diseases. In yet another aspect of the present disclosure, a vaccination strategy is described wherein an attenuated *Listeria monocytogenes* expressing *M. tuberculosis* proteins is administered by itself. In one embodiment, rLm/Mtb30 is administered by itself.

In a further aspect of the present disclosure, a vaccination strategy is described wherein an attenuated *Listeria monocytogenes* expressing *M. tuberculosis* proteins is administered as a booster vaccine following immunization with another TB vaccine. In one embodiment, rLm/Mtb30 is administered as a heterologous booster vaccine following immunization with another TB vaccine, such as BCG or a recombinant BCG expressing the same protein. For example, BCG or recombinant BCG is administered first, and after a period of time, the rLm/Mtb30 vaccine is administered one or more times. The initial vaccination may be with BCG or any recombinant strain of BCG overexpressing and secreting one or more *M. tuberculosis* major extracellular proteins, including but not limited to the 30 kDa major secretory protein (Antigen 85B), 32A major secretory protein (Antigen 85A), 32B major secretory protein (Antigen 85C), the 23.5 kDa major secretory protein (a.k.a. MPT64), the 16 kDa major secretory protein, the 23 kDa subunit mass superoxide dismutase, the 58 kDa subunit mass glutamine synthetase, the 71 kDa subunit mass heat shock protein, the 12 kDa subunit mass exported fragment of the 16 kDa alpha-crystallin protein, the 14 kDa secreted protein, etc. The subsequent vaccination would be with recombinant attenuated *Listeria monocytogenes* expressing the same *M. tuberculosis* protein.

The attenuated *Listeria monocytogenes* can be administered intradermally or by another route, e.g. intranasally, subcutaneously, percutaneously, intramuscularly, or even orally to a mammalian host. The vaccines or immunotherapeutic agents and methods for their use disclosed herein may be used to impart acquired immunity in a mammalian host against various intracellular pathogens, including but not limited to *M. tuberculosis, M. bovis, M. kansasii, M. avium-intracellulare, M. fortuitum, M. chelonei, M. marinum, M. scrofulaceum, M. leprae, M. africanum, M. ulcerans*, and *M. microti*.

As illustrated above, the invention disclosed herein has a number of embodiments. A typical embodiment comprises a composition of matter that includes live attenuated *Listeria monocytogenes* that expresses a *Mycobacterium tuberculosis* polypeptide, for example the 30 kDa antigen 85B protein (SEQ ID NO: 4). In such compositions, the *Listeria monocytogenes* is attenuated by inactivation (e.g. via deletion) of one or more genes so that it does not express a functional protein such as a ActA protein (SEQ ID NO: 1) and/or a InlB protein (SEQ ID NO: 2). In certain embodiments of the invention, attenuated *Listeria monocytogenes* expresses prfA protein having a G155S substitution mutation (SEQ ID NO: 3).

While the 30 kDa antigen 85B protein (also called herein the *M. tuberculosis* 30 kDa major secretory protein r30) is a commonly discussed embodiment of the invention, other proteins, either alone, or in combination can be expressed in the attenuated *Listeria monocytogenes* (e.g. an attenuated *Listeria monocytogenes* of strain 10403S). Such proteins include: *Mycobacterium tuberculosis* 12 kDa fragment of 16 kDa membrane protein (SEQ ID NO:5); *Mycobacterium tuberculosis* 14 kDa MPT53 protein (SEQ ID NO: 6); *Mycobacterium tuberculosis* 16 kDa MPT63 protein (SEQ ID NO: 7); *Mycobacterium tuberculosis* 23 kDa SOD protein (SEQ ID NO: 8); *Mycobacterium tuberculosis* 23.5 kDa MPT64 protein (SEQ ID NO: 9); *Mycobacterium tuberculosis* 24 kDa MPT51 protein (SEQ ID NO: 10); *Mycobacterium tuberculosis* 32 kDa antigen 85A protein (SEQ ID NO: 11); *Mycobacterium tuberculosis* 32 kDa antigen 85C protein (SEQ ID NO: 12); *Mycobacterium tuberculosis* 45 kDa MPT32 protein (SEQ ID NO: 13); *Mycobacterium tuberculosis* 58 kDa glutamine synthetase protein (SEQ ID NO: 14); *Mycobacterium tuberculosis* 71 kDa HSP 70 protein (SEQ ID NO: 15); *Mycobacterium tuberculosis* 10.4 kDa EsxH protein (SEQ ID NO: 16); *Mycobacterium tuberculosis* 14 kDa alpha crystalline homolog protein (SEQ ID NO: 17); *Mycobacterium tuberculosis* 47 kDa isocitrate lysate protein (SEQ ID NO: 18); *Mycobacterium tuberculosis* 7.6 kDa hypothetical protein (SEQ ID NO: 19); *Mycobacterium tuberculosis* 80 kDa glcB protein (SEQ ID NO: 20) *Mycobacterium tuberculosis* 110 kDa can protein (SEQ ID NO: 21); and *Mycobacterium tuberculosis* 9.9 kDa ESAT-6 protein (SEQ ID NO: 22). A wide variety of combinations of proteins can be expressed in various embodiments of the invention. For example, in certain embodiments of the invention, one or more latency associated proteins (e.g. SEQ NOS: 17-19) are expressed in combination with one or more of the other proteins disclosed herein (e.g. SEQ NOS: 4, 6-16 and 20-22).

In some embodiments of the invention, the composition comprises one or more agents used in vaccines such as a pharmaceutically acceptable carrier. Methods for formulating compositions of the invention for pharmaceutical administration are known to those of skill in the art. See, for example, Remington: The Science and Practice of Pharmacy, 19th Edition, Gennaro (ed.) 1995, Mack Publishing Company, Easton, Pa. Typically the immunogenic agents used in the methods of the invention combined with at pharmaceutically acceptable carrier. The term "pharmaceutically acceptable carrier" is used according to its art accepted meaning and is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions. A pharmaceutical composition of the invention is formulated to be compatible with its intended route of administration. Certain compositions of the invention can include an adjuvant. Immunologic adjuvants are commonly added to vaccines to stimulate the immune system's response to the target antigen, but do not in themselves confer immunity. Adjuvants can act in various ways in presenting an antigen to the immune system. A wide variety of adjuvants are known in the art, see e.g. Handbook of Pharmaceutical Additives: An International Guide to More Than 6000 Products by Trade Name, Chemical, Function, and Manufacturer by Michael Ash and Irene Ash (1996). In addition, certain embodiments of the invention further comprising a buffer system, for example phosphate buffered saline.

In certain embodiments of the invention, a protein such as the *Mycobacterium tuberculosis* 30 kDa antigen 85B protein is fused in frame with a heterologous protein sequence. Optionally, for example, the *Mycobacterium tuberculosis* 30 kDa antigen 85B protein is coupled to a heterologous protein sequence comprising the N-terminal 100 amino acids of the ActA protein. The protein expression can further be controlled by constructing expression cassettes to include certain regulatory sequences. In one illustrative embodiment of the invention, the expression of the *Mycobacterium tuberculosis* 30 kDa antigen 85B protein is controlled by an ActA promoter.

Another embodiment of the invention is a method of generating an antibody to a *Mycobacterium tuberculosis* polypeptide such as the 30 kDa antigen 85B protein (SEQ ID NO: 4) by immunizing a mammal with a composition of matter disclosed herein, for example one comprising attenuated *Listeria monocytogenes* constructed to express this protein so that an antibody to a *Mycobacterium tuberculosis* 30 kDa antigen 85B protein is generated. The term "mammal" as used herein refers to any organism classified as a mammal, including mice, rats, rabbits, dogs, cats, cows, horses and humans. In one embodiment of the invention, the mammal is a mouse. In another embodiment of the invention, the mammal is a human. In an illustrative embodiment of invention, the *Listeria monocytogenes* does not express a functional ActA protein (SEQ ID NO: 1); does not express a functional InlB polypeptide (SEQ ID NO: 2); expresses prfA protein having a G155S substitution mutation (SEQ ID NO: 3); and expresses *Mycobacterium tuberculosis* 30 kDa antigen 85B protein (SEQ ID NO: 4). While the 30 kDa antigen 85B protein (SEQ ID NO: 4) is a commonly discussed embodiment of the invention, other proteins, either alone, or in combination can be expressed in the attenuated *Listeria monocytogenes* to generate an immune response.

Those of skill in this art understand that the immunization methods disclosed herein can be combined with other methodological steps. For example, certain embodiments of the invention include the step of further comprising immunizing the mammal with *Mycobacterium bovis* strain Bacille Calmette-Guérin (BCG). Typically in these embodiments, the BCG is used in a primary immunization and the attenuated *Listeria monocytogenes* is used in a booster immunization. In such embodiments of the invention, the mammal can be immunized intranasally, orally, subcutaneously, percutaneouly, intramuscularly, or by anther conventional route of vaccine delivery.

Antibodies generated by methodological embodiments of the invention have a number of uses. In one exemplary use in vivo, antibodies to an antigen such as a *Mycobacterium tuberculosis* protein are useful to prevent and/or diminish the severity of a disease such as *tuberculosis*. In yet another exemplary use, antibodies to a *Mycobacterium tuberculosis* protein such as 30 kDa antigen 85B protein (SEQ ID NO: 4) can function as an essential element in a diagnostic assay. In particular, those of skill in this art understand that a wide variety of diagnostic assays use antigen specific antibodies to provide substantial beneficial information to medical personnel including ELISA assay, Western Assays, radioimmunoassays and the like. Such assays use antibodies specific for an antigen such as a protein expressed by a pathogenic organism to, for example, identify the presence of that organism in a sample. Examples of *tuberculosis* diagnosis using antibodies in ELISA systems are described in publications such as Radhakrishnan et al., *J Infect Dis,* 1991 163(3): 650-652 and Kashyap et al., *Clin Diag Lab Immunol.* 2005 12(6): 752-758, the contents of which are incorporated by reference herein. In addition, a number of commercially available kits are known in the art such as the Clearview TB ELISA system. As is known in the art, antibodies useful in such assays can be obtained, for example, from the supernatants of hybridomas generated by conventional methods and/or affinity purified from human sera (see, e.g., Groen et al., J Virol Methods. 1989 February; 23(2):195-203, the contents of which are incorporated by reference). In this context, antibodies generated by the methods of the invention can be readily adapted for use in such assays.

Those skilled in the art will appreciate that the exemplary discussions of *M. tuberculosis* that are provided herein are in no way intended to limit the scope of the present invention to the treatment of *M. tuberculosis*. Similarly, the teachings herein are not limited in any way to the treatment of tubercular infections. On the contrary, this invention may be used to advantageously provide safe and effective vaccines and immunotherapeutic agents against the immunogenic determinants of any pathogenic agent expressing extracellular products and thereby inhibit the infectious transmission of those organisms.

EXAMPLES

Materials and Methods
A. BCG Strain (Wild-type *M. bovis* BCG Tice)
This strain was maintained in 7H9 medium pH 6.7 (Difco) at 37° C. in a 5% $CO_2$-95% air atmosphere as unshaken cultures. Cultures were sonicated once or twice weekly for 5 min in a sonicating water bath to reduce bacterial clumping, as described (see, e.g. Horwitz, et al. (2000). "Recombinant *bacillus* calmette-guerin (BCG) vaccines expressing the *Mycobacterium tuberculosis* 30-kDa major secretory protein induce greater protective immunity against *tuberculosis* than conventional BCG vaccines in a highly susceptible animal model." *Proc Natl Acad Sci USA* 97(25): 13853-8).

B. Recombinant Attenuated *Listeria monocytogenes* Vaccines 1. rLm/Mtb30(01)

a. Construction of rLm/Mtb30(01)

rLm/Mtb30(01), an attenuated recombinant *Listeria monocytogenes* expressing the *M. tuberculosis* 30 kDa major secretory protein (Mtb30), was constructed using the attenuated *L. monocytogenes* host strain, LmΔactA, an *L. monocytogenes* strain 10403S (serotype 1/2a) with a deletion of actA encoding one of virulence factors, ActA. The coding sequence for the mature peptide of the 30 kDa major secretory protein was PCR amplified from the genomic DNA of the *M. tuberculosis* 37HRv strain. The DNA fragments were cloned into pZErO (Invitrogen) vector. The identity of the inserted 30 kDa coding sequences was confirmed by nucleotide sequencing, and subcloned into the BamHI and PacI sites of the cloning vector pKB199, in such a way that the 30 kDa coding sequence was fused to the listeriolysin O signal sequence (LLO) downstream of the hemolysin (hly) promoter of *L. monocytogenes*. The expression cassette of the LLO-30 kDa fusion protein driven by the hly promoter was excised from the resultant vector and subsequently cloned into a site-specific integration vector pDP4189. The integration vector was transformed into SM10, the *E. coli* conjugation donor strain. Through conjugation, the plasmid was mobilized and transferred from its *E. coli* SM10 host into the recipient LmΔactA strain. The conjugation mixture was selected on plates containing streptomycin and chloramphenicol. The LmΔactA strain is insensitive to streptomycin since it is derived from the *L. monocytogenes* strain 10403S, a spontaneous mutant resistant to streptomycin. *E. coli* SM10 is sensitive to streptomycin, therefore was not able to grow on the selective plate. The plasmid pDP4189 carries the chloramphenicol resistance gene and is unable to replicate in *Listeria*. Under the selection pressure from chloramphenicol, the plasmid pDP4189/Mtb30 integrated in the 3' end of an arginine tRNA gene on the chromosome of LmΔactA strain. The resultant recombinant LmΔactA strain, rLm/Mtb30(01), carries a single copy of the 30 kDa expression cassette and is stable in the absence of antibiotic selection.

b. Protein Expression of Mtb30 in Broth.

The expression of 30 kDa major secretory protein by rLm/Mtb30 was tested in broth. A single colony of rLm/Mtb30(01) was inoculated into 3 ml Brain Heart Infusion (BHI) medium containing streptomycin and chloramphenicol and the bacteria were grown overnight at 37° C. with shaking. The overnight culture was inoculated into 40 ml fresh MOPS-buffered BHI medium containing streptomycin and chloramphenicol at an initial optical density (OD) of 0.05 at 540 nm. The culture was grown until late logarithmic phase at 37° C. with vigorous shaking before being harvested by centrifugation. The supernate was passed through a 0.2 μm filter membrane, and proteins in the culture filtrate were precipitated by trichloroacetic acid. The expression of the 30 kDa major secretory protein was analyzed by Western blotting using rabbit polyclonal antibody against the 30 kDa major secretory protein. It was found that the antibody reacted specifically with a protein band of 30 kDa, which was absent from the LmΔactA parental strain. This confirmed that the recombinant rLm/Mtb30 expresses the 30 kDa protein.

c. Protein Expression of Mtb 30 by rLm/Mtb30(01) in Human Macrophages

THP-1 cells were differentiated into a monolayer on a 24-well plate ($2 \times 10^5$ cells/well) in the presence of 100 nM PMA (phorbol 12-myristate 13-acetate) and in the absence of antibiotics. The rLm/Mtb30(01) culture was grown to late logarithmic phase (OD of 1.0 at 540 nm) in BHI broth and used to infect the THP-1 cell monolayer at a multiplicity of infection (MOI) of 50:1. After infection for 1 h at 37° C., the monolayer was washed twice with RPMI to remove extracellular bacteria and then treated with 1 ml medium containing gentamicin at a final concentration of 10 μg ml$^{-1}$ to kill any remaining extracellular bacteria. At 24 h post-infection, cells were harvested, washed once with PBS, and boiled for 7 min in Laemmli buffer before analysis by SDS-polyacrylamide gel electrophoresis (SDS-PAGE) and Western blotting. It shows that bands of ~30 kDa in size were detected in samples of macrophages infected by two clones of rLm/Mtb30(01), but not by the parental rLmΔactA strain. These two clones (#8 and #10) were amplified in BHI broth and used for animal experiments.

2. rLm/Mtb30(02) (Codon Optimized)

rLm/Mtb30(02), rLmΔactA expressing the 30 kDa protein codon-optimized for higher level of protein expression in *L. monocytogenes* (30 kDa(C—O)), was constructed using a method similar to that described above for rLm/Mtb30(01). The DNA sequence for a codon-optimized version of the 30 kDa major secretory protein (30 kDa(C—O)) was synthesized by DNA2.0 (Menlo Park, Calif.).

3. rLmΔactAΔinlB/Mtb30 (rLm/Mtb30(11))

To further reduce the toxicity of the LmΔactA vector, a second generation of rLm/Mtb30 vaccines were constructed using a *L. monocytogenes* with deletions in actA and inlB (LmΔactAΔinlB) as a vector. Deletions in actA and inlB retain the potency and diminish the toxicity of the Lm vector in vivo (see, e.g. Brockstedt, et al. (2004). "*Listeria*-based cancer vaccines that segregate immunogenicity from toxicity." *Proc Natl Acad Sci USA* 101(38): 13832-7). It was shown that the 30 kDa protein was readily detected by Coumassie blue staining in broth cultures of the vaccine and in extracts of macrophages infected with rLm/Mtb30(11).

4. rLmΔactAΔinlB/ActAN100-Mtb30 (rLm/Mtb30(03)(04))

It has been reported that the actA promoter has a higher activity than hly promoter in vivo and proteins fused with 100 amino acids of the N-terminus of ActA are highly immunogenic. Therefore to enhance the in vivo expression of 30 kDa protein by the rLm/Mtb30 vaccines, the 30 kDa major secretory protein was fused with the N-terminal 100 amino acids of ActA (ActAN100) under the control of the actA promoter and introduced the fusion protein expression cassette into the second generation of the rLmΔactAΔinlB vector. The following 2 additional second generation of rLm/Mtb30 vaccines have been constructed:

a. rLmΔactAΔinlB/ActAN100-Mtb30 (03)

b. rLmΔactAΔinlB/ActAN100-Mtb30-SL8 (04)

It has been shown that these second generation rLm/Mtb30 vaccines express the 30 kDa major secretory protein in broth culture and in human macrophages at levels similar to that of the first generation rLm/Mtb30 vaccines. The safety of these vaccines in animals are further being tested.

5. rLmΔactAΔinlBΔuvrABprfA*/Mtb30 (12)(07)(08)

To further enhance the immunogenicity of the rLm/Mtb30 vaccines, the following third generation rLm/Mtb30 vaccines expressing high amounts of the 30 kDa protein have been constructed and characterized.

a. rLmactAΔinlBΔuvrABprfA*/Mtb30 (12)
b. rLmactAΔinlBΔuvrABprfA*/ActAN100-Mtb30 (07)
c. LmactAΔinlBΔuvrABprfA*/ActAN100-Mtb30-SL8 (08)

The third generation rLm/Mtb30 vaccines were constructed using as a vector an LmΔactAΔinlB with an additional deletion in uvrAB and a single mutation (G155S) in pfrA (LmΔactAΔinlBΔuvrABprfA*, or Lm/prfA*) provided by Aduro BioTech. The deletion in uvrAB was designed to facilitate inactivation of the rLm/prfA* vaccines by UV light (Brockstedt et al. 2005) and the prfA* mutation resulted in constitutive expression of the downstream genes, including actA and hly (see, e.g. Lauer, et al. (2008). "Constitutive Activation of the PrfA regulon enhances the potency of vaccines based on live-attenuated and killed but metabolically active *Listeria monocytogenes* strains." *Infect Immun* 76(8): 3742-53; Yan, et al. (2008). "Selected prfA* mutations in recombinant attenuated *Listeria monocytogenes* strains augment expression of foreign immunogens and enhance vaccine-elicited humoral and cellular immune responses." *Infect Immun* 76(8): 3439-50). It was shown that all three rLm/pfrA*/Mtb30 vaccines expressed the 30 kDa fusion proteins at significantly higher levels in broth than the corresponding vaccines derived from the first and second generation Lm vectors (rLmΔactA and rLmΔactAΔinlB)

C. Purified *M. tuberculosis* 30 kDa Major Secretory Protein

This protein was purified from recombinant *M. smegmatis* as described in Horwitz et al. 1995 (see, e.g. Horwitz, et al. (1995). "Protective immunity against *tuberculosis* induced by vaccination with major extracellular proteins of *Mycobacterium tuberculosis*." *Proc Natl Acad Sci USA* 92(5): 1530-4) and Harth et al. 1997 (see, e.g. Harth, et al. (1997). "High-level heterologous expression and secretion in rapidly growing nonpathogenic mycobacteria of four major *Mycobacterium tuberculosis* extracellular proteins considered to be leading vaccine candidates and drug targets." *Infect Immun* 65(6): 2321-8).

D. Replication-Deficient Adenovirus Expressing the 30 kDa Major Secretory Protein: Generation of Strains and Recombinant Protein Expression The replication-deficient recombinant adenovirus strain that expresses the 30 kDa major secretory protein of *M. tuberculosis* (Mtb30) was constructed using an AdenoVator system (Q Biogen). The Mtb30 coding sequence was first cloned into a transfer vector of pAdenoVator-CMV5 downstream of a modified immediate-early promoter of cytomegalovirus (CMV5), which allows for the production of high levels of heterologous proteins in mammalian cells. The transfer vector contains a kanamycin-resistance gene that allows for selection of recombinant adenoviral DNAs. The transfer vector containing the Mtb30 coding sequence was then co-transformed into *E. coli* together with an adenoviral plasmid DNA with deletions in viral early genes E1 and E3, pAdenoVatorΔE1/E3. The E1 but not the E3 gene is essential for adenovirus growth in mammalian cells. Thus the recombinant adenoviruses with E1 and E3 deletions are replication-deficient and can grow only on cells that express the E1 gene. Through homologous recombination between the transfer vector and the adenoviral plasmid DNA in *E. coli*, the Mtb30 gene driven by the CMV5 promoter was introduced into the deleted E1 region of the adenoviral plasmid DNA. Recombinant adenoviral DNAs were selected with kanamycin and confirmed by restriction enzyme analysis. A positive recombinant adenoviral DNA that was confirmed to contain the appropriate insert, pAdvΔE1E3/Mtb30, was linearized with restriction enzyme (PacI) and transfected into mammalian cells (293A) that express the E1 protein. The resultant replication-deficient recombinant adenoviruses were plaque purified and amplified in 293A cells for up to 4 passages. The expression of Mtb30 by the recombinant adenovirus, AdvΔE1E3/Mtb30, was confirmed by Western blotting using a rabbit polyclonal antibody to Mtb30. The replication-deficient recombinant adenovirus stock was prepared from $6 \times 10^8$ 293A cells and purified by two rounds of ultracentrifugation on CsCl gradients. The amount of virus particles in the virus stock was measured by assessing the DNA content of lysed virus in solution and utilizing the extinction coefficient of $1.1 \times 10^{12}$ virus particles per $OD_{260}$ unit. The amount of infectious virus in the virus stock was measured by determining the tissue culture infectious dose 50 ($TCID_{50}$) in 293A cells. The purified viral particles were stored at −80° C. in 20 mM Tris, pH 8.0, 25 mM NaCl, 2.5% glycerol.

E. Animal Models

The studies of the efficacy of the vaccines utilized guinea pigs because the guinea pig model is especially relevant to human *tuberculosis* clinically, immunologically, and pathologically. In contrast to the mouse and rat, but like the human, the guinea pig a) is susceptible to low doses of aerosolized *M. tuberculosis*; b) exhibits strong cutaneous delayed-type hypersensitivity (DTH) to tuberculin; and c) displays Langhans giant cells and caseation in pulmonary lesions. However, whereas only about 10% of immunocompetent humans who are infected with *M. tuberculosis* develop active disease over their lifetime (half early after exposure and half after a period of latency), infected guinea pigs always develop early active disease. While guinea pigs differ from humans in this respect, the consistency with which they develop active disease after infection with *M. tuberculosis* is an advantage in trials of vaccine efficacy.

Additional immunology studies including studies requiring special immunology reagents were conducted in C57BL/6 mice.

F. Preparation of Primary Vaccination

Aliquots were removed from logarithmically growing wild-type or recombinant BCG cultures, and the bacteria were pelleted by centrifugation at 3,500×g for 15 min. The bacteria were then washed with 1× phosphate buffered saline (1×PBS, 50 mM sodium phosphate pH 7, 150 mM sodium chloride) and resuspended at a final concentration of $1 \times 10^4$ colony forming units per ml in 1×PBS. The immunization inoculum contained 1,000 viable wild-type or recombinant BCG bacteria in a total volume of 100 μl.

G. Preparation of Booster Vaccination 1. rLm/Mtb30.

The various rLm/Mtb30 vaccines were grown in broth. Aliquots were removed from late logarithmically growing rLm/Mtb30 cultures and the bacteria were pelleted by centrifugation at 3,500×g for 15 min. The bacteria were then washed once with 1× phosphate buffered saline (1×PBS, 50 mM sodium phosphate pH 7, 150 mM sodium chloride) and re-suspended at a final concentration of $2 \times 10^9$ colony forming units per ml in 1× sterile PBS. The stock was stored at −80° C., and the titer was checked periodically by plating serial dilutions of the stock on BHI plates. No significant titer loss was found over the period of storage. Before each use in animals, one vial of rLm/Mtb30 was thawed immediately at 37° C., diluted in sterile saline to a final concentration of $2 \times 10^7$ colony forming units per ml in 1× sterile PBS and kept on ice until use. The rLm/Mtb30 was administered intradermally at a dose of $1\times10^6$ bacteria in a total of 50 µL per animal.

2. r30 in Adjuvant

100 µg of the r30 protein was mixed with Syntex Adjuvant Formulation (SAF) as described in Horwitz et al. 1995 (see, e.g. Horwitz, et al. (1995). "Protective immunity against tuberculosis induced by vaccination with major extracellular proteins of Mycobacterium tuberculosis." Proc Natl Acad Sci USA 92(5): 1530-4).

3. rAd/Mtb30

The rAd/Mtb30 stock was thawed on ice, diluted in sterile PBS to a final concentration of $1\times10^{11}$ viral particles per mL and administered intradermally at a dose of $1\times10^{11}$ viral particles in a total 50 µL per animal.

Experiments

Experiment 1: Immunogenicity of rLm/Mtb30 in Prime-Boost Vaccination Regimen

Specific-pathogen free 250-300 g outbred male Hartley strain guinea pigs from Charles River Breeding Laboratories, in groups of 6, were immunized intradermally as follows:

Group A: Sham
Group B: BCG Tice Parental Control ($10^3$ CFU) at Week 0
Group C: BCG Tice Parental Control ($10^3$ CFU) at Week 0 and 100 µg of r30 in SAF adjuvant at Week 4
Group D: BCG Tice Parental Control ($10^3$ CFU) at Week 0 and rAd/Mtb30 at Week 4
Group E: BCG Tice Parental Control ($10^3$ CFU) at Week 0 and Lm Empty Vector at Week 4
Group F: BCG Tice Parental Control ($10^3$ CFU) at Week 0 and rLm/Mtb30 at Week 4
Group G: BCG Tice Parental Control ($10^3$ CFU) at Week 0 and rLm/Mtb30 C—O at Week 4

At week 8, animals were tested for cutaneous delayed-type hypersensitivity (c-DTH) to r30, and after the skin test was assessed, the animals were euthanized for assay of splenic lymphocyte proliferation and antibody responses to r30.

A. Cutaneous Delayed-Type Hypersensitivity (DTH) to Purified Recombinant M. tuberculosis 30 kDa Major Extracellular Protein (r30)

Guinea pigs were shaved over the back and injected intradermally with 10 µg of purified recombinant M. tuberculosis 30 kDa major extracellular protein (r30) in 100 µl phosphate buffered saline. After 24 h, the diameter of erythema and induration was measured. Induration is most reflective of a c-DTH response. The results are summarized in Table 1 and FIG. 1.

TABLE 1

Cutaneous DTH - Experiment 1

| Group | Vaccination | Test Antigen | Erythema (mm ± SE) | Induration (mm ± SE) |
|---|---|---|---|---|
| A | Sham | r30 | 0 ± 0 | 0 ± 0 |
| B | BCG | r30 | 0 ± 0 | 0 ± 0 |
| C | BCG + r30 | r30 | 19.6 ± 1.9 | 19.6 ± 1.9 |
| D | BCG + rAd/Mtb30 | r30 | 19.7 ± 1.4 | 19.7 ± 1.4 |
| E | BCG + Lm Vector | r30 | 1.2 ± 0.7 | 0 ± 0 |
| F | BCG + rLm/Mtb30 | r30 | 13.3 ± 1.1 | 13.3 ± 1.1 |
| G | BCG + rLm/Mtb30 C-O | r30 | 12.3 ± 1.0 | 6.7 ± 3.1 |

These results showed that the animals immunized with the parental BCG Tice strain (Group F) and the sham-immunized animals (Group J) had no erythema and induration upon testing with the M. tuberculosis 30 kDa major secretory protein r30. In contrast, animals immunized with BCG and boosted with purified r30 in adjuvant or with recombinant vaccines expressing r30, including both recombinant adenovirus and recombinant L. monocytogenes all developed significantly increased levels of both erythema and, more importantly, induration in response to skin-testing with r30. Boosting with the empty L. monocytogenes vector did not induce a significant c-DTH response (0 induration). Both rLm/Mtb30 and rLm/Mtb30C—O induced a significant c-DTH response.

B. Splenic Lymphocyte Proliferation to Purified Recombinant M. tuberculosis 30 kDa Major Extracellular Protein (r30)

Figure 2:
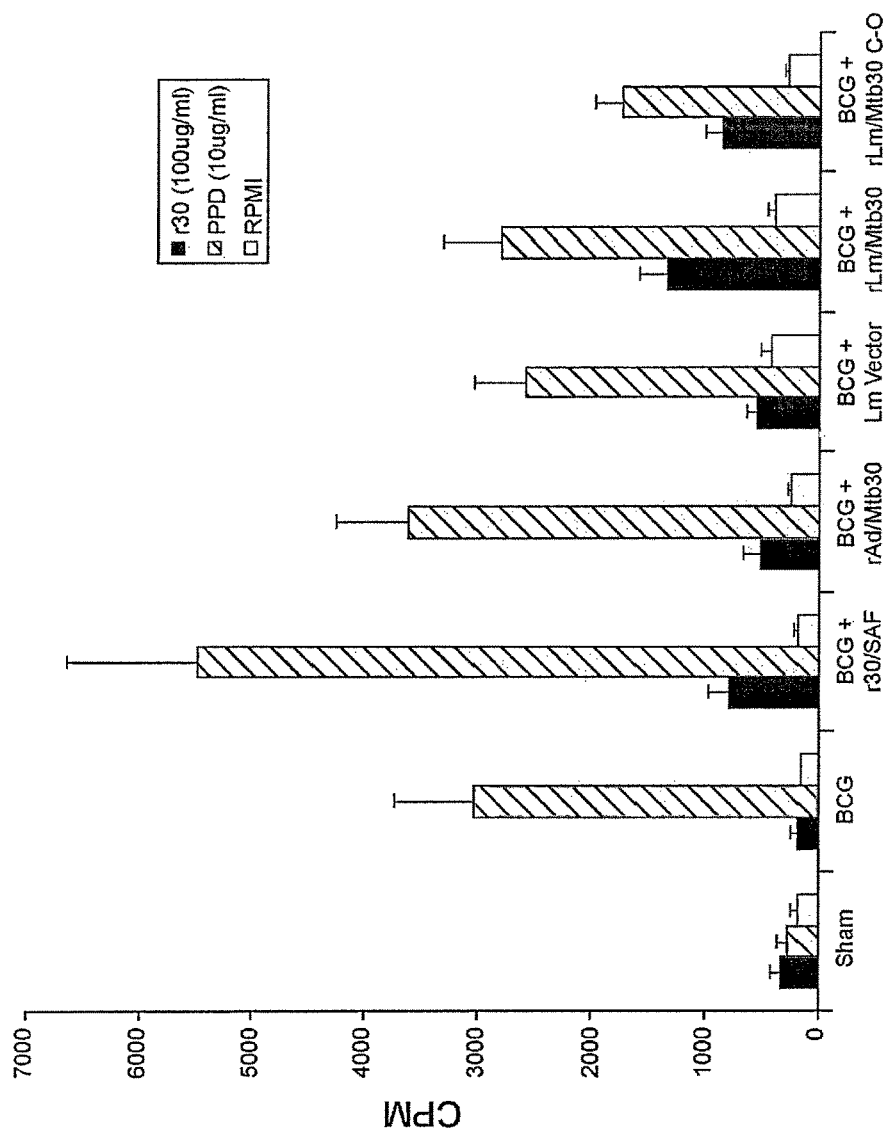
FIG. 2 is a graph illustrating splenic lymphocyte proliferation to r30, PPD, and media alone (RPMI). As described herein under Experiment 1, guinea pigs were first immunized with various vaccines and then assayed for splenic lymphocyte proliferation to purified recombinant *M. tuberculosis* 30 kDa major extracellular protein.

Immediately after skin-testing, the animals were euthanized, their spleens removed, and splenic lymphocyte proliferation to r30 (100 µg/well) and PPD (10 µg/well) assayed. The results are shown in Table 2 and FIG. 2.

As expected, all but the sham-immunized animals reacted to the positive control antigen PPD. The sham and BCG-immunized animals had low lymphocyte proliferative activity. Animals immunized with BCG and boosted with either rAd/Mtb30 or the Lm vector had modest lymphocyte proliferative activity. Boosting BCG-immunized animals with r30 markedly increased lymphocyte proliferative activity approximately 4-fold vs. BCG-immunized animals. Boosting BCG-immunized animals with rLm/Mtb30 or rLm/Mtb 30 C—O also markedly increased splenic lymphocyte proliferative activity by ~7-fold and 4-fold, respectively vs. BCG immunized animals.

Thus, boosting with recombinant L. monocytogenes expressing the M. tuberculosis 30 kDa major secretory protein markedly increased splenic lymphocyte proliferation to r30 in guinea pigs.

TABLE 2

Splenic Lymphocyte Proliferation - Experiment 1

| Group | Vaccination | Test Antigen | r30 (Mean CPM ± SE) | PPD (Mean CPM ± SE) |
|---|---|---|---|---|
| A | Sham | r30 | 328 ± 102 | 259 ± 111 |
| B | BCG | r30 | 194 ± 52 | 3032 ± 682 |
| C | BCG + r30 | r30 | 774 ± 188 | 5483 ± 1164 |
| D | BCG + rAd/Mtb30 | r30 | 527 ± 137 | 3620 ± 609 |
| E | BCG + Lm Vector | r30 | 544 ± 94 | 2582 ± 454 |
| F | BCG + rLm/Mtb30 | r30 | 1331 ± 249 | 2800 ± 505 |
| G | BCG + rLm/Mtb30 C-O | r30 | 851 ± 155 | 1732 ± 251 |

C. Antibody Responses to Purified Recombinant M. tuberculosis 30 kDa Major Extracellular Protein (r30)

Figure 3:
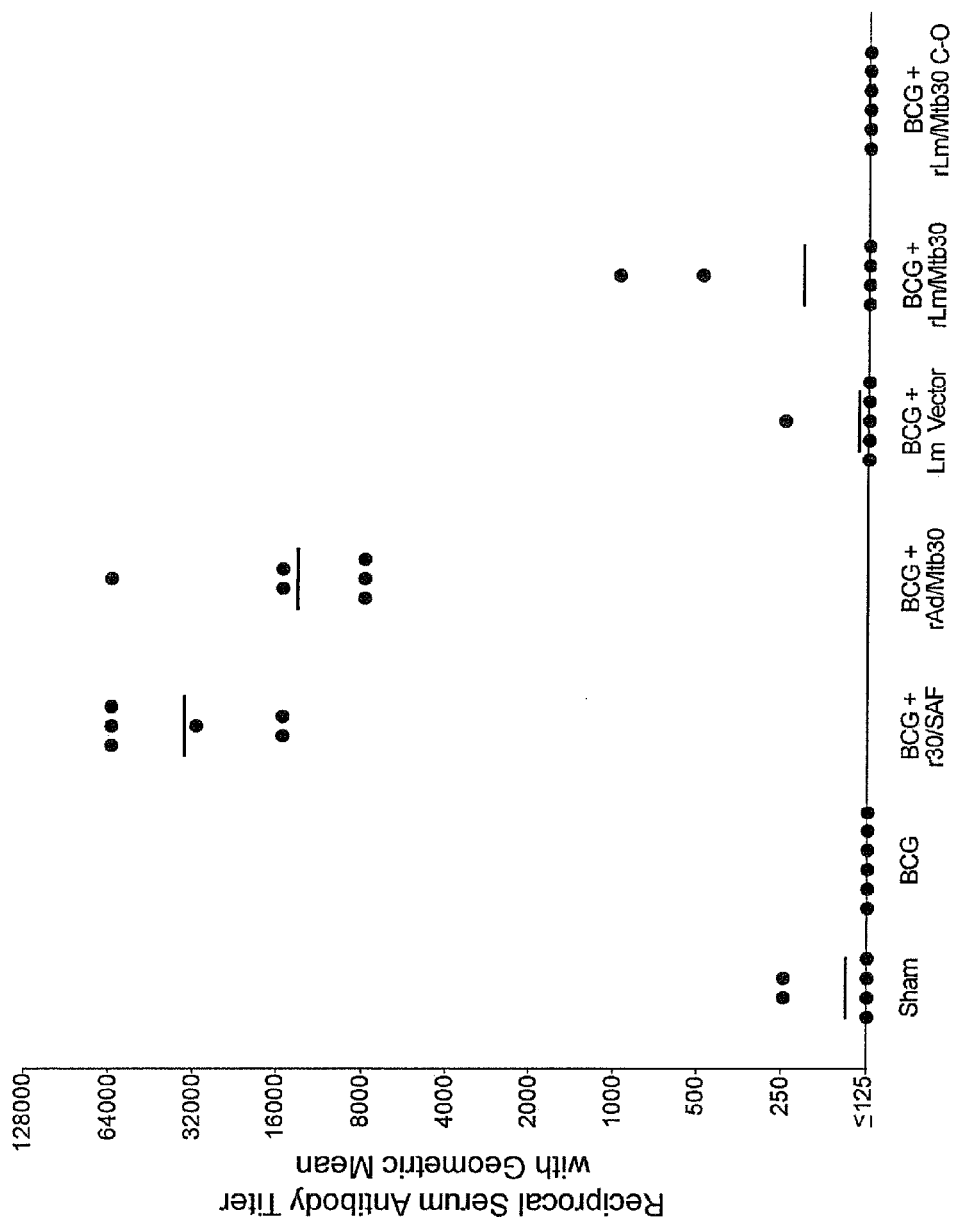
FIG. 3 is a graph illustrating measured reciprocal antibody titer for r30. As described herein under Experiment 1, guinea pigs were first immunized with various vaccines and then assayed for antibody responses to purified recombinant *M. tuberculosis* 30 kDa major extracellular protein.

Immediately after skin-testing, the animals were euthanized and their serum obtained. The serum was tested for antibody to r30 using an ELISA assay. The results are shown in Table 3 and FIG. 3.

TABLE 3

Antibody Titers - Experiment 1

| Group | Vaccination | Test Antigen | Reciprocal Titer (Geometric mean) |
|---|---|---|---|
| A | Sham | r30 | 157 |
| B | BCG | r30 | ≤125 |
| C | BCG + r30 | r30 | 35,919 |
| D | BCG + rAd/Mtb30 | r30 | 14,254 |
| E | BCG + Lm Vector | r30 | 140 |

TABLE 3-continued

Antibody Titers - Experiment 1

| Group | Vaccination | Test Antigen | Reciprocal Titer (Geometric mean) |
|---|---|---|---|
| F | BCG + rLm/Mtb30 | r30 | 223 |
| G | BCG + rLm/Mtb30C-O | r30 | ≤125 |

The results showed that sham-immunized animals and animals immunized only with BCG had negligible antibody titers. In contrast, animals immunized first with BCG and later boosted with r30 in adjuvant or rAd/Mtb30 had high antibody titers. Animals immunized first with BCG and later boosted with rLm/Mtb30 or rLm/Mtb30C—O had low antibody titers, perhaps reflecting the fact that the rLm produces r30 in the cytoplasm of host cells where it is likely processed such that the protein is not available for presentation to B cells.

Experiment 2: Protective Efficacy of rLm/Mtb30 in a Prime-Boost Vaccination Regimen in Guinea Pigs Specific-pathogen free 250-300 g outbred male Hartley strain guinea pigs from Charles River Breeding Laboratories, in groups of 15 (except for the sham group, which had 9 animals), were immunized intradermally as follows:

Group A: Sham
Group B: BCG Tice Parental Control ($10^5$ CFU) at Week 0
Group C: BCG Tice Parental Control ($10^5$ CFU) at Week 0 and 100 µg of r30 in SAF adjuvant at Week 4
Group D: BCG Tice Parental Control ($10^5$ CFU) at Week 0 and 100 µg of r30 in SAF adjuvant at Weeks 4 and 8
Group E: BCG Tice Parental Control ($10^5$ CFU) at Week 0 and rAd/Mtb30 at Week 4
Group F: BCG Tice Parental Control ($10^5$ CFU) at Week 0 and rAd/Mtb30 at Weeks 4 and 8
Group G: BCG Tice Parental Control ($10^5$ CFU) at Week 0 and rLm/Mtb30 at Week 4
Group H: BCG Tice Parental Control ($10^5$ CFU) at Week 0 and rLm/Mtb30 at Weeks 4 and 8

Twenty weeks after immunization, all animals were challenged with an aerosol generated from a 7.5 ml single-cell suspension containing $6.3 \times 10^4$ colony-forming units (CFU) of M. tuberculosis. (Prior to challenge, the challenge strain, M. tuberculosis Erdman strain (ATCC 35801), had been passaged through outbred guinea pigs to maintain virulence, cultured on 7H11 agar, subjected to gentle sonication to obtain a single cell suspension, and frozen at −70° C.). This relatively high dose aerosol dose delivered ~75 live bacilli to the lungs of each animal. The airborne route of infection was used because this is the natural route of infection for pulmonary tuberculosis. A large dose was used so as to induce measurable clinical illness in 100% of control animals within a relatively short time frame (10 weeks). Afterwards, guinea pigs were individually housed in stainless steel cages contained within a laminar flow biohazard safety enclosure and allowed free access to standard laboratory chow and water. The animals were observed for illness and weighed weekly for 10 weeks and then euthanized. The right lung and spleen of each animal was removed and cultured for CFU of M. tuberculosis on Middlebrook 7H11 agar for two weeks at 37° C., 5% $CO_2$-95% air atmosphere. The results were as follows:

A. Deaths

Four of the 9 sham-immunized animals died before the end of the experiment between weeks four and nine after challenge. Two of 15 animals in the group immunized first with BCG and then twice boosted with protein in adjuvant died in the last week of the experiment. All of the animals in the remaining groups survived until the end of the experiment.

B. Net Weight Gain (Loss) After Challenge

Figure 4:
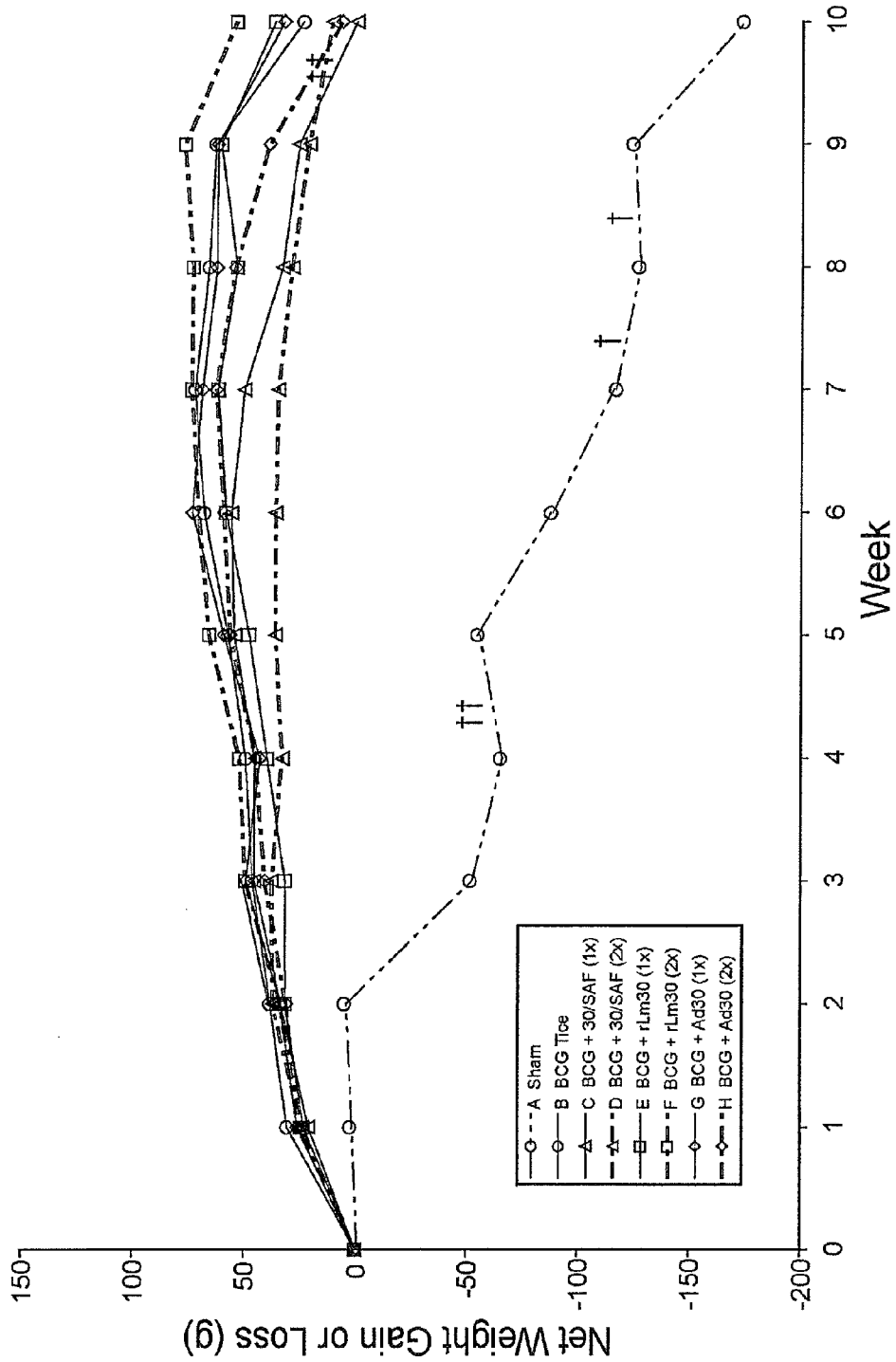
FIG. 4 is a graph illustrating net weight gains or losses of guinea pigs after being challenged with an aerosol generated from a 7.5 ml single-cell suspension containing $6.3 \times 10^4$ colony-forming units (CFU) of *M. tuberculosis*. As described herein under Experiment 2, the guinea pigs were first immunized with various vaccines and then subsequently challenged with the aerosol containing *M. tuberculosis*.

Animals in the sham-immunized group lost weight over the course of the experiment, with a mean net weight loss by the end of the experiment of 173 grams for the surviving animals (FIG. 4). Animals in the remaining groups maintained their weights but did not gain an appreciable amount of weight.

C. Organ Burden

Figure 5:
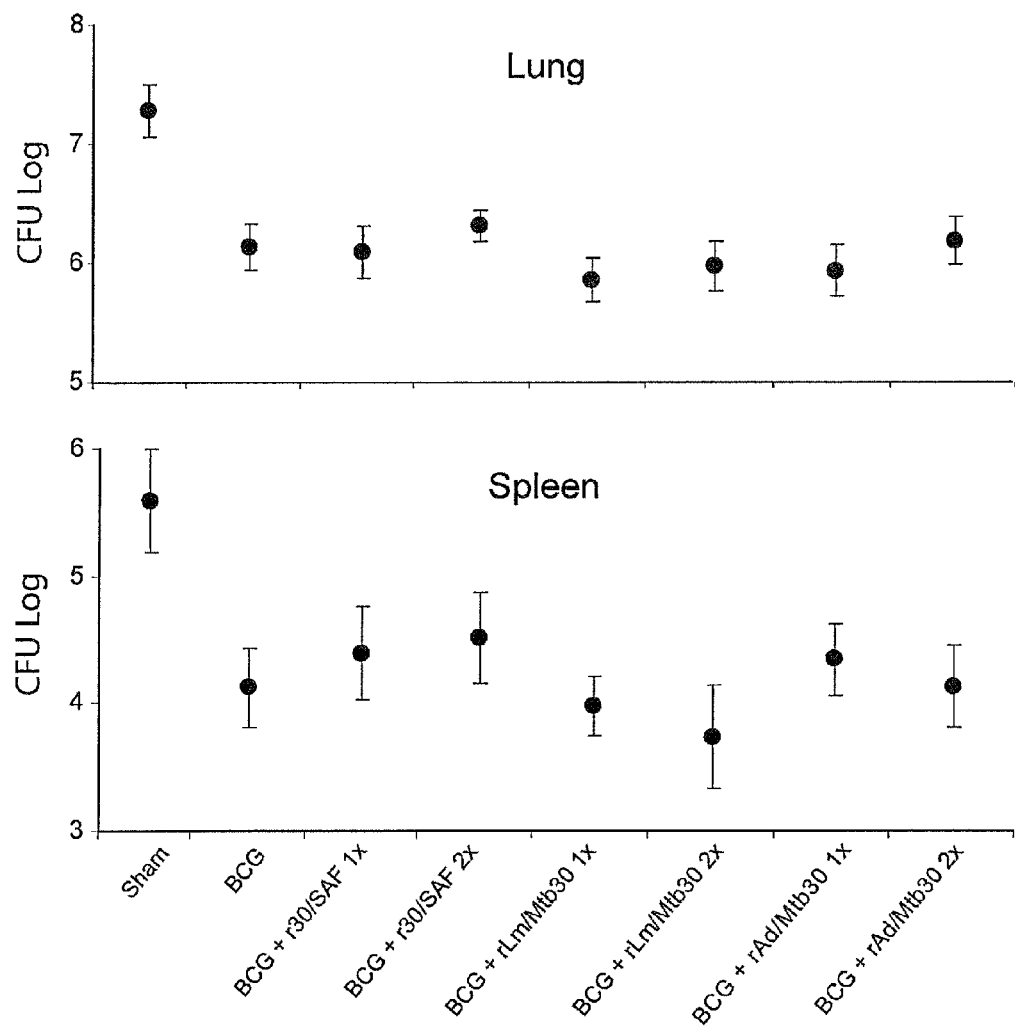
FIG. 5 is a graph illustrating assay measurements (mean log CFU±SE) of colony forming units (CFU) of *M. tuberculosis* in the lungs and spleens of guinea pigs. As described herein under Experiment 2, the guinea pigs were first immunized with various vaccinations and then subsequently challenged with an aerosol generated from a 7.5 ml single-cell suspension containing $6.3 \times 10^4$ colony-forming units (CFU) of *M. tuberculosis*.

The results of the assay for CFU in the lungs and spleens are shown in Table 4 and FIG. 5.

TABLE 4

CFU in Lungs and Spleens - Experiment 2 High Dose Challenge; 20 week immunization-Challenge Interval

| Group | Strain | Lung (Mean Log CFU ± SE) | Spleen (Mean Log CFU ± SE) |
|---|---|---|---|
| A | Sham | 7.28 ± .22 | 5.59 ± 0.41 |
| B | BCG | 6.13 ± .20 | 4.13 ± 0.31 |
| C | BCG + r30 x1 | 6.09 ± .22 | 4.39 ± 0.37 |
| D | BCG + r30 x2 | 6.31 ± .13 | 4.52 ± 0.36 |
| E | BCG + rAd/Mtb30 x 1 | 5.93 ± .22 | 4.34 ± 0.28 |
| F | BCG + rAd/Mtb30 x 2 | 6.18 ± .20 | 4.13 ± 0.32 |
| G | BCG + rLm/Mtb30 x 1 | 5.86 ± .18 | 3.98 ± 0.24 |
| H | BCG + rLm/Mtb30 x 2 | 5.97 ± .21 | 3.73 ± 0.41 |

These results showed that animals immunized with BCG had much lower CFU in the lungs and spleens than the sham immunized animals. Animals immunized first with BCG and then boosted with r30 in adjuvant or rAd/Mtb30 once or twice had similar CFU to BCG immunized animals in this high dose challenge experiment with a 20-week immunization—challenge interval. Animals immunized first with BCG and then boosted with rLm/Mtb30 once or twice had fewer CFU in the lung and spleen than BCG immunized animals in all cases. Animals immunized with BCG and boosted once with rLm/Mtb30 had 0.3 log fewer CFU in the lungs and 0.15 log fewer CFU in the spleen than animals immunized with only BCG. Animals immunized with BCG and boosted twice with rLm/Mtb30 had 0.2 log fewer CFU in the lungs and 0.4 log fewer CFU in the spleen than animals immunized with only BCG.

Thus, in an experiment in which animals were challenged with a relatively high dose of aerosolized M. tuberculosis, such that nearly half of the sham-immunized animals died before the conclusion of the experiment, boosting BCG-immunized animals with rLm/Mtb30 improved protection against M. tuberculosis aerosol challenge.

Experiment 3: Immunogenicity of rLm/Mtb30 in the Mouse Model

Specific-pathogen free 6-8 week male C57BL/6 mice from Charles River Breeding Laboratories, in groups of 4, were immunized intradermally as follows:

Group A: Sham
Group B: BCG Tice Parental Control ($10^6$ CFU) at Week 0
Group C: BCG Tice Parental Control ($10^6$ CFU) at Week 0 and 100 µg of r30 in SAF adjuvant at Weeks 3 and 6
Group D: BCG Tice Parental Control ($10^6$ CFU) at Week 0 and rLm/30(01) (rLmΔactA/LLO-Mtb30) at Weeks 3 and 6

Group E: BCG Tice Parental Control (10⁵ CFU) at Week 0 and rLm/30(03) (rLmΔactAΔinlB/ActA-Mtb30) at Weeks 3 and 6

Group F: BCG Tice Parental Control (10⁵ CFU) at Week 0 and rLm/30(04) (rLmΔactAΔinlB/ActA-Mtb30-SL8) at Weeks 3 and 6

Group G: BCG Tice Parental Control (10⁵ CFU) at Week 0 and rLm/30(07) (rLmΔactAΔinlBΔuvrABprfA*/ActA-Mtb30) at Weeks 3 and 6

Group H: BCG Tice Parental Control (10⁵ CFU) at Week 0 and rLm/Mtb30(08) (rLmΔactAΔinlBΔuvrABprfA*/ActA-Mtb30-SL8) at Weeks 3 and 6

Group I: BCG Tice Parental Control (10⁵ CFU) at Week 0 and rLm/Mtb30(11) (rLmΔactAΔinlB/Mtb30) at Weeks 3 and 6

Group J: BCG Tice Parental Control (10⁵ CFU) at Week 0 and rLm/Mtb30(12) (rLmΔactAΔinlB ΔuvrABprfA*/Mtb30) at Weeks 3 and 6

Group K: BCG Tice Parental Control (105 CFU) at Week 0 and rAd/Mtb30 at Weeks 3 and 6

One week after the last immunization (Week 7), animals were anesthetized with Ketamine/Xylazine, bled and euthanized. Serum was isolated and used to assay for levels of antibodies specific to r30 (see below). In addition, a single cell suspension of splenocytes was prepared for assay of lymphocyte proliferation and intracellular interferon-gamma in response to r30. Red cells were lysed with 1× PharmLyse (BD Biosciences).

Antibody Assay

Serum was analyzed for IgG level by enzyme-linked immunosorbent assay (ELISA). Briefly, 96-well high-binding capacity plates (Corning, N.Y.) were coated or not coated with 0.1 ml of the r30 protein diluted in carbonate/bi-carbonate buffer (50 mM $NaHCO_3$, 50 mM $Na_2CO_3$) to a final concentration of 10 μg/ml. Excess antigen was removed by washing three times with PBS. Sera at a starting dilution of 1:12.5 were diluted further through a two-fold series with PBS. The diluted sera were incubated with r30 coated on 96-well plates at ambient temperature for 3 h. The plates were subsequently incubated for 90 min at ambient temperature with alkaline phosphatase-conjugated goat anti-mouse IgA (Sigma, St. Louis, Mo.) at a dilution of 1:1000. The plates then were washed three times with PBS and 0.05% Tween-20. One hundred μl of p-nitrophenylphosphate substrate in diethanolamine buffer (Phosphatase Substrate kit, BioRad, Hercules, Calif.) was added to each well. The yellow color that developed was read at 414 nm for absorbance using a multiscan microplate reader (TiterTek, Huntsville, Ala.). The endpoint antibody titer was calculated as the reciprocal of the highest serum dilution that was 2 fold or above optical density units in r30 coated wells versus non-coated control wells.

Splenic Lymphocyte Proliferation and Intracellular Cytokine Staining

Splenocytes were incubated with or without r30 antigen and tested for lymphocyte proliferation and intracellular interferon gamma (IFNγ) expression. For the lymphocyte proliferation assay, splenocytes were allowed to proliferate for 48 hours. The amount of lymphocyte proliferation was detected by adding radioactive ³H (tritiated) thymidine for 2 hours, which was incorporated into the newly synthesized DNA of the dividing cells. The amount of radioactivity incorporated into DNA was measured in a scintillation counter and is proportional to the number of proliferating cells, which in turn is a function of the number of lymphocytes that were stimulated by a given antigen to proliferate.

To assay intracellular expression of IFNγ, splenocytes were incubated with or without r30 antigen in the presence of interleukin 2 (IL-2) for 24 hours. Intracellular cytokine staining was performed at day 6 after the last vaccination as described previously (see, e.g. Lee, et al. (2006). "Identification, recombinant expression, immunolocalization in macrophages, and T-cell responsiveness of the major extracellular proteins of Francisella tularensis." Infect Immun 74(7): 4002-13; Jia, et al. (2009). "Recombinant attenuated Listeria monocytogenes vaccine expressing Francisella tularensis IglC induces protection in mice against aerosolized Type A F. tularensis." Vaccine 27(8): 1216-29), using antibodies purchased from BD Biosciences Pharmingen. Briefly, after a 24 h incubation, Golgi-Plug (BD Pharmingen) was added and cells were incubated for an additional 11 h at 37° C. in a 5% $CO_2$ atmosphere. Cells were pelleted at 250×g for 5 min and resuspended in staining buffer (BD Pharmingen) containing Fc-Block (BD Pharmingen). After incubation for 15 min, cells were stained with fluorescein isothiocyanate (FITC)-labeled anti-CD4 or PE-Cy5-labeled anti-CD8 antibody at a 1:100 dilution for 30 min, washed twice in staining buffer, fixed with Cytofix solution for 20 min, and washed twice with Perm/Wash solution. Cells were then stained for intracellular interferon gamma (IFNγ) with PE-labeled rat anti-mouse IFNγ or a PE-labeled isotypic control immunoglobulin G at a dilution of 1:100. All the incubations were performed on ice in the dark. Stained cells were washed, resuspended in staining buffer, and analyzed on a FACSCalibur flow cytometer using CellQuest software.

Results of Experiment 3 (Mouse Expt. TB01)

A. Lymphocyte Proliferation

As shown in FIG. 6A, mice primed with BCG and boosted with rLm/Mtb30 induced higher lymphocyte proliferative response to stimulation by r30 than sham-immunized mice and mice immunized with BCG alone. Among seven rLm/Mtb30 vaccines tested, vaccines derived from the rLmΔactAΔinlBΔuvrABprfA* vector (rLm/Mtb30(12), rLm/Mtb30(07) and rLm/Mtb30(08)) induced stronger immune responses than the corresponding vaccines derived from the rLmΔactAΔinlB vector (rLm/Mtb30(11), rLm/Mtb30(03) and rLm/Mtb30(04)). Mice primed with BCG and boosted with r30 or rAd30 also induced strong lymphocyte proliferation to r30.

B. Serum Antibody Level

Figure 6:
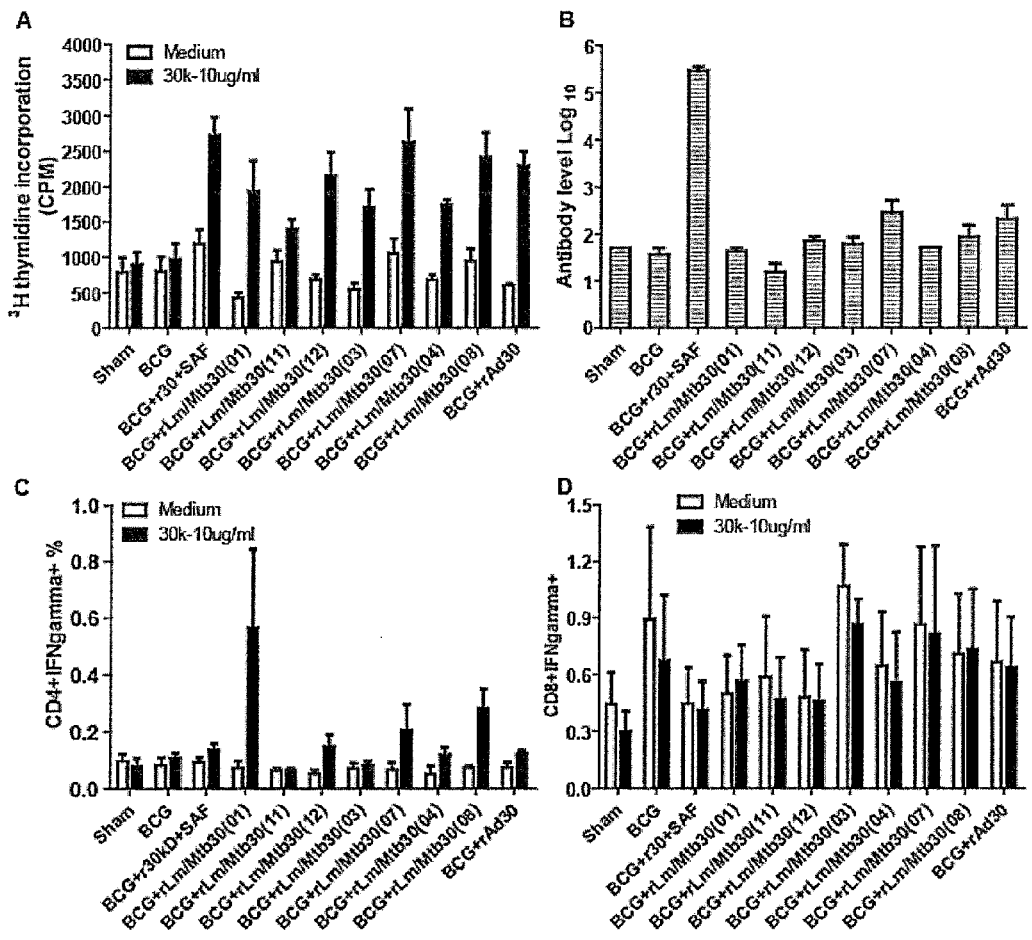
FIG. 6 illustrates cellular and humoral immune responses induced by boosting BCG-immunized animals with rLm/Mtb30 vaccines. Mice in groups of 4 were immunized intradermally with PBS (Sham) or BCG at week 0 and groups of BCG-immunized animals were boosted intradermally with one of various rLm/Mtb30 vaccines, with the rAd30 vaccine, or with r30 in adjuvant at weeks 3 and 6. At week 7, mice were anesthetized, bled and euthanized. Splenocytes were assayed for lymphocyte proliferation (A) or intracellular cytokine (INFgamma) expression in response to r30 (C and D) stratified as to CD4+ or CD8+ cells. Serum was assayed for immunoglobulin-G level in response to the r30 protein (B). Values represent mean±SE.

As shown in FIG. 6 B, mice primed with BCG and boosted with r30+SAF had significantly higher antibody levels than sham-immunized mice and mice primed with BCG and boosted with rLm/Mtb30.

C. Intracellular Expression of IFNγ

Consistent with the lymphocyte proliferation assay results, mice primed with BCG and boosted with rLm/Mtb30 vaccines derived from rLmΔactAΔinlBΔuvrABprfA* vector (rLm/Mtb30(12), rLm/Mtb30(07) and rLm/Mtb30(08)) had stronger CD4+ mediated immune responses than the corresponding vaccines derived from the rLmΔactAΔinlB vector (rLm/Mtb30 (11), rLm/Mtb30(03) and rLm/Mtb30(04)), although the difference did not reach statistical significance (FIG. 6C). There was no significant difference in CD8+ mediated immune responses among mice immunized with BCG alone or primed with BCG and boosted with either rLm/Mtb30 or rAd30 vaccines (FIG. 6D).

Experiment 4: Protective Efficacy of Recombinant Listeria monocytogenes Vaccines Secreting the M. tuberculosis 30 kDa Major Secretory Protein (Antigen 85B) in the Mouse Model of Pulmonary tuberculosis Specific-pathogen free 6-8 week male C57BL/6 mice from Charles River Breeding Laboratories, in groups of 8, were immunized intradermally as follows:
Group A: Sham
Group B: BCG Tice Parental Control ($10^6$ CFU) at Week 0
Group C: BCG Tice Parental Control ($10^6$ CFU) at Week 0 and 100 μg of r30 in SAF adjuvant at Weeks 3 and 6
Group D: BCG Tice Parental Control ($10^6$ CFU) at Week 0 and LmΔactA (Vector control) at Weeks 3 and 6
Group E: BCG Tice Parental Control ($10^6$ CFU) at Week 0 and rLm/30(01) (rLmΔactA/LLO-Mtb30) at Weeks 3 and 6
Group F: BCG Tice Parental Control ($10^5$ CFU) at Week 0 and rLm/Mtb30(12) (rLmΔactAΔinlB ΔuvrABprfA*/Mtb30) at Weeks 3 and 6
Group G: BCG Tice Parental Control ($10^5$ CFU) at Week 0 and rLm/30(07) (rLmΔactAΔinlBΔuvrABprfA*/ActA-Mtb30) at Weeks 3 and 6
Group H: BCG Tice Parental Control ($10^5$ CFU) at Week 0 and rAd/Mtb30 at Weeks 3 and 6

At Week 12, all animals were challenged with an aerosol generated from a 7.5 ml single-cell suspension containing $6.3 \times 10^4$ colony-forming units (CFU) of M. tuberculosis. (Prior to challenge, the challenge strain, M. tuberculosis Erdman strain (ATCC 35801), had been passaged through outbred guinea pigs to maintain virulence, cultured on 7H11 agar, subjected to gentle sonication to obtain a single cell suspension, and frozen at $-70°$ C.). This aerosol dose delivered ~100 live bacilli to the lungs of each animal. The airborne route of infection was used because this is the natural route of infection for pulmonary tuberculosis.

Figure 7:
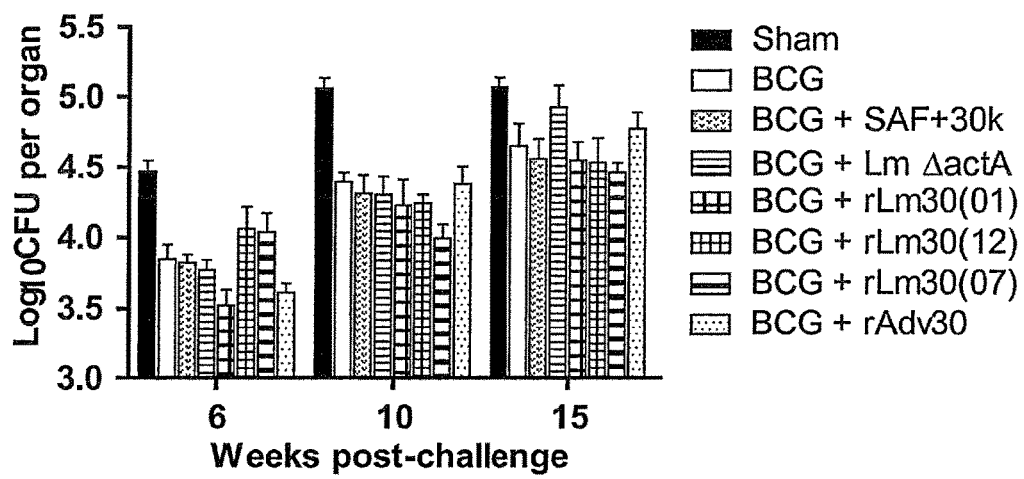
FIG. 7 illustrates assay measurements of colony forming units (CFU) of *M. tuberculosis* in the lungs and spleens of mice. As described herein under Experiment 4, the mice were first immunized with various vaccinations and then subsequently challenged with an aerosol generated from a 7.5 ml single-cell suspension containing $6.3 \times 10^4$ colony-forming units (CFU) of *M. tuberculosis*.
Figure 7:
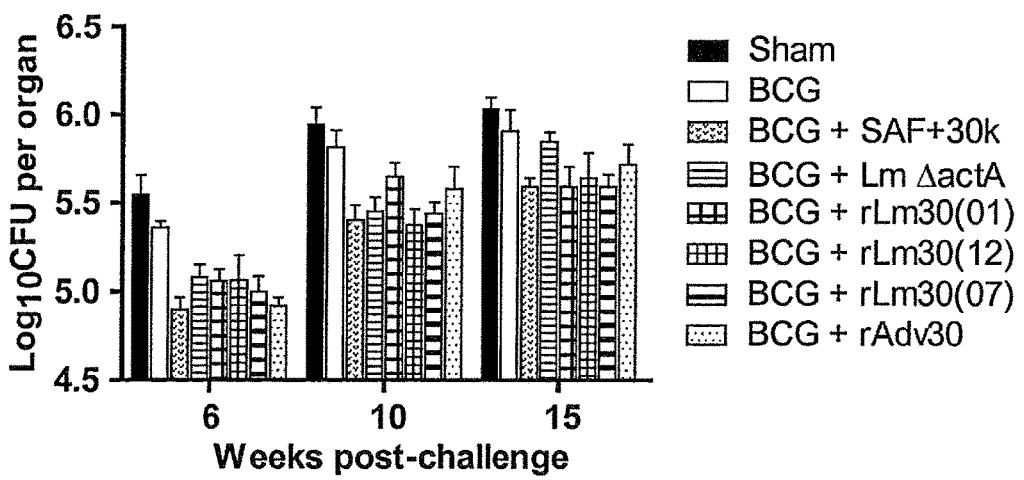

At 6, 10, and 15 weeks after challenge, animals were euthanized. The lung and spleen of each animal was removed and cultured for CFU of M. tuberculosis on Middlebrook 7H11 agar for two weeks at $37°$ C., 5% $CO_2$-95% air atmosphere. The results are shown in FIG. 7.

These results show that animals immunized with BCG had lower CFU in the spleen and somewhat lower CFU in the lungs than the sham immunized animals. Animals immunized first with BCG and then boosted twice with r30 in adjuvant had slightly lower CFU in the spleen than BCG and significantly lower CFU in the lungs than BCG at all time points. Animals immunized first with BCG and then boosted twice with rAd/Mtb30 had lower CFU than BCG in the spleen only at the 6 week time point; at 10 and 15 weeks, these animals had similar CFU in the spleen. In the lung, these mice had lower CFU than BCG at all time points. Animals immunized first with BCG and then boosted twice with the Listeria vector control had CFU counts similar to BCG in the spleen at the 6 and 10 week timepoints and slightly greater but not significantly greater CFU counts in the spleen at 15 weeks. In the lungs, CFU counts were lower than BCG at 6 and 10 weeks, but similar to BCG at 15 weeks.

Results for the listeria vectored vaccines varied somewhat between early and late timepoints. At 6 weeks after challenge, rLm30(01) had significantly fewer CFU counts than BCG in both the spleen and lung. rLm30(12) and rLm30(07) did not have fewer CFU counts than BCG in the spleen but did have fewer CFU counts in the lung. At 10 weeks, all Listeria vectored vaccines were better than BCG in both the lungs and spleen. rLm30(12) was comparable to rLm30(01) in the spleen but had lower CFU counts in the lungs. rLm30(07) gave the lowest counts of all vaccines in the spleen and CFU counts comparable to rLm30(12) in the lungs. At 15 weeks after challenge, all Listeria vectored vaccines had lower CFU counts than the vector control in the lung and spleen; they also had slightly lower CFU counts than BCG in the spleen and moderately lower CFU counts than BCG in the lungs.

Experiment 5: Mouse Immunogenicity of Recombinant Listeria Vaccines

Mice (4 per group) were sham-immunized, immunized with BCG at Week 0, or primed with BCG at Week 0 and then boosted twice at Week 3 and 6 with a) the recombinant 30 kD protein in adjuvant; b) the Lm ΔactA vector, or c) one of five different rLm vaccines expressing the 30 kD protein—rLm30(01), rLm30(03), rLm30(07), rLm30(11), rLm30(12). At Week 10, the mice were euthanized, the spleen removed, a single cell suspension of lymphocytes prepared and used for studies as follows.

A. Interferon-γ Production in Response to M. tuberculosis Antigens

Figure 8:
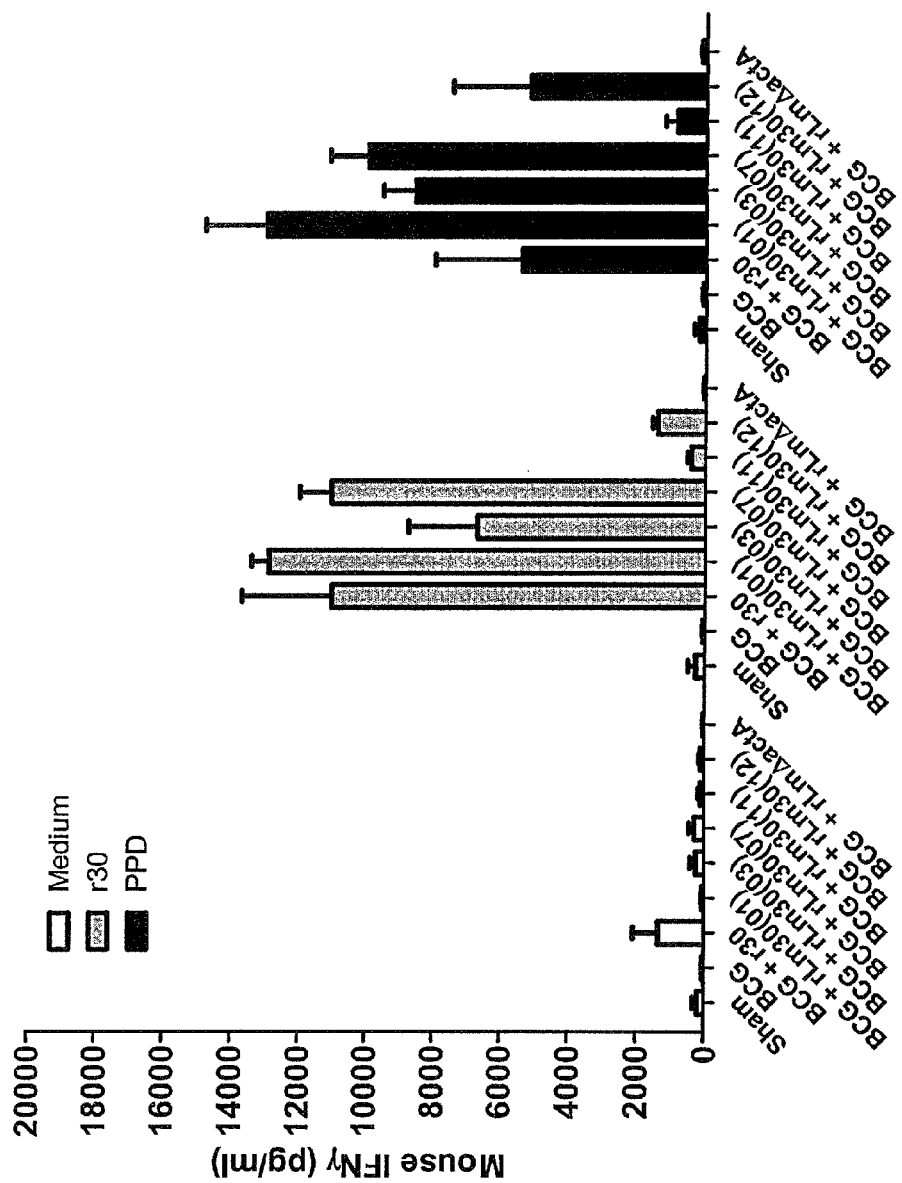
FIG. 8 is a graph illustrating interferon-γ production in mice in response to *M. tuberculosis* antigens. As described herein under Experiment 5, mice were immunized with various vaccines and the splenocytes were stimulated with medium alone, the recombinant 30 kD protein (r30) or *M. tuberculosis* Purified Protein Derivative (PPD) for three days. The splenocyte supernatant fluid was collected and assayed for the level of IFNγ by ELISA.

The splenocytes were stimulated with medium alone, the recombinant 30 kD protein (r30) or M. tuberculosis Purified Protein Derivative (PPD) for three days. The splenocyte supernatant fluid was collected and assayed for the level of IFNγ by ELISA. The results are shown in FIG. 8. Data are the mean±S.E.

In the absence of antigen, essentially no IFNγ was secreted by the splenocytes. In the presence of the purified 30 kDa protein or PPD, splenocytes from sham-immunized mice, mice immunized with only BCG, and mice immunized with BCG and boosted with the Listeria vector control secreted little or no IFNγ. In contrast, splenocytes from mice primed with BCG and boosted with the M. tuberculosis 30 kDA protein or the recombinant Listeria vaccines expressing the M. tuberculosis 30 kDa protein generally produced large amounts of IFNγ.

B. Intracellular Cytokine Secretion

Figure 9:
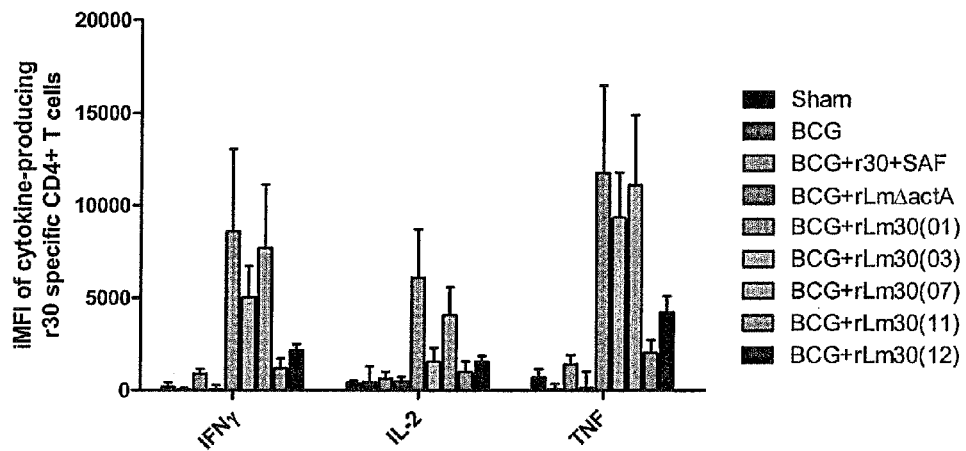
FIG. 9 illustrates the calculated the integrated MFI (iMFI) for cytokine-secreting CD4+ T-cells. As described herein under Experiment 5, mice were immunized with various vaccines and the splenocytes were stimulated with the mature recombinant 30 kD protein (r30) or a pool of three peptides of r30 (30p). The cells were then stained for the cytokines IFNγ, IL-2, and TNFα, and analyzed by multi-parameter flow cytometry.
Figure 9:
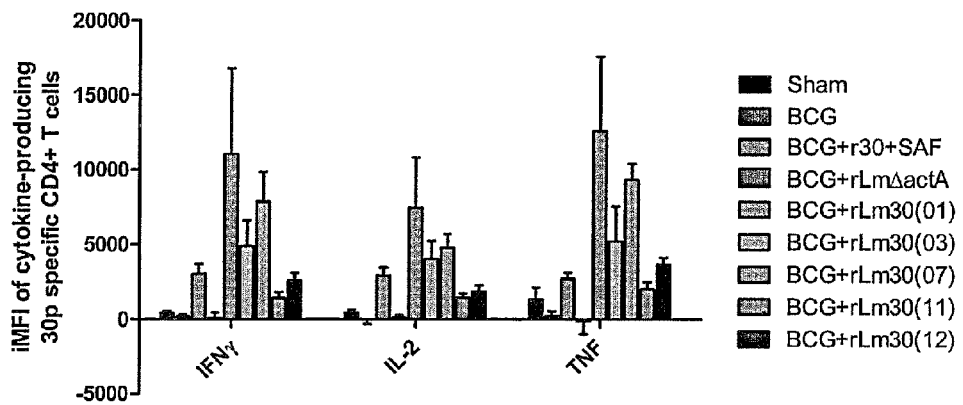

The splenocytes were stimulated with the mature recombinant 30 kD protein (r30) or a pool of three peptides of r30 (30p) for a total of 6 hours (the last 4 hours in the presence of Golgi-Plug), and stained first for CD4 and CD8 and subsequently for the cytokines IFNγ, IL-2, and TNFα, and analyzed by multi-parameter flow cytometry. The total frequency and mean fluorescence intensity (MFI) of each cytokine-secreting CD4+ T-cell was determined and the integrated MFI (iMFI) was calculated. The results are shown in FIG. 9. Data are the mean±S.E. after background subtraction of the identically gated population of cells from the same sample stimulated without antigen.

In the presence of the purified 30 kDa protein (r30) or the 30 kDa protein peptide pool (30p), splenocytes from sham-immunized mice, mice immunized only with BCG, and mice immunized with BCG and boosted with the Listeria vector control displayed low or negligible iMFI. In contrast, splenocytes from mice primed with BCG and boosted with the M. tuberculosis 30 kDA protein or the recombinant Listeria vaccines expressing the M. tuberculosis 30 kDa protein generally displayed moderate to large iMFI. Splenocytes from mice immunized with BCG and boosted with rLm30 (01), rLm30 (03), rLm30 (07), and rLm30 (12) had particularly large iMFI for each of the cytokines This concludes the description of embodiments of the present invention. The foregoing description of one or more embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

Those of skill in this art understand that aspects of this technology can be adapted to form a wide variety of embodiments of the invention. All literature and other references are incorporated herein by reference (e.g. WO 01/46473 and WO 02/094848). Literature describing methods and materials that relate to embodiments of the invention includes Brockstedt et al., (2004) Proc Natl Acad Sci USA 101(38): 13832-7. PMID 15365184; Brockstedt et al., (2005) Nat Med 11(8): 853-60. PMID 16041382; Colditz et al., (1994)." JAMA 271(9): 698-702. PMID 8309034; Fine, P. E. (1989) Rev Infect Dis 11 Suppl 2: 5353-9. PMID 2652252; Harth et al., (1997) Infect Immun 65(6): 2321-8. PMID 9169770; Horwitz et al., (1995) Proc Natl Acad Sci USA 92(5): 1530-4. PMID 7878014; Horwitz et al., (2000) Proc Natl Acad Sci USA 97(25): 13853-8. PMID 11095745; Horwitz et al., (2005) Infect Immun 73(8): 4676-83. PMID 16040980; Jia et al., (2009) Vaccine 27(8): 1216-29. PMID 19126421; Lauer et al., (2008) Infect Immun 76(8): 3742-53. PMID 18541651; Lee et al., (2006) Infect Immun 74(7): 4002-13. PMID 16790773; McShane et al., (2004) Nat Med 10(11): 1240-4. PMID 15502839; Santosuosso et al., (2006) Infect Immun 74(8): 4634-43. PMID 16861651; Vordermeier et al., (2009) Infect Immun 77(8): 3364-73. PMID 19487476; Williams et al., (2005) Infect Immun 73(6): 3814-6. PMID 15908420; Xing et al., (2009) PLoS One 4(6): e5856. PMID 19516906; and Yan et al., (2008) Infect Immun 76(8): 3439-50. PMID 18474644

It is intended that the scope of the invention be limited not by this detailed description, but rather by the claims appended hereto. The above specification, examples and data provide a complete description of the manufacture and use of the apparatus and method of the invention. Since many embodiments of the invention can be made without departing from the scope of the invention, the invention resides in the claims hereinafter appended and the equivalents thereto.

*M. tuberculosis* Polypeptide and Polynucleotide Sequences

TABLE 5

Sequences of *M. tuberculosis* Extracellular Protein Genes

| # | Protein (kDa), (Alternate Names) | Rv numbers/ Initial sequences | Lab/Author | Illustrative References |
|---|---|---|---|---|
| 1 | 12 (fragment of 16 kDa Membrane Protein, alpha crystallian family) MMP | Rv2031c FDTR TABLE 5-continued Sequences of *M. tuberculosis* Extracellular Protein Genes

| | | | |
|---|---|---|---|
| 12 | 71 (hsp/DnaK/ Hsp70) | Rv0350 ARAVG... | R. Young & D. Young Horwitz Lab |
| 13 | 10.4 (EsxH/ ESAT-6 homolog) | Rv0288 | |
| 14 | 14 (alpha crystalline homolog/heat shock protein HSPX) (Tuberculist: 16.2 kDa) | Rv2031c | |
| 15 | 47 (isocitrate lyase/ICL/aceA) | Rv0467 | Mckinney J. D., et al, Nature, 406: 735, 2000 |
| 16 | 7.6 (Hypothetical protein) | Rv2660c | Aaggard C, et al, Nature Medicine, 17: 189, 2011 |
| 17 | 80 (glcB) | Rv1837c TDRVSVGN... | Horwitz Lab |
| 18 | 110 (can) (Tuberculist: 102 kDa) | Rv1475c NSKSVNSFGA... | Horwitz Lab |
| 19 | 9.9 (ESAT-6/esxA) | Rv3875 | |

Note 1:
Proteins 14, 15, and 16 are latency-associated proteins

Note 2:
All sequences now available on-line as a result of the *M. tuberculosis* genome project. See: Cole et al. Nature. *Nature* 393: 537-544, 1998.

Note 3:
See also U.S. Pat. Nos. 7,622,107; 7,300,660; 7,002,002; 6,924,118; 6,818,223; 6,761,894; 6,752,993; 6,599,510; 6,471,967; 6,054,133; 6,013,660; and 5,108,745; and U.S. patent application Nos. 20110129492; 20100284963; 20100183547; and 20100092518, the contents of which are incorporated by reference.

*M. tuberculosis* Protein and coding sequences noted in Table 5 above are provided below. Note: All sequences are from http://genolist.pasteur.fr/TuberculList/.

1. 12 kDa (fragment of 16 kDa membrane protein, alpha crystalline homolog, heat shock protein HSPX, and number 14 in the protein list), 110 aa (SEQ ID NO: 5)
FDTRLMRLEDEMKEGRYEVRAELPGVDPDKDVDIMVRDGQLTIKAERTEQ

KDFDGRSEFAYGSFVRTVSLPVGADEDDIKATYDKGILTVSVAVSEGKPT

EKHIQIRSTN 12 kDa fragment of 16 kDa membrane protein, MMP: 333 bp (SEQ ID NO: 23)
ttcgacacccggttgatgcggctggaagacgagatgaaagaggggcgcta cgaggtacgcgcggagcttcccggggtcgaccccgacaaggacgtcgaca ttatggtccgcgatggtcagctgaccatcaaggccgagcgcaccgagcag aaggacttcgacggtcgctcggaattcgcgtacggttccttcgttcgcac ggtgtcgctgccggtaggtgctgacgaggacgacattaaggccacctacg acaagggcattcttactgtgtcggtggcggtttcggaagggaagccaacc gaaaagcacattcagatccggtccaccaactga 2. *M. tuberculosis* H37Rv|Rv2878c|Mpt53: 173 aa—SOLUBLE SECRETED ANTIGEN MPT53 PRECURSOR. First identified protein sequence starts from ADERL...:

(SEQ ID NO: 6)
MSLRLVSPIKAFADGIVAVAIAVVLMFGLANTPRAVAADERLQFTATTLS

GAPFDGASLQGKPAVLWFWTPWCPFCNAEAPSLSQVAAANPAVTFVGIAT

RADVGAMQSFVSKYNLNFTNLNDADGVIWARYNVPWQPAFVFYRADGTST

FVNNPTAAMSQDELSGRVAALTS

*M. tuberculosis* H37Rv|Rv2878c|mpt53: 522 bp—SOLUBLE SECRETED ANTIGEN MPT53 PRECURSOR (SEQ ID NO: 24)
atgagtcttcgcctggtgtccccgatcaaggcgtttgcggacggcattgt ggccgttgctatcgcggttgtcctgatgttcggtctggccaatacaccgc gagcggtggcagccgatgaacgtctgcagttcaccgcaaccacgctcagc ggtgctcccttcgatggcgcaagcctgcaaggcaagccggcggtgttgtg gttctggacgccgtggtgcccgttctgcaacgcagaagcccccagcctca gccaggtagcggccgctaatccggcggtcaccttcgtcggaatcgccacc cgcgccgacgtcggggcgatgcagagctttgtctcgaagtacaacctgaa tttcaccaacctcaatgacgccgatggtgtgatctgggccgctacaacg tgccttggcaaccggcatttgtgttctatcgcgcggacggcacatcgacg ttcgtcaacaaccccaccgcggccatgtctcaggacgagctgtccggccg ggtggctgcgctgacgtcctgacccggtgaacgaggcgctgatcggtttg -continued
gcgttcgccgccgggttggtggctgcgctgaacccatgcgggtttgccat gttgccggcctacctgctgttggtggtgtatgggcaggattcggcgggcc ggacggggccgcttagcgcagtgggccgagcggcagccgccacggtcggg atggcgctgggcttcttgacgg 3. *M. tuberculosis* H37Rv|Rv1926c|Mpt63: 159 aa—IMMUNOGENIC PROTEIN MPT63 (ANTIGEN MPT63/MPB63) (16 kDa IMMUNOPROTECTIVE EXTRACELLULAR PROTEIN)

(SEQ ID NO: 7)
MKLTTMIKTAVAVVAMAAIATFAAPVALAAYPITGKLGSELTMTDTVGQV

VLGWKVSDLKSSTAVIPGYPVAGQVWEATATVNAIRGSVTPAVSQFNART

ADGINYRVLWQAAGPDTISGATIPQGEQSTGKIYFDVTGPSPTIVAMNNG

MEDLLIWEP

*M. tuberculosis* H37Rv|Rv1926c|mpt63: 480 bp-IMMUNOGENIC PROTEIN MPT63 (ANTIGEN MPT63/MPB63) (16 kDa IMMUNOPROTECTIVE EXTRACELLULAR PROTEIN)

(SEQ ID NO: 25)

atgaagctcaccacaatgatcaagacggcagtagcggtcgtggccatggc ggccatcgcgacctttgcggcaccggtcgcgttggctgcctatcccatca ccggaaaacttggcagtgagctaacgatgaccgacaccgttggccaagtc gtgctcggctggaaggtcagtgatctcaaatccagcacggcagtcatccc cggctatccggtggccggccaggtctgggaggccactgccacggtcaatg cgattcgcggcagcgtcacgcccgcggtctcgcagttcaatgcccgcacc gccgacggcatcaactaccgggtgctgtggcaagccgcgggccccgacac cattagcggagccactatcccccaaggcgaacaatcgaccggcaaaatct acttcgatgtcaccggcccatcgccaaccatcgtcgcgatgaacaacggc atggaggatctgctgatttgggagccgtag 4. *M. tuberculosis* H37Rv|Rv3846|SodA: 207 aa—SUPEROXIDE DISMUTASE (FE) SODA (SEQ ID NO: 8)

VAEYTLPDLDWDYGALEPHISGQINELHHSKHHATYVKGANDAVAKLEEA

RAKEDHSAILLNEKNLAFNLAGHVNHTIWWKNLSPNGGDKPTGELAAAIA

DAFGSFDKFRAQFHAAATTVQGSGWAALGWDTLGNKLLIFQVYDHQTNFP

LGIVPLLLLDMWEHAFYLQYKNVKVDFAKAFWNVVNWADVQSRYAAATSQ

TKGLIFG

*M. tuberculosis* H37Rv|Rv3846|sodA: 624 bp—SUPEROXIDE DISMUTASE (FE) SODA (SEQ ID NO: 26)

gtggccgaatacaccttgccagacctggactgggactacggagcactgga accgcacatctcgggtcagatcaacgagcttcaccacagcaagcaccacg ccacctacgtaaagggcgccaatgacgccgtcgccaaactcgaagaggcg cgcgccaaggaagatcactcagcgatcttgctgaacgaaaagaatctagc -continued tttcaacctcgccggccacgtcaatcacaccatctggtggaagaacctgt cgcctaacggtggtgacaagcccaccggcgaactcgccgcagccatcgcc gacgcgttcggttcgttcgacaagttccgtgcgcagttccacgcggccgc taccaccgtgcaggggtcgggctgggcggcactgggctgggacacactcg gcaacaagctgctgatattccaggtttacgaccaccagacgaacttcccg ctaggcattgttccgctgctgctgctcgacatgtgggaacacgccttcta cctgcagtacaagaacgtcaaagtcgactttgccaaggcgttttggaacg tcgtgaactgggccgatgtgcagtcacggtatgcggccgcgacctcgcag accaaggggttgatattcggctga 5. *M. tuberculosis* H37Rv|Rv1980c|Mpt64: 228 aa—IMMUNOGENIC PROTEIN MPT64 (ANTIGEN MPT64/MPB64)

(SEQ ID NO: 9)

VRIKIFMLVTAVVLLCCSGVATAAPKTYCEELKGTDTGQACQIQMSDPAY

NINISLPSYYPDQKSLENYIAQTRDKFLSAATSSTPREAPYELNITSATY

QSAIPPRGTQAVVLKVYQNAGGTHPTTTYKAFDWDQAYRKPITYDTLWQA

DTDPLPVVFPIVQGELSKQTGQQVSIAPNAGLDPVNYQNFAVTNDGVIFF

FNPGELLPEAAGPTQVLVPRSAIDSMLA

*M. tuberculosis* H37Rv|Rv1980c|mpt64: 687 bp—IMMUNOGENIC PROTEIN MPT64 (ANTIGEN MPT64/MPB64)

(SEQ ID NO: 27)

gtgcgcatcaagatcttcatgctggtcacggctgtcgttttgctctgttg ttcgggtgtggccacggccgcgcccaagacctactgcgaggagttgaaag gcaccgataccggccaggcgtgccagattcaaatgtccgacccggcctac aacatcaacatcagcctgcccagttactaccccgaccagaagtcgctgga aaattacatcgcccagacgcgcgacaagttcctcagcgcggccacatcgt ccactccacgcgaagccccctacgaattgaatatcacctcggccacatac cagtccgcgataccgccgcgtggtacgcaggccgtggtgctcaaggtcta ccagaacgccggcggcacgcacccaacgaccacgtacaaggccttcgatt gggaccaggcctatcgcaagccaatcacctatgacacgctgtggcaggct gacaccgatccgctgccagtcgtcttccccattgtgcaaggtgaactgag caagcagaccggacaacaggtatcgatagcgccgaatgccggcttggacc cggtgaattatcagaacttcgcagtcacgaacgacggggtgattttcttc ttcaacccgggggagttgctgcccgaagcagccggcccaacccaggtatt ggtcccacgttccgcgatcgactcgatgctggcctag 6. *M. tuberculosis* H37Rv|Rv3803c|FbpD: 299 aa—SECRETED MPT51/MPB51 ANTIGEN PROTEIN FBPD (MPT51/MPB51 ANTIGEN 85 COMPLEX C) (AG58C) (MYCOLYL TRANSFERASE 85C) (FIBRONECTIN-BINDING PROTEIN C) (85C)

(SEQ ID NO: 10)
MKGRSALLRALWIAALSFGLGGVAVAAEPTAKAAPYENLMVPSPSMGRDI
PVAFLAGGPHAVYLLDAFNAGPDVSNWVTAGNAMNTLAGKGISVVAPAGG
AYSMYTNWEQDGSKQWDTFLSAELPDWLAANRGLAPGGHAAVGAAQGGYG
AMALAAFHPDRFGFAGSMSGFLYPSNTTTNGAIAAGMQQFGGVDTNGMWG
APQLGRWKWHDPWVHASLLAQNNTRVWVWSPTNPGASDPAAMIGQAAEAM
GNSRMFYNQYRSVGGHNGHFDFPASGDNGWGSWAPQLGAMSGDIVGAIR (SEQ ID NO: 28)
atgaagggtcggtcggcgctgctgcgggcgctctggattgccgcactgtc
attcgggttgggcggtgtcgcggtagccgcggaacccaccgccaaggccg
ccccatacgagaacctgatggtgccgtcgcctcgatgggccgggacatc
ccggtggccttcctagccggtgggccgcacgcggtgtatctgctggacgc
cttcaacgccggcccggatgtcagtaactgggtcaccgcgggtaacgcga
tgaacacgttggcgggcaaggggatttcggtggtggcaccggccggtggt
gcgtacagcatgtacaccaactgggagcaggatggcagcaagcagtggga
caccttcttgtccgctgagctgcccgactggctggccgctaaccggggct
ggccccggtggccatgcggccgttggcgccgctcagggcggttacggg
gcgatgcgctggcggccttccaccccgaccgcttcggcttcgctggctc
gatgtcgggctttttgtaccccgtcgaacaccaccaccaacggtgcgatcg
cggcgggcatgcagcaattcggcggtgtggacaccaacggaatgtgggga
gcaccacagctgggtcggtggaagtggcacgacccgtgggtgcatgccag
cctgctggcgcaaaacaacacccgggtgtgggtgtggagcccgaccaacc
cgggagccagcgatcccgccgccatgatcggccaagccgccgaggcgatg
ggtaacagccgcatgttctacaaccagtatcgcagcgtcggcgggcacaa
cggacacttcgacttcccagccagcggtgacaacggctggggctcgtggg
cgccccagctgggcgctatgtcgggcgatatcgtcggtgcgatccgctaa 7. *M. tuberculosis* H37Rv|Rv1886c|FbpB: 325 aa—SECRETED ANTIGEN 85-B FBPB (85B) (ANTIGEN 85 COMPLEX B) (MYCOLYL TRANSFERASE 85B) (FIBRONECTIN-BINDING PROTEIN B) (EXTRACELLULAR ALPHA-ANTIGEN)

(SEQ ID NO: 4)
MTDVSRKIRAWGRRLMIGTAAAVVLPGLVGLAGGAATAGAFSRPGLPVEY
LQVPSPSMGRDIKVQFQSGGNNSPAVYLLDGLRAQDDYNGWDINTPAFEW
YYQSGLSIVMPVGGQSSFYSDWYSPACGKAGCQTYKWETFLTSELPQWLS
ANRAVKPTGSAAIGLSMAGSSAMILAAYHPQQFIYAGSLSALLDPSQGMG
PSLIGLAMGDAGGYKAADMWGPSSDPAWERNDPTQQIPKLVANNTRLWVY
CGNGTPNELGGANIPAEFLENFVRSSNLKFQDAYNAAGGHNAVFNFPPNG
THSWEYWGAQLNAMKGDLQSSLGAG (SEQ ID NO: 29)
atgacagacgtgagccgaaagattcgagcttggggacgccgattgatgat
cggcacggcagcggctgtagtccttccgggcctggtggggcttgccggcg
gagcggcaaccgcgggcgcgttctcccggccggggctgccggtcgagtac
ctgcaggtgccgtcgccgtcgatgggccgcgacatcaaggttcagttcca
gagcggtgggaacaactcacctgcggtttatctgctcgacggcctgcgcg
cccaagacgactacaacggctgggatatcaacaccccggcgttcgagtgg
tactaccagtcgggactgtcgatagtcatgccggtcggcgggcagtccag
cttctacagcgactggtacagcccggcctgcggtaaggctggctgccaga
cttacaagtgggaaaccttcctgaccagcgagctgccgcaatggttgtcc
gccaacagggccgtgaagcccaccggcagcgctgcaatcggcttgtcgat
ggccggctcgtcggcaatgatcttggccgcctaccaccccagcagttca
tctacgccggctcgctgtcggccctgctggaccctctcaggggatgggg
cctagcctgatcggcctcgcgatgggtgacgccggcggttacaaggccgc
agacatgtgggtccctcgagtgacccggcatgggagcgcaacgaccta
cgcagcagatcccaagctggtcgcaaacaacacccggctatgggttat
tgcgggaacggcacccccgaacgagttgggcggtgccaacatacccgccga
gttcttggagaacttcgttcgtagcagcaacctgaagttccaggatgcgt
acaacgccgcgggcgggcacaacgccgtgttcaacttcccgcccaacggc
acgcacagctgggagtactggggcgctcagctcaacgccatgaagggtga
cctgcagagttcgttaggcgccggctga 8. *M. tuberculosis* H37Rv|Rv3804c|FbpA: 338 aa—SECRETED ANTIGEN 85-A FBPA (MYCOLYL TRANSFERASE 85A) (FIBRONECTIN-BINDING PROTEIN A) (ANTIGEN 85 COMPLEX A)

(SEQ ID NO: 11)
MQLVDRVRGAVTGMSRRLVVGAVGAALVSGLVGAVGGTATAGAFSRPGLP
VEYLQVPSPSMGRDIKVQFQSGGANSPALYLLDGLRAQDDFSGWDINTPA
FEWYDQSGLSVVMPVGGQSSFYSDWYQPACGKAGCQTYKWETFLTSELPG
WLQANRHVKPTGSAVVGLSMAASSALTLAIYHPQQFVYAGAMSGLLDPSQ
AMGPTLIGLAMGDAGGYKASDMWGPKEDPAWQRNDPLLNVGKLIANNTRV
WVYCGNGKPSDLGGNNLPAKFLEGFVRTSNIKFQDAYNAGGGHNGVFDFP
DSGTHSWEYWGAQLNAMKPDLQRALGATPNTGPAPQGA (SEQ ID NO: 30)
atgcagcttgttgacagggttcgtggcgccgtcacgggtatgtcgcgtcg
actcgtggtcggggccgtcggcgcggccctagtgtcgggtctggtcggcg
ccgtcggtggcacggcgaccgcggggcatttcccggccgggcttgccg
gtgagtacctgcaggtgccgtcgccgtcgatgggccgtgacatcaaggt
ccaattccaaagtggtggtgccaactcgcccgccctgtacctgctcgacg

```
gcctgcgcgcgcaggacgacttcagcggctgggacatcaacaccccggcg ttcgagtggtacgaccagtcgggcctgtcggtggtcatgccggtgggtgg ccagtcaagcttctactccgactggtaccagcccgcctgcggcaaggccg gttgccagacttacaagtgggagaccttcctgaccagcgagctgccgggg tggctgcaggccaacaggcacgtcaagcccaccggaagcgccgtcgtcgg tctttcgatggctgcttcttcggcgctgacgctggcgatctataccccc agcagttcgtctacgcgggagcgatgtcgggcctgttggaccccccag gcgatgggtcccaccctgatcggcctggcgatgggtgacgctggcggcta caaggcctccgacatgtgggcccgaaggaggacccggcgtggcagcgca acgacccgctgttgaacgtcgggaagctgatcgccaacaacaccccgtc tgggtgtactgcggcaacggcaagccgtcggatctgggtggcaacaacct gccggccaagttcctcgagggcttcgtgcggaccagcaacatcaagttcc aagacgcctacaacgccggtggcggccacaacggcgtgttcgacttcccg gacagcggtacgcacagctgggagtactggggcgcgcagctcaacgctat gaagcccgacctgcaacgggcactgggtgccacgccaacaccgggcccg cgccccagggcgcctag
```

9. *M. tuberculosis* H37Rv|Rv0983|PepD: 464 aa—PROBABLE SERINE PROTEASE PEPD (SERINE PROTEINASE) (MTB32B)

(SEQ ID NO: 12)
MAKLARVVGLVQEEQPSDMTNHPRYSPPPQQPGTPGYAQGQQQTYSQQFD

WRYPPSPPPQPTQYRQPYEALGGTRPGLIPGVIPTMTPPPGMVRQRPRAG

MLAIGAVTIAVVSAGIGGAAASLVGFNRAPAGPSGGPVAASAAPSIPAAN

MPPGSVEQVAAKVVPSVVMLETDLGRQSEEGSGIILSAEGLILTNNHVIA

AAAKPPLGSPPPKTTVTFSDGRTAPFTVVGADPTSDIAVVRVQGVSGLTP

ISLGSSSDLRVGQPVLAIGSPLGLEGTVTTGIVSALNRPVSTTGEAGNQN

TVLDAIQTDAAINPGNSGGALVNMNAQLVGVNSAIATLGADSADAQSGSI

GLGFAIPVDQAKRIADELISTGKASHASLGVQVTNDKDTLGAKIVEVVAG

GAAANAGVPKGVVVTKVDDRPINSADALVAAVRSKAPGATVALTFQDPSG

GSRTVQVTLGKAEQ

*M. tuberculosis* H37Rv|Rv0983|pepD: 1395 bp—PROBABLE SERINE PROTEASE PEPD (SERINE PROTEINASE) (MTB32B)

(SEQ ID NO: 31)
```
atggccaagttggcccgagtagtgggcctagtacaggaagagcaacctag cgacatgacgaatcacccacggtattcgccaccgccgcagcagccgggaa ccccaggttatgctcaggggcagcagcaaacgtacagccagcagttcgac tggcgttaccaccgtccccgccccgcagccaacccagtaccgtcaacc ctacgaggcgttgggtggtacccgccgggtctgatacctggcgtgattc cgaccatgacgccccctcctgggatggttcgccaacgcctcgtgcaggc atgttggccatcggcgcggtgacgatagcggtggtgtccgccggcatcgg cggcgcggccgcatccctggtcgggttcaaccgggcacccgccgcccca
```

```
gcggcggcccagtggctgccagcgcggcgccaagcatcccgcagcaaac atgccgccggggtcggtcgaacaggtggcggccaaggtggtgcccagtgt cgtcatgttggaaaccgatctgggccgccagtcggaggagggctccggca tcattctgtctgccgaggggctgatcttgaccaacaaccacgtgatcgcg gcggccgccaagcctcccctgggcagtccgccgccgaaaacgacggtaac cttctctgacgggcggaccgcaccttcacggtggtgggggctgaccca ccagtgatatcgccgtcgtccgtgttcagggcgtctcc
```

10. *M. tuberculosis* H37Rv|Rv1860|Apa: 325 aa—ALANINE AND PROLINE RICH SECRETED PROTEIN APA (FIBRONECTIN ATTACHMENT PROTEIN) (Immunogenic protein MPT32) (Antigen MPT-32) (45-kDa glycoprotein) (45/47 kDa antigen)

(SEQ ID NO: 13)
MHQVDPNLTRRKGRLAALAIAAMASASLVTVAVPATANADPEPAPPVPTT

AASPPSTAAAPPAPATPVAPPPPAAANTPNAQPGDPNAAPPPADPNAPPP

PVIAPNAPQPVRIDNPVGGFSFALPAGWVESDAAHFDYGSALLSKTTGDP

PFPGQPPPVANDTRIVLGRLDQKLYASAEATDSKAAARLGSDMGEFYMPY

PGTRINQETVSLDANGVSGSASYYEVKFSDPSKPNGQIWTGVIGSPAANA

PDAGPPQRWFVVWLGTANNPVDKGAAKALAESIRPLVAPPPAPAPAPAEP

APAPAPAGEVAPTPTTPTPQRTLPA

*M. tuberculosis* H37Rv|Rv1860|apa: 978 bp—ALANINE AND PROLINE RICH SECRETED PROTEIN APA (FIBRONECTIN ATTACHMENT PROTEIN) (Immunogenic protein MPT32) (Antigen MPT-32) (45/47 kDa glycoprotein)

(SEQ ID NO: 32)
```
atgcatcaggtggaccccaacttgacacgtcgcaagggacgattggcggc actggctatcccggcgatggccagcgccagcctggtgaccgttgcggtgc ccgcgaccgccaacgccgatccggagccagcgccccggtacccacaacg gccgcctcgccgccgtcgaccgctgcagcgccacccgcaccggcgacacc tgtttgccccccaccaccggccgccgccaacacgccgaatgcccagccgg gcgatcccaacgcagccactccgccgccgacccgaacgcaccgccgcca cctgtcattgccccaaacgcaccccaacctgtccggatcgacaacccggt tggaggattcagcttcgcgctgcctgctggctgggtggagtctgacgccg cccacttcgactacggttcagcactcctcaccaaaaccaccggggacccg ccatttcccggacagccgccgccggtggccaatgacacccgtatcgtgct cggccggctagaccaaaagctttacgccagcgccgaagccaccgactcca aggccgcggcccggtttgggctcggacatcggtgagttctatatgccctac ccgggcacccggatcaaccaggaaaccgtctcgctcgacgccaacgggt gtctggaagcgcgtcgtattacgaagtcaagttcagcgatccgagtaagc cgaacggccagatctggacgggcgtaatcggctcgcccggcgaacgca ccggacgccggggccccctcagcgctggtttgtggtatggctcgggaccgc caacaacccggtggacaagggcgcggccaaggcgctggccgaatcgatcc
```

```
ggcctttggtcgccccgccgccggcgccggcaccggctcctgcagagccc gctccggcgccggcgccggccggggaagtcgctcctaccccgacgacacc gacaccgcagcggaccttaccggcctga
```

11. *M. tuberculosis* H37Rv|Rv2220|GlnA1: 478 aa—GLUTAMINE SYNTHETASE GLNA1 (GLUTAMINE SYNTHASE) (GS-I)

(SEQ ID NO: 14)
```
VTEKTPDDVFKLAKDEKVEYVDVRFCDLPGIMQHFTIPASAFDKSVFDDG

LAFDGSSIRGFQSIHESDMLLLPDPETARIDPFRAAKTLNINFFVHDPFT

LEPYSRDPRNIARKAENYLISTGIADTAYFGAEAEFYIFDSVSFDSRANG

SFYEVDAISGWWNTGAATEADGSPNRGYKVRHKGGYFPVAPNDQYVDLRD

KMLTNLINSGFILEKGHHEVGSGGQAEINYQFNSLLHAADDMQLYKYIIK

NTAWQNGKTVTFMPKPLFGDNGSGMHCHQSLWKDGAPLMYDETGYAGLSD

TARHYIGGLLHHAPSLLAFTNPTVNSYKRLVPGYEAPINLVYSQRNRSAC

VRIPITGSNPKAKRLEFRSPDSSGNPYLAFSAMLMAGLDGIKNKIEPQAP

VDKDLYELPPEEAASIPQTPTQLSDVIDRLEADHEYLTEGGVFTNDLIET

WISFKRENEIEPVNIRPHPYEFALYYDV
```

*M. tuberculosis* H37Rv|Rv2220|glnA1: 1437 bp—GLUTAMINE SYNTHETASE GLNA1 (GLUTAMINE SYNTHASE) (GS-I)

(SEQ ID NO: 33)
```
gtgacggaaaagacgcccgacgacgtcttcaaacttgccaaggacgagaa ggtcgaatatgtcgacgtccggttctgtgacctgcctggcatcatgcagc acttcacgattccggcttcggcctttgacaagagcgtgtttgacgacggc ttggccttttgacggctcgtcgattcgcgggttccagtcgatccacgaatc cgacatgttgcttcttcccgatcccgagacggcgcgcatcgacccgttcc gcgcggccaagacgctgaatatcaacttcttttgtgcacgacccgttcacc ctggagccgtactcccgcgacccgcgcaacatcgcccgcaaggccgagaa ctacctgatcagcactggcatcgccgacaccgcatacttcggcgccgagg ccgagttctacattttcgattcggtgagcttcgactcgcgcgccaacggc tccttctacgaggtggacgccatctcggggtggtggaacaccggcgcggc gaccgaggccgacggcagtcccaaccggggctacaaggtccgccacaagg gcgggtatttcccagtggccccaacgaccaatacgtcgacctgcgcgac aagatgctgaccaacctgatcaactccggcttcatcctggagaagggcca ccacgaggtgggcagcggcggacaggccgagatcaactaccagttcaatt cgctgctgcacgccgccgacgacatgcagttgtacaagtacatcatcaag aacaccgcctggcagaacggcaaaacggtcacgttcatgcccaagccgct gttcggcgacaacgggtccggcatgcactgtcatcagtcgctgtggaagg acggggcccgctgatgtacgacgagacgggttatgccggtctgtcggac acggcccgtcattacatcggcggcctgttacaccacgccgcgtcgctgct
```

```
ggccttcaccaacccgacggtgaactcctacaagcggctggttccggtt acgaggcccccgatcaacctggtctatagccagcgcaaccggtcggcatgc gtgcgcatcccgatcaccggcagcaacccgaaggccaagcggctggagtt ccgaagccccgactcgtcgggcaacccgtatctggcgttctcggccatgc tgatggcaggcctggacggtatcaagaacaagatcgagccgcaggcgccc gtcgacaaggatctctacgagctgccgccggaagaggccgcgagtatccc gcagactccgacccagctgtcagatgtgatcgaccgtctcgaggccgacc acgaatacctcaccgaaggaggggtgttcacaaacgacctgatcgagacg tggatcagtttcaagcgcgaaaacgagatcgagccggtcaacatccggcc gcatccctacgaattcgcgctgtactacgacgtttaa
```

12. *M. tuberculosis* H37Rv|Rv0350|DnaK: 625 aa—PROBABLE CHAPERONE PROTEIN DNAK (HEAT SHOCK PROTEIN 70) (HEAT SHOCK 70 KDA PROTEIN) (HSP70)

(SEQ ID NO: 15)
```
MARAVGIDLGTTNSVVSVLEGGDPVVVANSEGSRTTPSIVAFARNGEVLV

GQPAKNQAVTNVDRTVRSVKRHMGSDWSIEIDGKKYTAPEISARILMKLK

RDAEAYLGEDITDAVITTPAYFNDAQRQATKDAGQIAGLNVLRIVNEPTA

AALAYGLDKGEKEQRILVFDLGGGTFDVSLLEIGEGVVEVRATSGDNHLG

GDDWDQRVVDWLVDKFKGTSGIDLTKDKMAMQRLREAAEKAKIELSSSQS

TSINLPYITVDADKNPLFLDEQLTRAEFQRITQDLLDRTRKPFQSVIADT

GISVSEIDHVVLVGGSTRMPAVTDLVKELTGGKEPNKGVNPDEVVAVGAA

LQAGVLKGEVKDVLLLDVTPLSLGIETKGGVMTRLIERNTTIPTKRSETF

TTADDNQPSVQIQVYQGEREIAAHNKLLGSFELTGIPPAPRGIPQIEVTF

DIDANGIVHVTAKDKGTGKENTIRIQEGSGLSKEDIDRMIKDAEAHAEED

RKRREEADVRNQAETLVYQTEKFVKEQREAEGGSKVPEDTLNKVDAAVAE

AKAALGGSDISAIKSAMEKLGQESQALGQAIYEAAQAASQATGAAHPGGE

PGGAHPGSADDVVDAEVVDDGREAK
```

*M. tuberculosis* H37Rv|Rv0350|dnaK: 1878 bp—PROBABLE CHAPERONE PROTEIN DNAK (HEAT SHOCK PROTEIN 70) (HEAT SHOCK 70 KDA PROTEIN) (HSP70)

(SEQ ID NO: 34)
```
atggctcgtgcggtcgggatcgacctcgggaccaccaactccgtcgtctc ggttctggaaggtggcgacccggtcgtcgtcgccaactccgagggctcca ggaccacccgtcaattgtcgcgttcgcccgcaacggtgaggtgctggtc ggccagcccgccaagaaccaggcagtgaccaacgtcgatcgcaccgtgcg ctcggtcaagcgacacatgggcagcgactggtccatagagattgacggca agaaatacaccgcgccggagatcagcgcccgcattctgatgaagctgaag cgcgacgccgaggcctacctcggtgaggacattaccgacgcggttatcac gacgcccgcctacttcaatgacgcccagcgtcaggccaccaaggacgccg
```

-continued gccagatcgccggcctcaacgtgctgcggatcgtcaacgagccgaccgcg gccgcgctggcctacggcctcgacaagggcgagaaggagcagcgaatcct ggtcttcgacttgggtggtggcactttcgacgtttccctgctggagatcg gcgagggtgtggttgaggtccgtgccacttcgggtgacaaccacctcggc ggcgacgactgggaccagcgggtcgtcgattggctggtggacaagttcaa gggcaccagcggcatcgatctgaccaaggacaagatggcgatgcagcggc tgcgggaagccgccgagaaggcaaagatcgagctgagttcgagtcagtcc acctcgatcaacctgccctacatcaccgtcgacgccgacaagaacccgtt gttcttagacgagcagctgacccgcgcggagttccaacggatcactcagg acctgctggaccgcactcgcaagccgttccagtcggtgatcgctgacacc ggcatttcggtgtcggagatcgatcacgttgtgctcgtgggtggttcgac ccggatgcccgcggtgaccgatctggtcaaggaactcaccggcggcaagg aacccaacaagggcgtcaaccccgatgaggttgtcgcggtgggagccgct ctgcaggccggcgtcctcaagggcgaggtgaaagacgttctgctgcttga tgttaccccgctgagcctgggtatcgagaccaagggcggggtgatgacca ggctcatcgagcgcaacaccacgatccccaccaagcggtcggagactttc accaccgccgacgacaaccaaccgtcggtgcagatccaggtctatcaggg ggagcgtgagatcgccgcgcacaacaagttgctcgggtccttcgagctga ccggcatcccgccggcgccgcggggggattccgcagatcgaggtcactttc gacatcgacgccaacggcattgtgcacgtcaccgccaaggacaagggcac cggcaaggagaacacgatccgaatccaggaaggctcgggcctgtccaagg aagacattgaccgcatgatcaaggacgccgaagcgcacgccgaggaggat cgcaagcgtcgcgaggaggccgatgttcgtaatcaagccgagacattggt ctaccagacggagaagttcgtcaaagaacagcgtgaggccgagggtggtt cgaaggtacctgaagacacgctgaacaaggttgatgccgcggtggcggaa gcgaaggcggcacttggcggatcggatatttcggccatcaagtcggcgat ggagaagctgggccaggagtcgcaggctctggggcaagcgatctacgaag cagctcaggctgcgtcacaggccactggcgctgcccaccccggcggcgag ccgggcggtgcccaccccggctcggctgatgacgttgtggacgcggaggt ggtcgacgacggccgggaggccaagtga 13. *M. tuberculosis* H37Rv|Rv0288|EsxH: 96 aa—LOW MOLECULAR WEIGHT PROTEIN ANTIGEN 7 ESXH (10 kDa ANTIGEN) (CFP-7) (PROTEIN TB10.4)

(SEQ ID NO: 16)

MSQIMYNYPAMLGHAGDMAGYAGTLQSLGAEIAVEQAALQSAWQGDTGIT

YQAWQAQWNQAMEDLVRAYHAMSSTHEANTMAMMARDTAEAAKWGG

*M. tuberculosis* H37Rv|Rv0288|esxH: 291 bp—LOW MOLECULAR WEIGHT PROTEIN ANTIGEN 7 ESXH (10 kDa ANTIGEN) (CFP-7) (PROTEIN TB10.4)

(SEQ ID NO: 35)

atgtcgcaaatcatgtacaactaccccgcgatgttgggtcacgccgggga tatggccggatatgccggcacgctgcagagcttgggtgccgagatcgccg tggagcaggccgcgttgcagagtgcgtggcagggcgataccgggatcacg tatcaggcgtggcaggcacagtggaaccaggccatggaagatttggtgcg ggcctatcatgcgatgtccagcacccatgaagccaacaccatggcgatga tggcccgcgacacggccgaagccgccaaatggggcggctag 14. *M. tuberculosis* H37Rv|Rv2031c|HspX: 144 aa—HEAT SHOCK PROTEIN HSPX (ALPHA-CRYSTALLIN HOMOLOG) (14 kDa ANTIGEN) (HSP16.3)

(SEQ ID NO: 17)

MATTLPVQRHPRSLFPEFSELFAAFPSFAGLRPTFDTRLMRLEDEMKEGR

YEVRAELPGVDPDKDVDIMVRDGQLTIKAERTEQKDFDGRSEFAYGSFVR

TVSLPVGADEDDIKATYDKGILTVSVAVSEGKPTEKHIQIRSTN

*M. tuberculosis* H37Rv|Rv2031c|hspX: 435 bp—HEAT SHOCK PROTEIN HSPX (ALPHA-CRYSTALLIN HOMOLOG) (14 kDa ANTIGEN) (HSP16.3)

(SEQ ID NO: 36)

atggccaccacccttcccgttcagcgccacccgcggtccctcttccccga gttttctgagctgttcgcggccttcccgtcattcgccggactccggccca ccttcgacacccggttgatgcggctggaagacgagatgaaagaggggcgc tacgaggtacgcgcggagcttcccggggtcgaccccgacaaggacgtcga cattatggtccgcgatggtcagctgaccatcaaggccgagcgcaccgagc agaaggacttcgacggtcgctcggaattcgcgtacggttccttcgttcgc acggtgtcgctgccggtaggtgctgacgaggacgacattaaggccaccta cgacaagggcattcttactgtgtcggtggcggtttcggaagggaagccaa ccgaaaagcacattcagatccggtccaccaactga 15. *M. tuberculosis* H37Rv|Rv0467|Icl: 428 aa—ISOCITRATE LYASE ICL (ISOCITRASE) (ISOCITRATASE)

(SEQ ID NO: 18)

MSVVGTPKSAEQIQQEWDTNPRWKDVTRTYSAEDVVALQGSVVEEHTLAR

RGAEVLWEQLHDLEWVNALGALTGNMAVQQVRAGLKAIYLSGWQVAGDAN

LSGHTYPDQSLYPANSVPQVVRRINNALQRADQIAKIEGDTSVENWLAPI

VADGEAGFGGALNVYELQKALIAAGVAGSHWEDQLASEKKCGHLGGKVLI

PTQQHIRTLTSARLAADVADVPTVVIARTDAEAATLITSDVDERDQPFIT

GERTREGFYRTKNGIEPCIARAKAYAPFADLIWMETGTPDLEAARQFSEA

VKAEYPDQMLAYNCSPSFNWKKHLDDATIAKFQKELAAMGFKFQFITLAG

FHALNYSMFDLAYGYAQNQMSAYVELQEREFAAEERGYTATKHQREVGAG

YFDRIATTVDPNSSTTALTGSTEEGQFH

*M. tuberculosis* H37Rv|Rv0467|icl: 1287 bp—ISOCITRATE LYASE ICL (ISOCITRASE) (ISOCITRATASE)

(SEQ ID NO: 37)

atgtctgtcgtcggcaccccgaagagcgcggagcagatccagcaggaatg ggacacgaacccgcgctggaaggacgtcacccgcacctactccgccgagg acgtcgtcgccctccagggcagcgtggtcgaggagcacacgctggcccgc cgcggtgcggaggtgctgtgggagcagctgcacgacctcgagtgggtcaa cgcgctgggcgcgctgaccggcaacatggccgtccagcaggtgcgcgccg gcctgaaggccatctacctgtcgggctggcaggtcgccggcgatgccaac ctgtccgggcacacctaccccgaccagagcctgtatcccgccaactcggt gccgcaggtggtccgccggatcaacaacgcactgcagcgcgccgaccaga tcgccaagatcgagggcgatacttcggtggagaactggctggcgccgatt gtcgccgacggcgaggccggctttggcggcgcgctcaacgtctacgagct gcagaaagccctgatcgccgcgggcgttgcgggttcgcactgggaggacc agttggcctctgagaagaagtgcggccacctgggcggcaaggtgttgatc ccgacccagcagcacatccgcactttgacgtctgctcggctcgcggccga tgtggctgatgttcccacggtggtgatcgcccgtaccgacgccgaggcgg ccacgctgatcacctccgacgtcgacgagcgcgaccagccgttcatcacc ggcgagcgcacccgggaaggcttctaccgcaccaagaacggcatcgagcc ttgcatcgctcgggcgaaggcctacgccccgttcgccgacttgatctgga tggagaccggtaccccggacctcgaggccgcccggcagttctccgaggcg gtcaaggcggagtacccggaccagatgctggcctacaactgctcgccatc gttcaactggaaaaagcacctcgacgacgccaccatcgccaagttccaga aggagctggcagccatgggcttcaagttccagttcatcacgctggccggc ttccatgcgctgaactactcgatgttcgatctggcctacggctacgccca gaaccagatgagcgcgtatgtcgaactgcaggaacgcgagttcgccgccg aagaacggggctacaccgcgaccaagcaccagcgcgaggtcggcgccggc tacttcgaccggattgccaccaccgtggacccgaattcgtcgaccaccgc gttgaccggttccaccgaagagggccagttccactag 16. *M. tuberculosis* H37Rv|Rv2660c|Rv2660c: 75 aa—HYPOTHETICAL PROTEIN (SEQ ID NO: 19)

VIAGVDQALAATGQASQRAAGASGGVTVGVGVGTEQRNLSVVAPSQFTFS

SRSPDFVDETAGQSWCAILGLNQFH

*M. tuberculosis* H37Rv|Rv2660c|Rv2660c: 228 bp—HYPOTHETICAL PROTEIN (SEQ ID NO: 38)

gtgatagcgggcgtcgaccaggcgcttgcagcaacaggccaggctagcca gcgggcggcaggcgcatctggtggggtcaccgtcggtgtcggcgtgggca cggaacagaggaacctttcggtggttgcaccgagtcagttcacatttagt tcacgcagcccagattttgtggatgaaaccgcaggtcaatcgtggtgcgc gatactgggattgaaccagtttcactag 17. *M. tuberculosis* H37Rv|Rv1837c|GlcB: 741 aa—PROBABLE MALATE SYNTHASE G GLCB (SEQ ID NO: 20)

MTDRVSVGNLRIARVLYDFVNNEALPGTDIDPDSFWAGVDKVVADLTPQN

QALLNARDELQAQIDKWHRRRVIEPIDMDAYRQFLTEIGYLLPEPDDFTI

TTSGVDAEITTTAGPQLVVPVLNARFALNAANARWGSLYDALYGTDVIPE

TDGAEKGPTYNKVRGDKVIAYARKFLDDSVPLSSGSFGDATGFTVQDGQL

VVALPDKSTGLANPGQFAGYTGAAESPTSVLLINHGLHIEILIDPESQVG

TTDRAGVKDVILESAITTIMDFEDSVAAVDAADKVLGYRNWLGLNKGDLA

AAVDKDGTAFLRVLNRDRNYTAPGGGQFTLPGRSLMFVRNVGHLMTNDAI

VDTDGSEVFEGIMDALFTGLIAIHGLKASDVNGPLINSRTGSIYIVKPKM

HGPAEVAFTCELFSRVEDVLGLPQNTMKIGIMDEERRTTVNLKACIKAAA

DRVVFINTGFLDRTGDEIHTSMEAGPMVRKGTMKSQPWILAYEDHNVDAG

LAAGFSGRAQVGKGMWTMTELMADMVETKIAQPRAGASTAWVPSPTAATL

HALHYHQVDVAAVQQGLAGKRRATIEQLLTIPLAKELAWAPDEIREEVDN

NCQSILGYVVRWVDQGVGCSKVPDIHDVALMEDRATLRISSQLLANWLRH

GVITSADVRASLERMAPLVDRQNAGDVAYRPMAPNFDDSIAFLAAQELIL

SGAQQPNGYTEPILHRRRREFKARAAEKPAPSDRAGDDAAR

*M. tuberculosis* H37Rv|Rv1837c|glcB: 2226 bp—PROBABLE MALATE SYNTHASE G GLCB (SEQ ID NO: 39)

atgacagatcgcgtgtcggtgggcaacttgcgcatcgctcgggtgctcta cgacttcgtgaacaatgaagccctgcctggcaccgatatcgacccggaca gcttctgggcgggcgtcgacaaggtcgtcgccgacctgaccccgcagaac caagctctgttgaacgcccgcgacgagctgcaggcgcagatcgacaagtg gcaccggcgtcgggtgatcgagcccatcgacatggatgcctaccgccagt tcctcaccgagatcggctacctgcttcccgaacctgatgacttcaccatc accacgtccggtgtcgacgctgagatcaccacgaccgccggcccccagct ggtggtgccggtgctcaacgcgcggtttgctctgaacgcggccaacgctc gctggggctccctctacgacgccttgtatggcaccgatgtcatccccgag accgacggcgccgaaaaaggccccacgtacaacaaggttcgtggcgacaa ggtgatcgcgtatgcccgcaagttcctcgacgacagtgttccgctgtcgt cgggttcctttggcgacgccaccggtttcacagtgcaggatggccagctc gtggttgccttgccggataagtccaccggcctggccaaccccggccagtt cgccggctacaccggcgcagccgagtcgccgacatcggtgctgctaatca atcacggtttgcacatcgagatcctgatcgatccggagtcgcaggtcggc accaccgaccgggccggcgtcaaggacgtgatcctggaatccgcgatcac cacgatcatggacttcgaggactcggtggccgccgtggacgccgccgaca aggtgctgggttatcggaactggctcggcctgaacaagggcgacctggca gcagcggtagacaaggacggcaccgctttcctgcgggtgctcaataggga -continued

```
ccggaactacaccgcacccggcggtggccagttcacgctgcctggacgca gcctcatgttcgtccgcaacgtcggtcaccttgagacgaatgacgccatc gtcgacactgacggcagcgaggtgttcgaaggcatcatggatgccctatt caccggcctgatcgccatccacgggctaaaggccagcgacgtcaacgggc cgctgatcaacagccgcaccggctccatctacatcgtcaagccgaagatg cacggtccggccgaggtggcgtttacctgcgaactgttcagccgggttga agatgtgctggggttgccgcaaaacaccatgaagatcggcatcatggacg aggaacgccggaccacggtcaacctcaaggcgtgcatcaaagctgccgcg gaccgcgtggtgttcatcaacaccgggttcctggaccgcaccggcgatga aatccacacctcgatggaggccggcccgatggtgcgcaagggcaccatga agagccagccgtggatcttggcctacgaggaccacaacgtcgatgccggc ctggccgccgggttcagcggccgagcccaggtcggcaagggcatgtggac aatgaccgagctgatggccgacatggtcgagacaaaaatcgcccagccgc gcgccggggccagcaccgcctgggttccctctcccactgcggccaccctg catgcgctgcactaccaccaggtcgacgtcgccgcggtgcaacaaggact ggcggggaagctcgcgccaccatcgacaattgctgaccattccgctgg ccaaggaattggcctgggctcccgacgagatccgcgaagaggtcgacaac aactgtcaatccatcctcggctacgtggttcgctgggttgatcaaggtgt cggctgctcgaaggtgcccgacatccacgacgtcgcgctcatggaggacc gggccacgctgcgaatctccagccaattgttggccaactggctgcgccac ggtgtgatcaccagcgcggatgtgcgggccagcttggagcggatggcgcc gttggtcgatcgacaaaacgcgggcgacgtggcataccgaccgatggcac ccaacttcgacgacagtatcgccttcctggccgcgcaggagctgatcttg tccggggcccagcagcccaacggctacaccgagccgatcctgcaccgacg
``` tcgtcgggagtttaaggcccgggccgctgagaagccggccccatcggaca gggccggtgacgatgcggcccgctag

18. *M. tuberculosis* H37Rv|Rv1475c|Acn: 943 aa—PROBABLE IRON-REGULATED ACONITATE HYDRATASE ACN (Citrate hydro-lyase) (Aconitase)

(SEQ ID NO: 21)

VTSKSVNSFGAHDTLKVGEKSYQIYRLDAVPNTAKLPYSLKVLAENLLRN

EDGSNITKDHIEAIANWDPKAEPSIEIQYTPARVVMQDFTGVPCIVDLAT

MREAIADLGGNPDKVNPLAPADLVIDHSVIADLFGRADAFERNVEIEYQR

NGERYQFLRWGQGAFDDFKVVPPGTGIVHQVNIEYLASVVMTRDGVAYPD

TCVGTDSHTTMVNGLGVLGWGVGGIEAEAAMLGQPVSMLIPRVVGFRLTG

EIQPGVTATDVVLTVTEMLRQHGVVGKFVEFYGEGVAEVPLANRATLGNM

SPEFGSTAAIFPIDEETIKYLRFTGRTPEQVALVEAYAKAQGMWHDPKHE

PEFSEYLELNLSDVVPSIAGPKRPQDRIALAQAKSTFREQIYHYVGNGSP

DSPHDPHSKLDEVVEETFPASDPGQLTFANDDVATDETVHSAAAHADGRV

SNPVRVKSDELGEFVLDHGAVVIAAITSCTNTSNPEVMLGAALLARNAVE

KGLTSKPWVKTTIAPGSQVVNDYYDRSGLWPYLEKLGFYLVGYGCTTCIG

NSGPLPEEISKAVNDNDLSVTAVLSGNRNFEGRINPDVKHNYLASPPLVI

AYALAGTMDFDFQTQPLGQDKDGKNVFLRDIWPSQQDVSDTIAAAINQEM

FTRNYADVFKGDDRWRNLPTPSGNTFEWDPNSTYVRKPPYFEGMTAKPEP

VGNISGARVLALLGDSVTTDHISPAGAIKPGTPAARYLDEHGVDRKDYNS

FGSRRGNHEVMIRGTFANIRLRNQLLDDVSGGYTRDFTQPGGPQAFIYDA

AQNYAAQHIPLVVFGGKEYGSGSSRDWAAKGTLLLGVRAVIAESFERIHR

SNLIGMGVIPLQFPEGKSASSLGLDGTEVFDITGIDVLNDGKTPKTVCVQ

ATKGDGATIEFDAVVRIDTPGEADYYRNGGILQYVLRNILKSG

*M. tuberculosis* H37Rv|Rv1475c|acn: 2832 bp—PROBABLE IRON-REGULATED ACONITATE HYDRATASE ACN (Citrate hydro-lyase) (Aconitase)

(SEQ ID NO: 40)

```
gtgactagcaaatctgtgaactcattcggagcccacgacaccctgaaggtcggcgaaaag agttaccagatctatcgtctcgacgccgtccccaataccgcgaaactcccctacagcctc aaagtgctcgccgagaacctgttgcgcaacgaggacggcagcaacatcaccaaggaccac atcgaggccatcgccaactgggaccctaaggccgagcccagcatcgagatccagtacacg cccgcccggtggtgatgcaggacttcaccggcgtaccgtgcatcgtcgacttggccacc atgcgcgaggcgatcgcgatctgggcggcaacccggacaaggtcaaccgctggcgccc gcagacttggtgatcgaccactcggtgatcgccgatttgttcggccgcgccgacgcattc gagcgcaacgtcgaaatcgaataccagcgcaacggtgagcgttaccaattcctgcgctgg ggccaaggcgctttcgacgacttcaaagtggtgccgccgggcaccggcatcgtgcaccag gtcaatatcgagtacctggccagcgtggtgatgactcgcgacggagtggcctaccccgac acctgcgtgggcaccgactcacacaccaccatggtcaacggcctgggtgtgctcgggtgg ggtgtcggcggcatcgaggcggaggccgcgatgctgggtcagccggtatcgatgctgatc
```

-continued

```
ccgcgggtcgtgggtttcaggttgaccggcgagatccagccgggagtcaccgccaccgac
gtggtgttgaccgtcaccgagatgctgcgccagcacggcgtcgtcggcaaattcgtcgag
ttctacggcgagggcgtggccgaggtgccgctggccaaccgcgccaccctgggcaacatg
agtcccgaattcggttccaccgcagcgattttcccgatcgacgaagaaaccatcaagtat
ctgcggtttaccggtcgcacgccggagcaggtcgcactggtcgaggcctacgccaaggcg
cagggcatgtggcacgatcccaagcacgagccggagttctcggaatacctcgaactcaac
ctatccgacgtggtgccgtcagtcgccggaccaaagcgtccacaggaccgaatcgcgttg
gcgcaagccaaatcaacattccgcgagcagatttaccactatgtcggcaatggttcccg
gattcccccacgaccgcactcgaagctggacgaggtagtcgaggagacattcccggcc
agcgaccggggcagctgacgttcgccaacgacgacgtcgccactgacgaaaccgtgcac
tcggctgccgcgcatgccgatggccgggtgagcaacccagtgcgggtgaagtcggacgga
ctcggcgaattcgtgctcgaccacggcgcggtggtgattgccgcgatcacgtcctgcacc
aacacctccaaccccgaagtaatgctgggcgcggcgctgctggcccgcaacgccgtcgaa
aagggactgacctcgaagccgtgggtgaagaccacgattgccccgggctcgcaagtggtc
aacgactactacgacagatccggcctgtggccgtatctggagaagctcggcttctatctg
gtcggctacggctgcaccacctgcatcggcaactccgggccgctgcccgaggaaatctca
aaagcggttaacgacaacgacctttcggtgaccgcggtactgtccggcaaccggaacttc
gagggccgtatcaacccagacgtgaagatgaactacctggcatcgccgccgctggtcatc
gcctacgcgctggccgggaccatggacttcgacttccaaacccagccgctcggtcaagac
aaagacggtaagaacgttttctccgcgatatctggccatcgcagcaggatgtctccgac
accatcgccgcggcgatcaaccaggagatgttcacccgcaactacgccgacgtgttcaag
ggcgacgaccgctggcgcaacctgccaaccccgagcggcaacacctttgagtgggacccg
aattcgacctacgtgcgcaagccgccgtatttcgaggggatgacagccaaacccgaaccg
gtcggcaacatcagcggtgcccgggtgctggcgctgctcggtgattcggtgaccaccgac
cacatctccccgccggcgccatcaagcccggaactcccgcggcgcgctacctcgacgaa
cacggtgtcgaccgcaaggactacaactccttcggttctcgccgcggcaaccacgaggtg
atgattcgtggcaccttcgccaacatccggctgcgtaaccaactgctagacgacgtgtcc
ggcggttatacccgcgacttcacccagccgggcggtccgcaggcgttcatctacgacgcc
gcgcagaactatgcggcgcaacacattccgctggttgtgttcggcggcaaagagtacggg
tcgggttcgtcacgggactgggcggccaaaggcacattgctactgggcgtgcgggcggtg
atcgccgagtcattcgagcggatccaccggtccaacctgatcggcatgggcgtgatcccg
ctgcagttccccgaaggaaagtcagcgtcgtcgttgggactcgacggtaccgaggtcttc
gacatcaccggtatcgacgtgcttaacgacggcaagacacccaagacggtgtgcgtccag
gccaccaagggcgacggcgccacgatcgagttcgacgccgtggtgcgcatcgacaccccc
ggtgaggcggactactaccgcaacggcggcatcctgcagtacgtgctgcgcaacatactg
aagtcaggctga
```

19. *M. tuberculosis* H37Rv|Rv3875|EsxA: 95 aa—6 KDA EARLY SECRETORY ANTIGENIC TARGET ESXA (ESAT-6)

(SEQ ID NO: 22)
MTEQQWNFAGIEAAASAIQGNVTSIHSLLDEGKQSLTKLAAAWGGSGSEA

YQGVQQKWDATATELNNALQNLARTISEAGQAMASTEGNVTGMFA

*M. tuberculosis* H37Rv|Rv3875|esxA: 288 bp—6 KDA EARLY SECRETORY ANTIGENIC TARGET ESXA (ESAT-6)

(SEQ ID NO: 41)
atgacagagcagcagtggaatttcgcgggtatcgaggccgcggcaagcgc aatccagggaaatgtcacgtccattcattccctccttgacgaggggaagc agtccctgaccaagctcgcagcggcctgggcggtagcggttcggaggcg taccagggtgtccagcaaaaatgggacgccacggctaccgagctgaacaa cgcgctgcagaacctggcgcggacgatcagcgaagccggtcaggcaatgg cttcgaccgaaggcaacgtcactgggatgttcgcatag

Polynucleotide and Polypeptide Sequences from: *Listeria monocytogenes* (EGD Strain)

ActA actin-assembly inducing protein precursor
(Listeria monocytogenes EGD-e)
(SEQ ID NO: 1)
MGLNRFMRAMMVVFITANCITINPDIIFAATDSEDSSLNTDEWEEEKTEE

QPSEVNTGPRYETAREVSSRDIKELEKSNKVRNTNKADLIAMLKEKAEKG

PNINNNNSEQTENAAINEEASGADRPAIQVERRHPGLPSDSAAEIKKRRK

AIASSDSELESLTYPDKPTKVNKKKVAKESVADASESDLDSSMQSADESS

PQPLKANQQPFFPKVFKKIKDAGKWVRDKIDENPEVKKAIVDKSAGLIDQ

LLTKKKSEEVNASDFPPPPTDEELRLALPETPMLLGFNAPATSEPSSFEF

PPPPTDEELRLALPETPMLLGFNAPATSEPSSFEFPPPPTEDELEIIRET

ASSLDSSFTRGDLASLRNAINRHSQNFSDFPPIPTEEELNGRGGRPTSEE

FSSLNSGDFTDDENSETTEEEIDRLADLRDRGTGKHSRNAGFLPLNPFAS

SPVPSLSPKVSKISAPALISDITKKTPFKNPSQPLNVFNKKTTTKTVTKK

PTPVKTAPKLAELPATKKPQETVLRENKTPFIEKQAETNKQSINMPSLPVI

QKEATESDKEEMKPQTEEKMVEESESANNANGKNRSAGIEEGKLIAKSAE

DEKAKEEPGNHTTLILAMLAIGVFSLGAFIKIIQLRKNN gene = "actA" (Listeria monocytogenes EGD-e)
(SEQ ID NO: 42)
GTGGGATTAAACAGATTTATGCGTGCGATGATGGTGGTTTTCATTACTGC

CAATTGCATTACGATTAACCCCGACATAATATTTGCAGCGACAGATAGCG

AAGATTCTAGTCTAAACACAGATGAATGGGAAGAAGAAAAAACAGAAGAG

CAACCAAGCGAGGTAAATACGGGACCAAGATACGAAACTGCACGTGAAGT

AAGTTCACGTGATATTAAAGAACTAGAAAAATCGAATAAAGTGAGAAATA

CGAACAAAGCAGACCTAATAGCAATGTTGAAAGAAAAAGCAGAAAAAGGT

CCAAATATCAATAATAACAACAGTGAACAAACTGAGAATGCGGCTATAAA

TGAAGAGGCTTCAGGAGCCGACCGACCAGCTATACAAGTGGAGCGTCGTC

ATCCAGGATTGCCATCGGATAGCGCAGCGGAAATTAAAAAAAGAAGGAAA

GCCATAGCATCATCGGATAGTGAGCTTGAAAGCCTTACTTATCCGGATAA

ACCAACAAAAGTAAATAAGAAAAAAGTGGCGAAAGAGTCAGTTGCGGATG

CTTCTGAAAGTGACTTAGATTCTAGCATGCAGTCAGCAGATGAGTCTTCA

CCACAACCTTTAAAAGCAAACCAACAACCATTTTTCCCTAAAGTATTTAA

AAAAATAAAAGATGCGGGGAAATGGGTACGTGATAAAATCGACGAAAATC

CTGAAGTAAAGAAAGCGATTGTTGATAAAAGTGCAGGGTTAATTGACCAA

TTATTAACCAAAAAGAAAAGTGAAGAGGTAAATGCTTCGGACTTCCCGCC

ACCACCTACGGATGAAGAGTTAAGACTTGCTTTGCCAGAGACACCAATGC

TTCTTGGTTTTAATGCTCCTGCTACATCAGAACCGAGCTCATTCGAATTT

CCACCACCACCTACGGATGAAGAGTTAAGACTTGCTTTGCCAGAGACGCC

AATGCTTCTTGGTTTTAATGCTCCTGCTACATCGGAACCGAGCTCGTTCG

AATTTCCACCGCCTCCAACAGAAGATGAACTAGAAATCATCCGGGAAACA

GCATCCTCGCTAGATTCTAGTTTTACAAGAGGGGATTTAGCTAGTTTGAG

AAATGCTATTAATCGCCATAGTCAAAATTTCTCTGATTTCCCACCAATCC

CAACAGAAGAAGAGTTGAACGGGAGAGGCGGTAGACCAACATCTGAAGAA

TTTAGTTCGCTGAATAGTGGTGATTTTACAGATGACGAAAACAGCGAGAC

AACAGAAGAAGAAATTGATCGCCTAGCTGATTTAAGAGATAGAGGAACAG

GAAAACACTCAAGAAATGCGGGTTTTTTACCATTAAATCCGTTTGCTAGC

AGCCCGGTTCCTTCGTTAAGTCCAAAGGTATCGAAAATAAGCGCACCGGC

TCTGATAAGTGACATAACTAAAAAAACGCCATTTAAGAATCCATCACAGC

CATTAAATGTGTTTAATAAAAAAACTACAACGAAAACAGTGACTAAAAAA

CCAACCCCTGTAAAGACCGCACCAAAGCTAGCAGAACTTCCTGCCACAAA

ACCACAAGAAACCGTACTTAGGGAAAATAAAACACCCTTTATAGAAAAAC

AAGCAGAAACAAACAAGCAGTCAATTAATATGCCGAGCCTACCAGTAATC

CAAAAAGAAGCTACAGAGAGCGATAAAGAGGAAATGAAACCACAAACCGA

GGAAAAAATGGTAGAGGAAAGCGAATCAGCTAATAACGCAAACGGAAAAA

ATCGTTCTGCTGGCATTGAAGAAGGAAAACTAATTGCTAAAAGTGCAGAA

GACGAAAAAGCGAAGGAAGAACCAGGGAACCATACGACGTTAATTCTTGC

AATGTTAGCTATTGGCGTGTTCTCTTTAGGGGCGTTTATCAAAATTATTC

AATTAAGAAAAAATAATTAA

LLO listeriolysin O precursor (Listeria monocytogenes EGD-e)
(SEQ ID NO: 43)
MKKIMLVFITLILVSLPIAQQTEAKDASAFNKENSISSMAPPASPPASPK

TPIEKKHADEIDKYIQGLDYNKNNVLVYHGDAVTNVPPRKGYKDGNEYIV

VEKKKKSINQNNADIQVVNAISSLTYPGALVKANSELVENQPDVLPVKRD

SLTLSIDLPGMTNQDNKIVVKNATKSNVNNAVNTLVERWNEKYAQAYPNV

SAKIDYDDEMAYSESQLIAKFGTAFKAVNNSLNVNFGAISEGKMQEEVIS

-continued

FKQIYYNVNVNEPTRPSRFFGKAVTKEQLQALGVNAENPPAYISSVAYGR

QVYLKLSTNSHSTKVKAAFDAAVSGKSVSGDVELTNIIKNSSFKAVIYGG

SAKDEVQIIDGNLGDLRDILKKGATFNRETPGVPIAYTTNFLKDNELAVI

KNNSEYIETTSKAYTDGKINIDHSGGYVAQFNISWDEVNYDPEGNEIVQH

KNWSENNKSKLAHFTSSIYLPGNARNINVYAKECTGLAWEWWRTVIDDRN

LPLVKNRNISIWGTTLYPKYSNKVDNPIE gene = "hly" (Listeria monocytogenes EGD-e)
(SEQ ID NO: 44)
ATGAAAAAAATAATGCTAGTTTTTATTACACTTATATTAGTTAGTCTACC

AATTGCGCAACAAACTGAAGCAAAGGATGCATCTGCATTCAATAAAGAAA

ATTCAATTTCATCCATGGCACCACCAGCATCTTCCGCCTGCAAGTCCTAAG

ACGCCAATCGAAAGAAACACGCGGATGAAATCGATAAGTATATACAAGG

ATTGGATTACAATAAAAACAATGTATTAGTATACCACGGAGATGCAGTGA

CAAATGTGCCGCCAAGAAAAGGTTACAAAGATGGAAATGAATATATTGTT

GTGGAGAAAAGAAGAAATCCATCAATCAAAATAATGCAGACATTCAAGT

TGTGAATGCAATTTCGAGCCTAACCTATCCAGGTGCTCTCGTAAAAGCGA

ATTCGGAATTAGTAGAAAATCAACCAGATGTTCTCCCTGTAAAACGTGAT

TCATTAACACTCAGCATTGATTTGCCAGGTATGACTAATCAAGACAATAA

AATCGTTGTAAAAAATGCCACTAAATCAAACGTTAACAACGCAGTAAATA

CATTAGTGGAAAGATGGAATGAAAAATATGCTCAAGCTTATCCAAATGTA

AGTGCAAAAATTGATTATGATGACGAAATGGCTTACAGTGAATCACAATT

AATTGCGAAATTTGGTACAGCATTTAAAGCTGTAAATAATAGCTTGAATG

TAAACTTCGGCGCAATCAGTGAAGGGAAATGCAAGAAGAAGTCATTAGT

TTTAAACAAATTTACTATAACGTGAATGTTAATGAACCTACAAGACCTTC

CAGATTTTTCGGCAAAGCTGTTACTAAAGAGCAGTTGCAAGCGCTTGGAG

TGAATGCAGAAAATCCTCCTGCATATATCTCAAGTGTGGCGTATGGCCGT

CAAGTTTATTTGAAATTATCAACTAATTCCCATAGTACTAAAGTAAAAGC

TGCTTTTGATGCTGCCGTAAGCGGAAAATCTGTCTCAGGTGATGTAGAAC

TAACAAATATCATCAAAAATTCTTCCTTCAAAGCCGTAATTTACGGAGGT

TCCGCAAAAGATGAAGTTCAAATCATCGACGGCAACCTCGGAGACTTACG

CGATATTTTGAAAAAGGCGCTACTTTTAATCGAGAAACACCAGGAGTTC

CCATTGCTTATACAACAAACTTCCTAAAAGACAATGAATTAGCTGTTATT

AAAAACAACTCAGAATATATTGAAACAACTTCAAAAGCTTATACAGATGG

AAAAATTAACATCGATCACTCTGGAGGATACGTTGCTCAATTCAACATTT

CTTGGGATGAAGTAAATTATGATCCTGAAGGTAACGAAATTGTTCAACAT

AAAAACTGGAGCGAAAACAATAAAAGCAAGCTAGCTCATTTCACATCGTC

CATCTATTTGCCAGGTAACGCGAGAAATATTAATGTTTACGCTAAAGAAT

GCACTGGTTTAGCTTGGGAATGGTGGAGAACGGTAATTGATGACCGGAAC

TTACCACTTGTGAAAAATAGAAATATCTCCATCTGGGGCACCACGCTTTA

TCCGAAATATAGTAATAAAGTAGATAATCCAATCGAATAA

Internalin B internalin B (Listeria monocytogenes EGD-e)
(SEQ ID NO: 2)
MKEKHNPRRKYCLISGLAIIFSLWIIIGNGAKVQAETITVPTPIKQIFSD

DAFAETIKDNLKKKSVTDAVTQNELNSIDQIIANNSDIKSVQGIQYLPNV

TKLFLNGNKLTDIKPLANLKNLGWLFLDENKVKDLSSLKDLKKLKSLSLE

HNGISDINGLVHLPQLESLYLGNNKITDITVLSRLTKLDTLSLEDNQISD

IVPLAGLTKLQNLYLSKNHISDLRALAGLKNLDVLELFSQECLNKPINHQ

SNLVVPNTVKNTDGSLVTPEIISDDGDYEKPNVKWHLPEFTNEVSFIFYQ

PVTIGKAKARFHGRVTQPLKEVYTVSYDVDGTVIKTKVEAGTRITAPKPP

TKQGYVFKGWYTEKNGGHEWNFNTDYMSGNDFTLYAVFKAETTEKAVNLT

RYVKYIRGNAGIYKLPREDNSLKQGTLASHRCKALTVDREARNGGKLWYR

LKNIGWTKAENLSLDRYDKMEYDKGVTAYARVRNASGNSVWTKPYNTAGA

KHVNKLSVYQGKNMRILREAKTPITTWYQFSIGGKVIGWVDTRALNTFYK

QSMEKPTRLTRYVSANKAGESYYKVPVADNPVKRGTLAKYKNQKLIVDCQ

ATIEGQLWYRIRTSSTFIGWTKAANLRAQK gene = "inlB" (Listeria monocytogenes EGD-e)
(SEQ ID NO: 45)
GTGAAAGAAAAGCACAACCCAAGAAGGAAGTATTGTTTAATCTCAGGTTT

AGCTATTATTTTTAGTTTATGGATAATTATTGGAAACGGGGCGAAAGTAC

AAGCGGAGACTATCACCGTGCCAACGCCAATCAAGCAAATTTTTTCAGAT

GATGCTTTTGCAGAAACAATCAAAGACAATTTAAAGAAAAAAGTGTGAC

AGATGCAGTGACACAAAATGAATTAAATAGTATAGATCAAATCATTGCGA

ATAATAGTGATATTAAATCCGTTCAAGGAATTCAGTATTTACCCAATGTG

ACAAAGTTATTTTTAAACGGGAATAAACTAACAGATATAAAGCCCTTAGC

AAACTTGAAAAATTTAGGATGGCTTTTTTTAGACGAAAATAAAGTTAAGG

ACCTAAGTTCGCTCAAGGATTAAAAAAATTAAAATCACTTTCTTTGGAG

CATAATGGTATAAGTGATATAAACGGACTTGTTCATTTACCACAGCTGGA

AAGTTTGTATTTGGGAAATAATAAAATAACGGATATAACGGTTCTTTCAC

GTTTAACTAAACTGGATACTTGTCTCTCGAAGATAACCAAATTAGTGAT

ATTGTGCCACTTGCAGGTTTAACTAAATTGCAGAACCTATATTTAAGTAA

AAATCACATAAGCGATTTAAGAGCATTAGCAGGACTTAAAAATCTAGATG

TTTTAGAATTATTTAGCCAAGAATGTCTTAATAAGCCTATTAATCATCAA

TCTAATTTGGTTGTTCCGAATACAGTGAAAAACACTGATGGGTCGTTAGT

GACTCCAGAAATAATAAGTGATGATGGCGATTATGAAAAACCTAATGTTA

AATGGCATTTACCAGAATTTACAAATGAAGTGAGTTTTATTTTCTATCAG

CCAGTCACTATTGGAAAAGCAAAAGCAAGATTTCATGGGAGAGTAACCCA

ACCACTGAAAGAGGTTTACACAGTAAGTTATGATGTTGATGGAACGGTAA

TAAAAACAAAAGTAGAAGCAGGGACGCGGATAACTGCACCTAAACCTCCG

ACTAAACAAGGCTATGTTTTTAAAGGATGGTATACTGAAAAAAATGGTGG

GCATGAGTGGAATTTTAATACGGATTATATGTCCGGAAATGATTTTACTT

TGTACGCAGTATTTAAAGCGGAAACGACCGAAAAAGCAGTCAACTTAACC

```
CGCTATGTCAAATATATTCGCGGGAATGCAGGCATCTACAAACTTCCACG

AGAAGATAACTCGCTTAAACAAGGAACTCTAGCCTCGCACCGCTGTAAAG

CTCTAACTGTTGATAGAGAAGCCCGAAATGGCGGAAAATTATGGTACAGG

TTAAAAAATATTGGCTGGACTAAAGCGGAAAACCTTTCCTTAGACCGATA

CGATAAAATGGAATATGACAAAGGGGTTACCGCTTATGCAAGAGTGAGAA

ATGCGTCTGGAAATTCGGTTTGGACAAAACCCTACAACACAGCCGGCGCT

AAACACGTGAATAAGCTATCGGTCTACCAAGGTAAAAATATGCGTATCTT

GCGCGAAGCCAAAACACCAATTACTACATGGTATCAATTTAGCATTGGTG

GTAAAGTAATTGGTTGGGTCGATACCCGAGCACTTAACACATTCTACAAA

CAAAGCATGGAAAAGCCAACCCGTTTAACTCGTTATGTCAGCGCCAATAA

AGCTGGCGAATCGTACTATAAAGTCCCGGTAGCAGATAATCCAGTCAAAA

GGGGTACTTTAGCCAAGTATAAAAATCAAAAGTTAATTGTTGATTGTCAA

GCAACCATCGAAGGTCAACTTTGGTACCGAATAAGGACTAGTTCCACTTT

CATTGGTTGGACGAAAGCAGCTAATTTAAGGGCACAGAAATAA
```

PrfA listeriolysin positive regulatory protein
(Listeria monocytogenes EGD-e)
(SEQ ID NO: 3)

MNAQAEEFKKYLETNGIKPKQFHKKELIFNQWDPQEYCIFLYDGITKLTS

ISENGTIMNLQYYKGAFVIMSGFIDTETSVGYYNLEVISEQATAYVIKIN

ELKELLSKNLTHFFYVFQTLQKQVSYSLAKFNDFSINGKLGSICGQLLIL

TYVYGKETPDGIKITLDNLTMQELGYSSGIAHSSAVSRIISKLKQEKVIV

YKNSCFYVQNLDYLKRYAPKLDEWFYLACPATWGKLN gene = "prfA" complement(1 . . . 714)prfA
(Listeria monocytogenes EGD-e)
(SEQ ID NO: 46)

```
TTAATTTAATTTTCCCCAAGTAGCAGGACATGCTAAATAAAACCATTCAT

CTAATTTAGGGGCATATCTTTTGAGATAATCAAGATTTTGTACATAAAAG

CATGAATTTTTATACACGATAACTTTCTCTTGCTTTAATTTGGAAATAAT

TCTGCTAACAGCTGAGCTATGTGCGATGCCACTTGAATATCCTAACTCCT

GCATTGTTAAATTATCCAGTGTAATCTTGATGCCATCAGGAGTTTCTTTA

CCATACACATAGGTCAGGATTAAAAGTTGACCGCAAATAGAGCCAAGCTT

CCCGTTAATCGAAAAATCATTAAATTTAGCTAGACTGTATGAAACTTGTT

TTTGTAGGGTTTGGAAAACATAGAAAAAGTGCGTAAGATTTTTGCTCAGT

AGTTCTTTTAGTTCGTTTATTTTGATAACGTATGCGGTAGCCTGCTCGCT

AATGACTTCTAAATTATAATAGCCAACCGATGTTTCTGTATCAATAAAGC

CAGACATTATAACGAAAGCCCCTTTGTAGTATTGTAAATTCATGATGGTC

CCGTTCTCGCTAATACTCGTGAGCTTTGTGATACCATCATATAGAAAAAT

ACAATATTCTTGTGGATCCCATTGGTTAAAAATAAGTTCTTTTTTATGAA

ATTGTTTTGGTTTTATCCCGTTAGTTTCTAAATATTTTTTGAATTCTTCT

GCTTGAGCGTTCAT
```

---

The invention claimed is:

1. A method of generating an antibody to a *Mycobacterium tuberculosis* 30 kDa antigen 85B protein (SEQ ID NO: 4) comprising the steps of:
   immunizing a mammal with a composition consisting essentially of *Mycobacterium bovis* strain Bacille Calmette-Guérin (BCG) in a primary immunization, wherein said *Mycobacterium bovis* strain BCG is not a recombinant strain BCG;
   immunizing a mammal with a composition of matter comprising attenuated *Listeria monocytogenes* in a booster immunization, wherein the *Listeria monocytogenes:*
   does not express a functional ActA protein (SEQ ID NO: 1);
   expresses prfA protein having a G155S substitution mutation (SEQ ID NO: 3); and
   expresses *Mycobacterium tuberculosis* 30 kDa antigen 85B protein (SEQ ID NO: 4);
   such that an antibody to a *Mycobacterium tuberculosis* 30 kDa antigen 85B protein is generated.

2. The method of claim 1, wherein the *Listeria monocytogenes* expresses *Mycobacterium tuberculosis* 32 kDa 85A protein (SEQ ID NO: 11).

3. The method of claim 1, wherein the *Listeria monocytogenes:* does not express a functional InlB protein (SEQ ID NO: 2).

4. The method of claim 1, wherein the mammal is immunized intranasally, subcutaneously, intradermally, intramuscularly or orally.

5. The method of claim 1, wherein the mammal is a guinea pig or a mouse.

6. The method of claim 1, wherein the mammal is a human.

7. The method of claim 1, wherein the *Listeria monocytogenes* further expresses at least one protein from the following group:
*Mycobacterium tuberculosis* 12 kDa fragment of 16 kDa membrane protein (SEQ ID NO:5);
*Mycobacterium tuberculosis* 14 kDa MPT53 protein (SEQ ID NO: 6);
*Mycobacterium tuberculosis* 16 kDa MPT63 protein (SEQ ID NO: 7);
*Mycobacterium tuberculosis* 23 kDa SOD protein (SEQ ID NO: 8);
*Mycobacterium tuberculosis* 23.5 kDa MPT64 protein (SEQ ID NO: 9);
*Mycobacterium tuberculosis* 24 kDa MPT51 protein (SEQ ID NO: 10);
*Mycobacterium tuberculosis* 32 kDa antigen 85A protein (SEQ ID NO: 11);
*Mycobacterium tuberculosis* 32 kDa antigen 85C protein (SEQ ID NO: 12);
*Mycobacterium tuberculosis* 45 kDa MPT32 protein (SEQ ID NO: 13);
*Mycobacterium tuberculosis* 58 kDa glutamine synthetase protein (SEQ ID NO: 14);
*Mycobacterium tuberculosis* 71 kDa HSP 70 protein (SEQ ID NO: 15);
*Mycobacterium tuberculosis* 10.4 kDa EsxH protein (SEQ ID NO: 16);
*Mycobacterium tuberculosis* 14 kDa alpha crystalline homolog protein (SEQ ID NO: 17);
*Mycobacterium tuberculosis* 47 kDa isocytrate lysate protein (SEQ ID NO: 18);
*Mycobacterium tuberculosis* 7.6 kDa hypothetical protein (SEQ ID NO: 19);
*Mycobacterium tuberculosis* 80 kDa glcB protein (SEQ ID NO: 20);
*Mycobacterium tuberculosis* 110 kDa can protein (SEQ ID NO: 21); or
*Mycobacterium tuberculosis* 9.9 kDa ESAT-6 protein (SEQ ID NO: 22).

8. The method of claim 1, wherein the *Listeria monocytogenes* further expresses at least one protein from group A:
*Mycobacterium tuberculosis* 12 kDa fragment of 16 kDa membrane protein (SEQ ID NO:5);
*Mycobacterium tuberculosis* 14 kDa MPT53 protein (SEQ ID NO: 6);
*Mycobacterium tuberculosis* 16 kDa MPT63 protein (SEQ ID NO: 7);
*Mycobacterium tuberculosis* 23 kDa SOD protein (SEQ ID NO: 8);
*Mycobacterium tuberculosis* 23.5 kDa MPT64 protein (SEQ ID NO: 9);
*Mycobacterium tuberculosis* 24 kDa MPT51 protein (SEQ ID NO: 10);
*Mycobacterium tuberculosis* 32 kDa antigen 85A protein (SEQ ID NO: 11);
*Mycobacterium tuberculosis* 32 kDa antigen 85C protein (SEQ ID NO: 12);
*Mycobacterium tuberculosis* 45 kDa MPT32 protein (SEQ ID NO: 13);
*Mycobacterium tuberculosis* 58 kDa glutamine synthetase protein (SEQ ID NO: 14);
*Mycobacterium tuberculosis* 71 kDa HSP 70 protein (SEQ ID NO: 15);
*Mycobacterium tuberculosis* 10.4 kDa EsxH protein (SEQ ID NO: 16);
*Mycobacterium tuberculosis* 80 kDa glcB protein (SEQ ID NO: 20);
*Mycobacterium tuberculosis* 110 kDa can protein (SEQ ID NO: 21); or
*Mycobacterium tuberculosis* 9.9 kDa ESAT-6 protein (SEQ ID NO: 22);
at least one protein from group B:
*Mycobacterium tuberculosis* 14 kDa alpha crystalline homolog protein (SEQ ID NO: 17);
*Mycobacterium tuberculosis* 47 kDa isocytrate lysate protein (SEQ ID NO: 18); or
*Mycobacterium tuberculosis* 7.6 kDa hypothetical protein (SEQ ID NO: 19).

9. The method of claim 1, wherein the *Mycobacterium tuberculosis* 30 kDa antigen 85B protein is coupled to a heterologous protein sequence comprising the N-terminal 100 amino acids of the ActA protein.

10. The method of claim 9, wherein the expression of the *Mycobacterium tuberculosis* 30 kDa antigen 85B protein is controlled by an ActA promoter.

11. A method of generating an immune response to a *Mycobacterium tuberculosis* 30 kDa antigen 85B protein (SEQ ID NO: 4) comprising the steps of: immunizing a mammal with a composition consisting essentially of *Mycobacterium bovis* strain Bacille Calmette-Guérin (BCG) in a primary immunization, wherein said *Mycobacterium bovis* strain BCG is not a recombinant strain BCG;
immunizing a mammal with a composition of matter comprising attenuated *Listeria monocytogenes* in a booster immunization, wherein the *Listeria monocytogenes*:
does not express a functional ActA protein (SEQ ID NO: 1);
expresses prfA protein having a G155S substitution mutation (SEQ ID NO: 3); and
expresses *Mycobacterium tuberculosis* 30 kDa antigen 85B protein (SEQ ID NO: 4);
such that an immune response to a *Mycobacterium tuberculosis* 30 kDa antigen 85B protein is generated.

12. The method of claim 11, wherein the *Listeria monocytogenes* expresses *Mycobacterium tuberculosis* 10.4 kDa EsxH protein (SEQ ID NO: 16).

13. The method of claim 11, wherein the *Listeria monocytogenes* expresses *Mycobacterium tuberculosis* 32 kDa 85A protein (SEQ ID NO: 11).

14. The method of claim 11, wherein the *Listeria monocytogenes* expresses *Mycobacterium tuberculosis* 23.5 kDa MPT64 protein (SEQ ID NO: 9).

15. The method of claim 11, wherein the *Listeria monocytogenes* expresses *Mycobacterium tuberculosis* 9.9 kDa ESAT-6 protein (SEQ ID NO: 22).

16. The method of claim 11, wherein the *Listeria monocytogenes* expresses *Mycobacterium tuberculosis* 14 kDa alpha crystalline homolog protein (SEQ ID NO: 17).

17. The method of claim 11, wherein the *Listeria monocytogenes* expresses *Mycobacterium tuberculosis* 47 kDa isocitrate lysate protein (SEQ ID NO: 18).

18. The method of claim 11, wherein the *Listeria monocytogenes* expresses *Mycobacterium tuberculosis* 7.6 kDa hypothetical protein (SEQ ID NO: 19).

19. The method of claim 11, wherein the *Mycobacterium tuberculosis* 30 kDa antigen 85B protein is coupled to a heterologous protein sequence comprising the N-terminal 100 amino acids of the ActA protein.

20. The method of claim 19, wherein the expression of the *Mycobacterium tuberculosis* 30 kDa antigen 85B protein is controlled by an ActA promoter.

* * * * *

SEQUENCE LISTING

<160> NUMBER OF SEQ ID NOS: 46

<210> SEQ ID NO 1
<211> LENGTH: 639
<212> TYPE: PRT
<213> ORGANISM: Listeria monocytogenes

<400> SEQUENCE: 1

Met Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
                20                  25                  30

Ser Glu Asp Ser Ser Leu Asn Thr Asp Glu Trp Glu Glu Lys Thr
            35                  40                  45

Glu Glu Gln Pro Ser Glu Val Asn Thr Gly Pro Arg Tyr Glu Thr Ala
        50                  55                  60

Arg Glu Val Ser Ser Arg Asp Ile Lys Glu Leu Glu Lys Ser Asn Lys
65                  70                  75                  80

Val Arg Asn Thr Asn Lys Ala Asp Leu Ile Ala Met Leu Lys Glu Lys
                85                  90                  95

Ala Glu Lys Gly Pro Asn Ile Asn Asn Asn Asn Ser Glu Gln Thr Glu
            100                 105                 110

Asn Ala Ala Ile Asn Glu Glu Ala Ser Gly Ala Asp Arg Pro Ala Ile
        115                 120                 125

Gln Val Glu Arg Arg His Pro Gly Leu Pro Ser Asp Ser Ala Ala Glu
    130                 135                 140

-continued

```
Ile Lys Lys Arg Arg Lys Ala Ile Ala Ser Ser Asp Ser Glu Leu Glu
145                 150                 155                 160

Ser Leu Thr Tyr Pro Asp Lys Pro Thr Lys Val Asn Lys Lys Lys Val
            165                 170                 175

Ala Lys Glu Ser Val Ala Asp Ala Ser Glu Ser Asp Leu Asp Ser Ser
        180                 185                 190

Met Gln Ser Ala Asp Glu Ser Ser Pro Gln Pro Leu Lys Ala Asn Gln
    195                 200                 205

Gln Pro Phe Phe Pro Lys Val Phe Lys Lys Ile Lys Asp Ala Gly Lys
    210                 215                 220

Trp Val Arg Asp Lys Ile Asp Glu Asn Pro Glu Val Lys Lys Ala Ile
225                 230                 235                 240

Val Asp Lys Ser Ala Gly Leu Ile Asp Gln Leu Leu Thr Lys Lys Lys
            245                 250                 255

Ser Glu Glu Val Asn Ala Ser Asp Phe Pro Pro Pro Thr Asp Glu
        260                 265                 270

Glu Leu Arg Leu Ala Leu Pro Glu Thr Pro Met Leu Leu Gly Phe Asn
    275                 280                 285

Ala Pro Ala Thr Ser Glu Pro Ser Ser Phe Glu Phe Pro Pro Pro
    290                 295                 300

Thr Asp Glu Glu Leu Arg Leu Ala Leu Pro Glu Thr Pro Met Leu Leu
305                 310                 315                 320

Gly Phe Asn Ala Pro Ala Thr Ser Glu Pro Ser Ser Phe Glu Phe Pro
            325                 330                 335

Pro Pro Pro Thr Glu Asp Glu Leu Glu Ile Ile Arg Glu Thr Ala Ser
        340                 345                 350

Ser Leu Asp Ser Ser Phe Thr Arg Gly Asp Leu Ala Ser Leu Arg Asn
    355                 360                 365

Ala Ile Asn Arg His Ser Gln Asn Phe Ser Asp Phe Pro Pro Ile Pro
    370                 375                 380

Thr Glu Glu Glu Leu Asn Gly Arg Gly Arg Pro Thr Ser Glu Glu
385                 390                 395                 400

Phe Ser Ser Leu Asn Ser Gly Asp Phe Thr Asp Asp Glu Asn Ser Glu
            405                 410                 415

Thr Thr Glu Glu Glu Ile Asp Arg Leu Ala Asp Leu Arg Asp Arg Gly
        420                 425                 430

Thr Gly Lys His Ser Arg Asn Ala Gly Phe Leu Pro Leu Asn Pro Phe
    435                 440                 445

Ala Ser Ser Pro Val Pro Ser Leu Ser Pro Lys Val Ser Lys Ile Ser
    450                 455                 460

Ala Pro Ala Leu Ile Ser Asp Ile Thr Lys Lys Thr Pro Phe Lys Asn
465                 470                 475                 480

Pro Ser Gln Pro Leu Asn Val Phe Asn Lys Lys Thr Thr Lys Thr
            485                 490                 495

Val Thr Lys Lys Pro Thr Pro Val Lys Thr Ala Pro Lys Leu Ala Glu
        500                 505                 510

Leu Pro Ala Thr Lys Pro Gln Glu Thr Val Leu Arg Glu Asn Lys Thr
    515                 520                 525

Pro Phe Ile Glu Lys Gln Ala Glu Thr Asn Lys Gln Ser Ile Asn Met
    530                 535                 540

Pro Ser Leu Pro Val Ile Gln Lys Glu Ala Thr Glu Ser Asp Lys Glu
545                 550                 555                 560

Glu Met Lys Pro Gln Thr Glu Glu Lys Met Val Glu Glu Ser Glu Ser
```

```
                565                 570                 575
Ala Asn Asn Ala Asn Gly Lys Asn Arg Ser Ala Gly Ile Glu Glu Gly
                580                 585                 590

Lys Leu Ile Ala Lys Ser Ala Glu Asp Glu Lys Ala Lys Glu Glu Pro
            595                 600                 605

Gly Asn His Thr Thr Leu Ile Leu Ala Met Leu Ala Ile Gly Val Phe
        610                 615                 620

Ser Leu Gly Ala Phe Ile Lys Ile Ile Gln Leu Arg Lys Asn Asn
625                 630                 635

<210> SEQ ID NO 2
<211> LENGTH: 630
<212> TYPE: PRT
<213> ORGANISM: Listeria monocytogenes

<400> SEQUENCE: 2

Met Lys Glu Lys His Asn Pro Arg Arg Lys Tyr Cys Leu Ile Ser Gly
1               5                   10                  15

Leu Ala Ile Ile Phe Ser Leu Trp Ile Ile Gly Asn Gly Ala Lys
            20                  25                  30

Val Gln Ala Glu Thr Ile Thr Val Pro Thr Pro Ile Lys Gln Ile Phe
        35                  40                  45

Ser Asp Asp Ala Phe Ala Glu Thr Ile Lys Asp Asn Leu Lys Lys Lys
50                  55                  60

Ser Val Thr Asp Ala Val Thr Gln Asn Glu Leu Asn Ser Ile Asp Gln
65                  70                  75                  80

Ile Ile Ala Asn Asn Ser Asp Ile Lys Ser Val Gln Gly Ile Gln Tyr
                85                  90                  95

Leu Pro Asn Val Thr Lys Leu Phe Leu Asn Gly Asn Lys Leu Thr Asp
            100                 105                 110

Ile Lys Pro Leu Ala Asn Leu Lys Asn Leu Gly Trp Leu Phe Leu Asp
        115                 120                 125

Glu Asn Lys Val Lys Asp Leu Ser Ser Leu Lys Asp Leu Lys Lys Leu
130                 135                 140

Lys Ser Leu Ser Leu Glu His Asn Gly Ile Ser Asp Ile Asn Gly Leu
145                 150                 155                 160

Val His Leu Pro Gln Leu Glu Ser Leu Tyr Leu Gly Asn Asn Lys Ile
                165                 170                 175

Thr Asp Ile Thr Val Leu Ser Arg Leu Thr Lys Leu Asp Thr Leu Ser
            180                 185                 190

Leu Glu Asp Asn Gln Ile Ser Asp Ile Val Pro Leu Ala Gly Leu Thr
        195                 200                 205

Lys Leu Gln Asn Leu Tyr Leu Ser Lys Asn His Ile Ser Asp Leu Arg
210                 215                 220

Ala Leu Ala Gly Leu Lys Asn Leu Asp Val Leu Glu Leu Phe Ser Gln
225                 230                 235                 240

Glu Cys Leu Asn Lys Pro Ile Asn His Gln Ser Asn Leu Val Val Pro
                245                 250                 255

Asn Thr Val Lys Asn Thr Asp Gly Ser Leu Val Thr Pro Glu Ile Ile
            260                 265                 270

Ser Asp Asp Gly Asp Tyr Glu Lys Pro Asn Val Lys Trp His Leu Pro
        275                 280                 285

Glu Phe Thr Asn Glu Val Ser Phe Ile Phe Tyr Gln Pro Val Thr Ile
    290                 295                 300
```

Gly Lys Ala Lys Ala Arg Phe His Gly Arg Val Thr Gln Pro Leu Lys
305                 310                 315                 320

Glu Val Tyr Thr Val Ser Tyr Asp Val Asp Gly Thr Val Ile Lys Thr
            325                 330                 335

Lys Val Glu Ala Gly Thr Arg Ile Thr Ala Pro Lys Pro Pro Thr Lys
        340                 345                 350

Gln Gly Tyr Val Phe Lys Gly Trp Tyr Thr Glu Lys Asn Gly Gly His
    355                 360                 365

Glu Trp Asn Phe Asn Thr Asp Tyr Met Ser Gly Asn Asp Phe Thr Leu
370                 375                 380

Tyr Ala Val Phe Lys Ala Glu Thr Thr Glu Lys Ala Val Asn Leu Thr
385                 390                 395                 400

Arg Tyr Val Lys Tyr Ile Arg Gly Asn Ala Gly Ile Tyr Lys Leu Pro
                405                 410                 415

Arg Glu Asp Asn Ser Leu Lys Gln Gly Thr Leu Ala Ser His Arg Cys
                420                 425                 430

Lys Ala Leu Thr Val Asp Arg Glu Ala Arg Asn Gly Gly Lys Leu Trp
            435                 440                 445

Tyr Arg Leu Lys Asn Ile Gly Trp Thr Lys Ala Glu Asn Leu Ser Leu
450                 455                 460

Asp Arg Tyr Asp Lys Met Glu Tyr Asp Lys Gly Val Thr Ala Tyr Ala
465                 470                 475                 480

Arg Val Arg Asn Ala Ser Gly Asn Ser Val Trp Thr Lys Pro Tyr Asn
                485                 490                 495

Thr Ala Gly Ala Lys His Val Asn Lys Leu Ser Val Tyr Gln Gly Lys
            500                 505                 510

Asn Met Arg Ile Leu Arg Glu Ala Lys Thr Pro Ile Thr Thr Trp Tyr
            515                 520                 525

Gln Phe Ser Ile Gly Gly Lys Val Ile Gly Trp Val Asp Thr Arg Ala
530                 535                 540

Leu Asn Thr Phe Tyr Lys Gln Ser Met Glu Lys Pro Thr Arg Leu Thr
545                 550                 555                 560

Arg Tyr Val Ser Ala Asn Lys Ala Gly Glu Ser Tyr Tyr Lys Val Pro
                565                 570                 575

Val Ala Asp Asn Pro Val Lys Arg Gly Thr Leu Ala Lys Tyr Lys Asn
                580                 585                 590

Gln Lys Leu Ile Val Asp Cys Gln Ala Thr Ile Glu Gly Gln Leu Trp
            595                 600                 605

Tyr Arg Ile Arg Thr Ser Ser Thr Phe Ile Gly Trp Thr Lys Ala Ala
610                 615                 620

Asn Leu Arg Ala Gln Lys
625                 630

<210> SEQ ID NO 3
<211> LENGTH: 237
<212> TYPE: PRT
<213> ORGANISM: Listeria monocytogenes

<400> SEQUENCE: 3

Met Asn Ala Gln Ala Glu Glu Phe Lys Lys Tyr Leu Glu Thr Asn Gly
1               5                   10                  15

Ile Lys Pro Lys Gln Phe His Lys Lys Glu Leu Ile Phe Asn Gln Trp
            20                  25                  30

Asp Pro Gln Glu Tyr Cys Ile Phe Leu Tyr Asp Gly Ile Thr Lys Leu
        35                  40                  45

```
Thr Ser Ile Ser Glu Asn Gly Thr Ile Met Asn Leu Gln Tyr Tyr Lys
 50                  55                  60

Gly Ala Phe Val Ile Met Ser Gly Phe Ile Asp Thr Glu Thr Ser Val
 65                  70                  75                  80

Gly Tyr Tyr Asn Leu Glu Val Ile Ser Glu Gln Ala Thr Ala Tyr Val
                 85                  90                  95

Ile Lys Ile Asn Glu Leu Lys Glu Leu Leu Ser Lys Asn Leu Thr His
                100                 105                 110

Phe Phe Tyr Val Phe Gln Thr Leu Gln Lys Gln Val Ser Tyr Ser Leu
                115                 120                 125

Ala Lys Phe Asn Asp Phe Ser Ile Asn Gly Lys Leu Gly Ser Ile Cys
130                 135                 140

Gly Gln Leu Leu Ile Leu Thr Tyr Val Tyr Gly Lys Glu Thr Pro Asp
145                 150                 155                 160

Gly Ile Lys Ile Thr Leu Asp Asn Leu Thr Met Gln Glu Leu Gly Tyr
                165                 170                 175

Ser Ser Gly Ile Ala His Ser Ser Ala Val Ser Arg Ile Ile Ser Lys
                180                 185                 190

Leu Lys Gln Glu Lys Val Ile Val Tyr Lys Asn Ser Cys Phe Tyr Val
                195                 200                 205

Gln Asn Leu Asp Tyr Leu Lys Arg Tyr Ala Pro Lys Leu Asp Glu Trp
210                 215                 220

Phe Tyr Leu Ala Cys Pro Ala Thr Trp Gly Lys Leu Asn
225                 230                 235
```

```
<210> SEQ ID NO 4
<211> LENGTH: 325
<212> TYPE: PRT
<213> ORGANISM: Mycobacterium tuberculosis

<400> SEQUENCE: 4

Met Thr Asp Val Ser Arg Lys Ile Arg Ala Trp Gly Arg Arg Leu Met
  1               5                  10                  15

Ile Gly Thr Ala Ala Ala Val Val Leu Pro Gly Leu Val Gly Leu Ala
                 20                  25                  30

Gly Gly Ala Ala Thr Ala Gly Ala Phe Ser Arg Pro Gly Leu Pro Val
                 35                  40                  45

Glu Tyr Leu Gln Val Pro Ser Pro Ser Met Gly Arg Asp Ile Lys Val
 50                  55                  60

Gln Phe Gln Ser Gly Gly Asn Asn Ser Pro Ala Val Tyr Leu Leu Asp
 65                  70                  75                  80

Gly Leu Arg Ala Gln Asp Asp Tyr Asn Gly Trp Asp Ile Asn Thr Pro
                 85                  90                  95

Ala Phe Glu Trp Tyr Tyr Gln Ser Gly Leu Ser Ile Val Met Pro Val
                100                 105                 110

Gly Gly Gln Ser Ser Phe Tyr Ser Asp Trp Tyr Ser Pro Ala Cys Gly
                115                 120                 125

Lys Ala Gly Cys Gln Thr Tyr Lys Trp Glu Thr Phe Leu Thr Ser Glu
130                 135                 140

Leu Pro Gln Trp Leu Ser Ala Asn Arg Ala Val Lys Pro Thr Gly Ser
145                 150                 155                 160

Ala Ala Ile Gly Leu Ser Met Ala Gly Ser Ser Ala Met Ile Leu Ala
                165                 170                 175

Ala Tyr His Pro Gln Gln Phe Ile Tyr Ala Gly Ser Leu Ser Ala Leu
```

```
                180                 185                 190
Leu Asp Pro Ser Gln Gly Met Gly Pro Ser Leu Ile Gly Leu Ala Met
            195                 200                 205

Gly Asp Ala Gly Gly Tyr Lys Ala Ala Asp Met Trp Gly Pro Ser Ser
        210                 215                 220

Asp Pro Ala Trp Glu Arg Asn Asp Pro Thr Gln Gln Ile Pro Lys Leu
225                 230                 235                 240

Val Ala Asn Asn Thr Arg Leu Trp Val Tyr Cys Gly Asn Gly Thr Pro
            245                 250                 255

Asn Glu Leu Gly Gly Ala Asn Ile Pro Ala Glu Phe Leu Glu Asn Phe
        260                 265                 270

Val Arg Ser Ser Asn Leu Lys Phe Gln Asp Ala Tyr Asn Ala Ala Gly
        275                 280                 285

Gly His Asn Ala Val Phe Asn Phe Pro Pro Asn Gly Thr His Ser Trp
        290                 295                 300

Glu Tyr Trp Gly Ala Gln Leu Asn Ala Met Lys Gly Asp Leu Gln Ser
305                 310                 315                 320

Ser Leu Gly Ala Gly
            325

<210> SEQ ID NO 5
<211> LENGTH: 110
<212> TYPE: PRT
<213> ORGANISM: Mycobacterium tuberculosis

<400> SEQUENCE: 5

Phe Asp Thr Arg Leu Met Arg Leu Glu Asp Glu Met Lys Glu Gly Arg
1               5                   10                  15

Tyr Glu Val Arg Ala Glu Leu Pro Gly Val Asp Pro Asp Lys Asp Val
            20                  25                  30

Asp Ile Met Val Arg Asp Gly Gln Leu Thr Ile Lys Ala Glu Arg Thr
        35                  40                  45

Glu Gln Lys Asp Phe Asp Gly Arg Ser Glu Phe Ala Tyr Gly Ser Phe
    50                  55                  60

Val Arg Thr Val Ser Leu Pro Val Gly Ala Asp Glu Asp Asp Ile Lys
65                  70                  75                  80

Ala Thr Tyr Asp Lys Gly Ile Leu Thr Val Ser Val Ala Val Ser Glu
                85                  90                  95

Gly Lys Pro Thr Glu Lys His Ile Gln Ile Arg Ser Thr Asn
            100                 105                 110

<210> SEQ ID NO 6
<211> LENGTH: 173
<212> TYPE: PRT
<213> ORGANISM: Mycobacterium tuberculosis

<400> SEQUENCE: 6

Met Ser Leu Arg Leu Val Ser Pro Ile Lys Ala Phe Ala Asp Gly Ile
1               5                   10                  15

Val Ala Val Ala Ile Ala Val Val Leu Met Phe Gly Leu Ala Asn Thr
            20                  25                  30

Pro Arg Ala Val Ala Ala Asp Glu Arg Leu Gln Phe Thr Ala Thr Thr
        35                  40                  45

Leu Ser Gly Ala Pro Phe Asp Gly Ala Ser Leu Gln Gly Lys Pro Ala
    50                  55                  60

Val Leu Trp Phe Trp Thr Pro Trp Cys Pro Phe Cys Asn Ala Glu Ala
```

```
65                  70                  75                  80

Pro Ser Leu Ser Gln Val Ala Ala Ala Asn Pro Ala Val Thr Phe Val
                85                  90                  95

Gly Ile Ala Thr Arg Ala Asp Val Gly Ala Met Gln Ser Phe Val Ser
            100                 105                 110

Lys Tyr Asn Leu Asn Phe Thr Asn Leu Asn Asp Ala Asp Gly Val Ile
        115                 120                 125

Trp Ala Arg Tyr Asn Val Pro Trp Gln Pro Ala Phe Val Phe Tyr Arg
    130                 135                 140

Ala Asp Gly Thr Ser Thr Phe Val Asn Asn Pro Thr Ala Ala Met Ser
145                 150                 155                 160

Gln Asp Glu Leu Ser Gly Arg Val Ala Ala Leu Thr Ser
                165                 170

<210> SEQ ID NO 7
<211> LENGTH: 159
<212> TYPE: PRT
<213> ORGANISM: Mycobacterium tuberculosis

<400> SEQUENCE: 7

Met  Lys Leu Thr Thr Met Ile Lys Thr Ala Val Ala Val Val Ala Met
 1               5                  10                  15

Ala Ala Ile Ala Thr Phe Ala Ala Pro Val Ala Leu Ala Ala Tyr Pro
            20                  25                  30

Ile Thr Gly Lys Leu Gly Ser Glu Leu Thr Met Thr Asp Thr Val Gly
        35                  40                  45

Gln Val Val Leu Gly Trp Lys Val Ser Asp Leu Lys Ser Ser Thr Ala
    50                  55                  60

Val Ile Pro Gly Tyr Pro Val Ala Gly Gln Val Trp Glu Ala Thr Ala
65                  70                  75                  80

Thr Val Asn Ala Ile Arg Gly Ser Val Thr Pro Ala Val Ser Gln Phe
                85                  90                  95

Asn Ala Arg Thr Ala Asp Gly Ile Asn Tyr Arg Val Leu Trp Gln Ala
            100                 105                 110

Ala Gly Pro Asp Thr Ile Ser Gly Ala Thr Ile Pro Gln Gly Glu Gln
        115                 120                 125

Ser Thr Gly Lys Ile Tyr Phe Asp Val Thr Gly Pro Ser Pro Thr Ile
    130                 135                 140

Val Ala Met Asn Asn Gly Met Glu Asp Leu Leu Ile Trp Glu Pro
145                 150                 155

<210> SEQ ID NO 8
<211> LENGTH: 207
<212> TYPE: PRT
<213> ORGANISM: Mycobacterium tuberculosis

<400> SEQUENCE: 8

Val Ala Glu Tyr Thr Leu Pro Asp Leu Asp Trp Asp Tyr Gly Ala Leu
 1               5                  10                  15

Glu Pro His Ile Ser Gly Gln Ile Asn Glu Leu His His Ser Lys His
            20                  25                  30

His Ala Thr Tyr Val Lys Gly Ala Asn Asp Ala Val Ala Lys Leu Glu
        35                  40                  45

Glu Ala Arg Ala Lys Glu Asp His Ser Ala Ile Leu Leu Asn Glu Lys
    50                  55                  60

Asn Leu Ala Phe Asn Leu Ala Gly His Val Asn His Thr Ile Trp Trp
```

```
                65                  70                  75                  80
Lys Asn Leu Ser Pro Asn Gly Gly Asp Lys Pro Thr Gly Glu Leu Ala
                    85                  90                  95

Ala Ala Ile Ala Asp Ala Phe Gly Ser Phe Asp Lys Phe Arg Ala Gln
                100                 105                 110

Phe His Ala Ala Ala Thr Thr Val Gln Gly Ser Gly Trp Ala Ala Leu
                115                 120                 125

Gly Trp Asp Thr Leu Gly Asn Lys Leu Leu Ile Phe Gln Val Tyr Asp
    130                 135                 140

His Gln Thr Asn Phe Pro Leu Gly Ile Val Pro Leu Leu Leu Leu Asp
145                 150                 155                 160

Met Trp Glu His Ala Phe Tyr Leu Gln Tyr Lys Asn Val Lys Val Asp
                165                 170                 175

Phe Ala Lys Ala Phe Trp Asn Val Val Asn Trp Ala Asp Val Gln Ser
                180                 185                 190

Arg Tyr Ala Ala Ala Thr Ser Gln Thr Lys Gly Leu Ile Phe Gly
                195                 200                 205

<210> SEQ ID NO 9
<211> LENGTH: 228
<212> TYPE: PRT
<213> ORGANISM: Mycobacterium tuberculosis

<400> SEQUENCE: 9

Val Arg Ile Lys Ile Phe Met Leu Val Thr Ala Val Val Leu Leu Cys
1               5                   10                  15

Cys Ser Gly Val Ala Thr Ala Ala Pro Lys Thr Tyr Cys Glu Glu Leu
                20                  25                  30

Lys Gly Thr Asp Thr Gly Gln Ala Cys Gln Ile Gln Met Ser Asp Pro
            35                  40                  45

Ala Tyr Asn Ile Asn Ile Ser Leu Pro Ser Tyr Tyr Pro Asp Gln Lys
    50                  55                  60

Ser Leu Glu Asn Tyr Ile Ala Gln Thr Arg Asp Lys Phe Leu Ser Ala
65                  70                  75                  80

Ala Thr Ser Ser Thr Pro Arg Glu Ala Pro Tyr Glu Leu Asn Ile Thr
                85                  90                  95

Ser Ala Thr Tyr Gln Ser Ala Ile Pro Pro Arg Gly Thr Gln Ala Val
                100                 105                 110

Val Leu Lys Val Tyr Gln Asn Ala Gly Gly Thr His Pro Thr Thr Thr
            115                 120                 125

Tyr Lys Ala Phe Asp Trp Asp Gln Ala Tyr Arg Lys Pro Ile Thr Tyr
    130                 135                 140

Asp Thr Leu Trp Gln Ala Asp Thr Asp Pro Leu Pro Val Val Phe Pro
145                 150                 155                 160

Ile Val Gln Gly Glu Leu Ser Lys Gln Thr Gly Gln Gln Val Ser Ile
                165                 170                 175

Ala Pro Asn Ala Gly Leu Asp Pro Val Asn Tyr Gln Asn Phe Ala Val
                180                 185                 190

Thr Asn Asp Gly Val Ile Phe Phe Asn Pro Gly Glu Leu Leu Pro
            195                 200                 205

Glu Ala Ala Gly Pro Thr Gln Val Leu Val Pro Arg Ser Ala Ile Asp
    210                 215                 220

Ser Met Leu Ala
225
```

<210> SEQ ID NO 10
<211> LENGTH: 299
<212> TYPE: PRT
<213> ORGANISM: Mycobacterium tuberculosis

<400> SEQUENCE: 10

```
Met Lys Gly Arg Ser Ala Leu Leu Arg Ala Leu Trp Ile Ala Ala Leu
1               5                   10                  15

Ser Phe Gly Leu Gly Gly Val Ala Val Ala Ala Glu Pro Thr Ala Lys
            20                  25                  30

Ala Ala Pro Tyr Glu Asn Leu Met Val Pro Ser Pro Ser Met Gly Arg
        35                  40                  45

Asp Ile Pro Val Ala Phe Leu Ala Gly Gly Pro His Ala Val Tyr Leu
    50                  55                  60

Leu Asp Ala Phe Asn Ala Gly Pro Asp Val Ser Asn Trp Val Thr Ala
65                  70                  75                  80

Gly Asn Ala Met Asn Thr Leu Ala Gly Lys Gly Ile Ser Val Val Ala
                85                  90                  95

Pro Ala Gly Gly Ala Tyr Ser Met Tyr Thr Asn Trp Glu Gln Asp Gly
            100                 105                 110

Ser Lys Gln Trp Asp Thr Phe Leu Ser Ala Glu Leu Pro Asp Trp Leu
        115                 120                 125

Ala Ala Asn Arg Gly Leu Ala Pro Gly Gly His Ala Val Gly Ala
    130                 135                 140

Ala Gln Gly Gly Tyr Gly Ala Met Ala Leu Ala Ala Phe His Pro Asp
145                 150                 155                 160

Arg Phe Gly Phe Ala Gly Ser Met Ser Gly Phe Leu Tyr Pro Ser Asn
                165                 170                 175

Thr Thr Thr Asn Gly Ala Ile Ala Ala Gly Met Gln Gln Phe Gly Gly
            180                 185                 190

Val Asp Thr Asn Gly Met Trp Gly Ala Pro Gln Leu Gly Arg Trp Lys
        195                 200                 205

Trp His Asp Pro Trp Val His Ala Ser Leu Leu Ala Gln Asn Asn Thr
    210                 215                 220

Arg Val Trp Val Trp Ser Pro Thr Asn Pro Gly Ala Ser Asp Pro Ala
225                 230                 235                 240

Ala Met Ile Gly Gln Ala Ala Glu Ala Met Gly Asn Ser Arg Met Phe
                245                 250                 255

Tyr Asn Gln Tyr Arg Ser Val Gly Gly His Asn Gly His Phe Asp Phe
            260                 265                 270

Pro Ala Ser Gly Asp Asn Gly Trp Gly Ser Trp Ala Pro Gln Leu Gly
        275                 280                 285

Ala Met Ser Gly Asp Ile Val Gly Ala Ile Arg
    290                 295
```

<210> SEQ ID NO 11
<211> LENGTH: 338
<212> TYPE: PRT
<213> ORGANISM: Mycobacterium tuberculosis

<400> SEQUENCE: 11

```
Met Gln Leu Val Asp Arg Val Arg Gly Ala Val Thr Gly Met Ser Arg
1               5                   10                  15

Arg Leu Val Val Gly Ala Val Gly Ala Ala Leu Val Ser Gly Leu Val
            20                  25                  30
```

```
Gly Ala Val Gly Gly Thr Ala Thr Ala Gly Ala Phe Ser Arg Pro Gly
             35                  40                  45

Leu Pro Val Glu Tyr Leu Gln Val Pro Ser Pro Ser Met Gly Arg Asp
 50                  55                  60

Ile Lys Val Gln Phe Gln Ser Gly Gly Ala Asn Ser Pro Ala Leu Tyr
 65                  70                  75                  80

Leu Leu Asp Gly Leu Arg Ala Gln Asp Phe Ser Gly Trp Asp Ile
                 85                  90                  95

Asn Thr Pro Ala Phe Glu Trp Tyr Asp Gln Ser Gly Leu Ser Val Val
                100                 105                 110

Met Pro Val Gly Gly Gln Ser Ser Phe Tyr Ser Asp Trp Tyr Gln Pro
            115                 120                 125

Ala Cys Gly Lys Ala Gly Cys Gln Thr Tyr Lys Trp Glu Thr Phe Leu
            130                 135                 140

Thr Ser Glu Leu Pro Gly Trp Leu Gln Ala Asn Arg His Val Lys Pro
145                 150                 155                 160

Thr Gly Ser Ala Val Val Gly Leu Ser Met Ala Ala Ser Ser Ala Leu
                165                 170                 175

Thr Leu Ala Ile Tyr His Pro Gln Gln Phe Val Tyr Ala Gly Ala Met
            180                 185                 190

Ser Gly Leu Leu Asp Pro Ser Gln Ala Met Gly Pro Thr Leu Ile Gly
            195                 200                 205

Leu Ala Met Gly Asp Ala Gly Gly Tyr Lys Ala Ser Asp Met Trp Gly
210                 215                 220

Pro Lys Glu Asp Pro Ala Trp Gln Arg Asn Asp Pro Leu Leu Asn Val
225                 230                 235                 240

Gly Lys Leu Ile Ala Asn Asn Thr Arg Val Trp Val Tyr Cys Gly Asn
                245                 250                 255

Gly Lys Pro Ser Asp Leu Gly Gly Asn Asn Leu Pro Ala Lys Phe Leu
            260                 265                 270

Glu Gly Phe Val Arg Thr Ser Asn Ile Lys Phe Gln Asp Ala Tyr Asn
            275                 280                 285

Ala Gly Gly Gly His Asn Gly Val Phe Asp Phe Pro Asp Ser Gly Thr
        290                 295                 300

His Ser Trp Glu Tyr Trp Gly Ala Gln Leu Asn Ala Met Lys Pro Asp
305                 310                 315                 320

Leu Gln Arg Ala Leu Gly Ala Thr Pro Asn Thr Gly Pro Ala Pro Gln
                325                 330                 335

Gly Ala

<210> SEQ ID NO 12
<211> LENGTH: 464
<212> TYPE: PRT
<213> ORGANISM: Mycobacterium tuberculosis

<400> SEQUENCE: 12

Met Ala Lys Leu Ala Arg Val Val Gly Leu Val Gln Glu Glu Gln Pro
 1               5                  10                  15

Ser Asp Met Thr Asn His Pro Arg Tyr Ser Pro Pro Gln Gln Pro
                20                  25                  30

Gly Thr Pro Gly Tyr Ala Gln Gly Gln Gln Thr Tyr Ser Gln Gln
             35                  40                  45

Phe Asp Trp Arg Tyr Pro Pro Ser Pro Pro Gln Pro Thr Gln Tyr
 50                  55                  60
```

-continued

```
Arg Gln Pro Tyr Glu Ala Leu Gly Gly Thr Arg Pro Gly Leu Ile Pro
 65                  70                  75                  80

Gly Val Ile Pro Thr Met Thr Pro Pro Gly Met Val Arg Gln Arg
             85                  90                  95

Pro Arg Ala Gly Met Leu Ala Ile Gly Ala Val Thr Ile Ala Val Val
            100                 105                 110

Ser Ala Gly Ile Gly Gly Ala Ala Ser Leu Val Gly Phe Asn Arg
            115                 120                 125

Ala Pro Ala Gly Pro Ser Gly Pro Val Ala Ser Ala Ala Pro
        130                 135                 140

Ser Ile Pro Ala Ala Asn Met Pro Pro Gly Ser Val Glu Gln Val Ala
145                 150                 155                 160

Ala Lys Val Val Pro Ser Val Val Met Leu Glu Thr Asp Leu Gly Arg
                165                 170                 175

Gln Ser Glu Glu Gly Ser Gly Ile Ile Leu Ser Ala Glu Gly Leu Ile
            180                 185                 190

Leu Thr Asn Asn His Val Ile Ala Ala Ala Lys Pro Pro Leu Gly
            195                 200                 205

Ser Pro Pro Pro Lys Thr Thr Val Thr Phe Ser Asp Gly Arg Thr Ala
210                 215                 220

Pro Phe Thr Val Val Gly Ala Asp Pro Thr Ser Asp Ile Ala Val Val
225                 230                 235                 240

Arg Val Gln Gly Val Ser Gly Leu Thr Pro Ile Ser Leu Gly Ser Ser
                245                 250                 255

Ser Asp Leu Arg Val Gly Gln Pro Val Leu Ala Ile Gly Ser Pro Leu
            260                 265                 270

Gly Leu Glu Gly Thr Val Thr Thr Gly Ile Val Ser Ala Leu Asn Arg
            275                 280                 285

Pro Val Ser Thr Thr Gly Glu Ala Gly Asn Gln Asn Thr Val Leu Asp
290                 295                 300

Ala Ile Gln Thr Asp Ala Ala Ile Asn Pro Gly Asn Ser Gly Gly Ala
305                 310                 315                 320

Leu Val Asn Met Asn Ala Gln Leu Val Gly Val Asn Ser Ala Ile Ala
                325                 330                 335

Thr Leu Gly Ala Asp Ser Ala Asp Ala Gln Ser Gly Ser Ile Gly Leu
            340                 345                 350

Gly Phe Ala Ile Pro Val Asp Gln Ala Lys Arg Ile Ala Asp Glu Leu
            355                 360                 365

Ile Ser Thr Gly Lys Ala Ser His Ala Ser Leu Gly Val Gln Val Thr
370                 375                 380

Asn Asp Lys Asp Thr Leu Gly Ala Lys Ile Val Glu Val Val Ala Gly
385                 390                 395                 400

Gly Ala Ala Ala Asn Ala Gly Val Pro Lys Gly Val Val Thr Lys
                405                 410                 415

Val Asp Asp Arg Pro Ile Asn Ser Ala Asp Ala Leu Val Ala Ala Val
            420                 425                 430

Arg Ser Lys Ala Pro Gly Ala Thr Val Ala Leu Thr Phe Gln Asp Pro
            435                 440                 445

Ser Gly Gly Ser Arg Thr Val Gln Val Thr Leu Gly Lys Ala Glu Gln
450                 455                 460

<210> SEQ ID NO 13
<211> LENGTH: 325
<212> TYPE: PRT
```

<213> ORGANISM: Mycobacterium tuberculosis

<400> SEQUENCE: 13

Met His Gln Val Asp Pro Asn Leu Thr Arg Arg Lys Gly Arg Leu Ala
1 5 10 15

Ala Leu Ala Ile Ala Ala Met Ala Ser Ala Ser Leu Val Thr Val Ala
20 25 30

Val Pro Ala Thr Ala Asn Ala Asp Pro Glu Pro Ala Pro Pro Val Pro
35 40 45

Thr Thr Ala Ala Ser Pro Pro Ser Thr Ala Ala Ala Pro Pro Ala Pro
50 55 60

Ala Thr Pro Val Ala Pro Pro Pro Pro Ala Ala Ala Asn Thr Pro Asn
65 70 75 80

Ala Gln Pro Gly Asp Pro Asn Ala Ala Pro Pro Pro Ala Asp Pro Asn
85 90 95

Ala Pro Pro Pro Pro Val Ile Ala Pro Asn Ala Pro Gln Pro Val Arg
100 105 110

Ile Asp Asn Pro Val Gly Gly Phe Ser Phe Ala Leu Pro Ala Gly Trp
115 120 125

Val Glu Ser Asp Ala Ala His Phe Asp Tyr Gly Ser Ala Leu Leu Ser
130 135 140

Lys Thr Thr Gly Asp Pro Pro Phe Pro Gly Gln Pro Pro Pro Val Ala
145 150 155 160

Asn Asp Thr Arg Ile Val Leu Gly Arg Leu Asp Gln Lys Leu Tyr Ala
165 170 175

Ser Ala Glu Ala Thr Asp Ser Lys Ala Ala Ala Arg Leu Gly Ser Asp
180 185 190

Met Gly Glu Phe Tyr Met Pro Tyr Pro Gly Thr Arg Ile Asn Gln Glu
195 200 205

Thr Val Ser Leu Asp Ala Asn Gly Val Ser Gly Ser Ala Ser Tyr Tyr
210 215 220

Glu Val Lys Phe Ser Asp Pro Ser Lys Pro Asn Gly Gln Ile Trp Thr
225 230 235 240

Gly Val Ile Gly Ser Pro Ala Ala Asn Ala Pro Asp Ala Gly Pro Pro
245 250 255

Gln Arg Trp Phe Val Val Trp Leu Gly Thr Ala Asn Asn Pro Val Asp
260 265 270

Lys Gly Ala Ala Lys Ala Leu Ala Glu Ser Ile Arg Pro Leu Val Ala
275 280 285

Pro Pro Pro Ala Pro Ala Pro Ala Pro Ala Glu Pro Ala Pro Ala Pro
290 295 300

Ala Pro Ala Gly Glu Val Ala Pro Thr Pro Thr Thr Pro Thr Pro Gln
305 310 315 320

Arg Thr Leu Pro Ala
325

<210> SEQ ID NO 14
<211> LENGTH: 478
<212> TYPE: PRT
<213> ORGANISM: Mycobacterium tuberculosis

<400> SEQUENCE: 14

Val Thr Glu Lys Thr Pro Asp Asp Val Phe Lys Leu Ala Lys Asp Glu
1 5 10 15

Lys Val Glu Tyr Val Asp Val Arg Phe Cys Asp Leu Pro Gly Ile Met

```
            20                  25                  30
Gln His Phe Thr Ile Pro Ala Ser Ala Phe Asp Lys Ser Val Phe Asp
                35                  40                  45
Asp Gly Leu Ala Phe Asp Gly Ser Ser Ile Arg Gly Phe Gln Ser Ile
         50                  55                  60
His Glu Ser Asp Met Leu Leu Pro Asp Pro Glu Thr Ala Arg Ile
 65                  70                  75                  80
Asp Pro Phe Arg Ala Ala Lys Thr Leu Asn Ile Asn Phe Phe Val His
                 85                  90                  95
Asp Pro Phe Thr Leu Glu Pro Tyr Ser Arg Asp Pro Arg Asn Ile Ala
            100                 105                 110
Arg Lys Ala Glu Asn Tyr Leu Ile Ser Thr Gly Ile Ala Asp Thr Ala
            115                 120                 125
Tyr Phe Gly Ala Glu Ala Glu Phe Tyr Ile Phe Asp Ser Val Ser Phe
            130                 135                 140
Asp Ser Arg Ala Asn Gly Ser Phe Tyr Glu Val Asp Ala Ile Ser Gly
145                 150                 155                 160
Trp Trp Asn Thr Gly Ala Ala Thr Glu Ala Asp Gly Ser Pro Asn Arg
                165                 170                 175
Gly Tyr Lys Val Arg His Lys Gly Gly Tyr Phe Pro Val Ala Pro Asn
                180                 185                 190
Asp Gln Tyr Val Asp Leu Arg Asp Lys Met Leu Thr Asn Leu Ile Asn
                195                 200                 205
Ser Gly Phe Ile Leu Glu Lys Gly His His Glu Val Gly Ser Gly Gly
    210                 215                 220
Gln Ala Glu Ile Asn Tyr Gln Phe Asn Ser Leu Leu His Ala Ala Asp
225                 230                 235                 240
Asp Met Gln Leu Tyr Lys Tyr Ile Ile Lys Asn Thr Ala Trp Gln Asn
                245                 250                 255
Gly Lys Thr Val Thr Phe Met Pro Lys Pro Leu Phe Gly Asp Asn Gly
                260                 265                 270
Ser Gly Met His Cys His Gln Ser Leu Trp Lys Asp Gly Ala Pro Leu
                275                 280                 285
Met Tyr Asp Glu Thr Gly Tyr Ala Gly Leu Ser Asp Thr Ala Arg His
            290                 295                 300
Tyr Ile Gly Gly Leu Leu His His Ala Pro Ser Leu Leu Ala Phe Thr
305                 310                 315                 320
Asn Pro Thr Val Asn Ser Tyr Lys Arg Leu Val Pro Gly Tyr Glu Ala
                325                 330                 335
Pro Ile Asn Leu Val Tyr Ser Gln Arg Asn Arg Ser Ala Cys Val Arg
            340                 345                 350
Ile Pro Ile Thr Gly Ser Asn Pro Lys Ala Lys Arg Leu Glu Phe Arg
            355                 360                 365
Ser Pro Asp Ser Ser Gly Asn Pro Tyr Leu Ala Phe Ser Ala Met Leu
    370                 375                 380
Met Ala Gly Leu Asp Gly Ile Lys Asn Lys Ile Glu Pro Gln Ala Pro
385                 390                 395                 400
Val Asp Lys Asp Leu Tyr Glu Leu Pro Pro Glu Glu Ala Ala Ser Ile
                405                 410                 415
Pro Gln Thr Pro Thr Gln Leu Ser Asp Val Ile Asp Arg Leu Glu Ala
            420                 425                 430
Asp His Glu Tyr Leu Thr Glu Gly Gly Val Phe Thr Asn Asp Leu Ile
            435                 440                 445
```

```
Glu Thr Trp Ile Ser Phe Lys Arg Glu Asn Glu Ile Glu Pro Val Asn
    450                 455                 460
Ile Arg Pro His Pro Tyr Glu Phe Ala Leu Tyr Tyr Asp Val
465                 470                 475
```

<210> SEQ ID NO 15
<211> LENGTH: 625
<212> TYPE: PRT
<213> ORGANISM: Mycobacterium tuberculosis

<400> SEQUENCE: 15

```
Met Ala Arg Ala Val Gly Ile Asp Leu Gly Thr Thr Asn Ser Val Val
1               5                   10                  15

Ser Val Leu Glu Gly Gly Asp Pro Val Val Ala Asn Ser Glu Gly
            20                  25                  30

Ser Arg Thr Thr Pro Ser Ile Val Ala Phe Ala Arg Asn Gly Glu Val
            35                  40                  45

Leu Val Gly Gln Pro Ala Lys Asn Gln Ala Val Thr Asn Val Asp Arg
        50                  55                  60

Thr Val Arg Ser Val Lys Arg His Met Gly Ser Asp Trp Ser Ile Glu
65                  70                  75                  80

Ile Asp Gly Lys Lys Tyr Thr Ala Pro Glu Ile Ser Ala Arg Ile Leu
                85                  90                  95

Met Lys Leu Lys Arg Asp Ala Glu Ala Tyr Leu Gly Glu Asp Ile Thr
            100                 105                 110

Asp Ala Val Ile Thr Thr Pro Ala Tyr Phe Asn Asp Ala Gln Arg Gln
            115                 120                 125

Ala Thr Lys Asp Ala Gly Gln Ile Ala Gly Leu Asn Val Leu Arg Ile
        130                 135                 140

Val Asn Glu Pro Thr Ala Ala Ala Leu Ala Tyr Gly Leu Asp Lys Gly
145                 150                 155                 160

Glu Lys Glu Gln Arg Ile Leu Val Phe Asp Leu Gly Gly Gly Thr Phe
                165                 170                 175

Asp Val Ser Leu Leu Glu Ile Gly Glu Gly Val Val Glu Val Arg Ala
            180                 185                 190

Thr Ser Gly Asp Asn His Leu Gly Gly Asp Asp Trp Asp Gln Arg Val
        195                 200                 205

Val Asp Trp Leu Val Asp Lys Phe Lys Gly Thr Ser Gly Ile Asp Leu
    210                 215                 220

Thr Lys Asp Lys Met Ala Met Gln Arg Leu Arg Glu Ala Ala Glu Lys
225                 230                 235                 240

Ala Lys Ile Glu Leu Ser Ser Ser Gln Ser Thr Ser Ile Asn Leu Pro
                245                 250                 255

Tyr Ile Thr Val Asp Ala Asp Lys Asn Pro Leu Phe Leu Asp Glu Gln
            260                 265                 270

Leu Thr Arg Ala Glu Phe Gln Arg Ile Thr Gln Asp Leu Leu Asp Arg
        275                 280                 285

Thr Arg Lys Pro Phe Gln Ser Val Ile Ala Thr Gly Ile Ser Val
    290                 295                 300

Ser Glu Ile Asp His Val Val Leu Val Gly Gly Ser Thr Arg Met Pro
305                 310                 315                 320

Ala Val Thr Asp Leu Val Lys Glu Leu Thr Gly Gly Lys Glu Pro Asn
                325                 330                 335

Lys Gly Val Asn Pro Asp Glu Val Val Ala Val Gly Ala Ala Leu Gln
```

```
            340                 345                 350
Ala Gly Val Leu Lys Gly Glu Val Lys Asp Val Leu Leu Asp Val
        355                 360                 365

Thr Pro Leu Ser Leu Gly Ile Glu Thr Lys Gly Gly Val Met Thr Arg
    370                 375                 380

Leu Ile Glu Arg Asn Thr Thr Ile Pro Thr Lys Arg Ser Glu Thr Phe
385                 390                 395                 400

Thr Thr Ala Asp Asp Asn Gln Pro Ser Val Gln Ile Gln Val Tyr Gln
                405                 410                 415

Gly Glu Arg Glu Ile Ala Ala His Asn Lys Leu Leu Gly Ser Phe Glu
            420                 425                 430

Leu Thr Gly Ile Pro Pro Ala Pro Arg Gly Ile Pro Gln Ile Glu Val
        435                 440                 445

Thr Phe Asp Ile Asp Ala Asn Gly Ile Val His Val Thr Ala Lys Asp
    450                 455                 460

Lys Gly Thr Gly Lys Glu Asn Thr Ile Arg Ile Gln Glu Gly Ser Gly
465                 470                 475                 480

Leu Ser Lys Glu Asp Ile Asp Arg Met Ile Lys Asp Ala Glu Ala His
                485                 490                 495

Ala Glu Glu Asp Arg Lys Arg Arg Glu Ala Asp Val Arg Asn Gln
            500                 505                 510

Ala Glu Thr Leu Val Tyr Gln Thr Glu Lys Phe Val Lys Glu Gln Arg
        515                 520                 525

Glu Ala Glu Gly Gly Ser Lys Val Pro Glu Asp Thr Leu Asn Lys Val
    530                 535                 540

Asp Ala Ala Val Ala Glu Ala Lys Ala Ala Leu Gly Gly Ser Asp Ile
545                 550                 555                 560

Ser Ala Ile Lys Ser Ala Met Glu Lys Leu Gly Gln Glu Ser Gln Ala
                565                 570                 575

Leu Gly Gln Ala Ile Tyr Glu Ala Ala Gln Ala Ala Ser Gln Ala Thr
            580                 585                 590

Gly Ala Ala His Pro Gly Gly Glu Pro Gly Gly Ala His Pro Gly Ser
        595                 600                 605

Ala Asp Asp Val Val Asp Ala Glu Val Val Asp Gly Arg Glu Ala
    610                 615                 620

Lys
625

<210> SEQ ID NO 16
<211> LENGTH: 96
<212> TYPE: PRT
<213> ORGANISM: Mycobacterium tuberculosis

<400> SEQUENCE: 16

Met Ser Gln Ile Met Tyr Asn Tyr Pro Ala Met Leu Gly His Ala Gly
1               5                   10                  15

Asp Met Ala Gly Tyr Ala Gly Thr Leu Gln Ser Leu Gly Ala Glu Ile
            20                  25                  30

Ala Val Glu Gln Ala Ala Leu Gln Ser Ala Trp Gln Gly Asp Thr Gly
        35                  40                  45

Ile Thr Tyr Gln Ala Trp Gln Ala Gln Trp Asn Gln Ala Met Glu Asp
    50                  55                  60

Leu Val Arg Ala Tyr His Ala Met Ser Ser Thr His Glu Ala Asn Thr
65                  70                  75                  80
```

```
Met Ala Met Met Ala Arg Asp Thr Ala Glu Ala Ala Lys Trp Gly Gly
                85                  90                  95
```

<210> SEQ ID NO 17
<211> LENGTH: 144
<212> TYPE: PRT
<213> ORGANISM: Mycobacterium tuberculosis

<400> SEQUENCE: 17

```
Met Ala Thr Thr Leu Pro Val Gln Arg His Pro Arg Ser Leu Phe Pro
  1               5                  10                  15

Glu Phe Ser Glu Leu Phe Ala Ala Phe Pro Ser Phe Ala Gly Leu Arg
                 20                  25                  30

Pro Thr Phe Asp Thr Arg Leu Met Arg Leu Glu Asp Glu Met Lys Glu
             35                  40                  45

Gly Arg Tyr Glu Val Arg Ala Glu Leu Pro Gly Val Asp Pro Asp Lys
         50                  55                  60

Asp Val Asp Ile Met Val Arg Asp Gly Gln Leu Thr Ile Lys Ala Glu
 65                  70                  75                  80

Arg Thr Glu Gln Lys Asp Phe Asp Gly Arg Ser Glu Phe Ala Tyr Gly
                 85                  90                  95

Ser Phe Val Arg Thr Val Ser Leu Pro Val Gly Ala Asp Glu Asp Asp
                100                 105                 110

Ile Lys Ala Thr Tyr Asp Lys Gly Ile Leu Thr Val Ser Val Ala Val
            115                 120                 125

Ser Glu Gly Lys Pro Thr Glu Lys His Ile Gln Ile Arg Ser Thr Asn
        130                 135                 140
```

<210> SEQ ID NO 18
<211> LENGTH: 428
<212> TYPE: PRT
<213> ORGANISM: Mycobacterium tuberculosis

<400> SEQUENCE: 18

```
Met Ser Val Val Gly Thr Pro Lys Ser Ala Glu Gln Ile Gln Gln Glu
  1               5                  10                  15

Trp Asp Thr Asn Pro Arg Trp Lys Asp Val Thr Arg Thr Tyr Ser Ala
                 20                  25                  30

Glu Asp Val Val Ala Leu Gln Gly Ser Val Val Glu Glu His Thr Leu
             35                  40                  45

Ala Arg Arg Gly Ala Glu Val Leu Trp Glu Gln Leu His Asp Leu Glu
         50                  55                  60

Trp Val Asn Ala Leu Gly Ala Leu Thr Gly Asn Met Ala Val Gln Gln
 65                  70                  75                  80

Val Arg Ala Gly Leu Lys Ala Ile Tyr Leu Ser Gly Trp Gln Val Ala
                 85                  90                  95

Gly Asp Ala Asn Leu Ser Gly His Thr Tyr Pro Asp Gln Ser Leu Tyr
                100                 105                 110

Pro Ala Asn Ser Val Pro Gln Val Val Arg Arg Ile Asn Asn Ala Leu
            115                 120                 125

Gln Arg Ala Asp Gln Ile Ala Lys Ile Glu Gly Asp Thr Ser Val Glu
        130                 135                 140

Asn Trp Leu Ala Pro Ile Val Ala Asp Gly Glu Ala Gly Phe Gly Gly
145                 150                 155                 160

Ala Leu Asn Val Tyr Glu Leu Gln Lys Ala Leu Ile Ala Ala Gly Val
                165                 170                 175
```

Ala Gly Ser His Trp Glu Asp Gln Leu Ala Ser Glu Lys Lys Cys Gly
            180                 185                 190

His Leu Gly Gly Lys Val Leu Ile Pro Thr Gln His Ile Arg Thr
        195                 200                 205

Leu Thr Ser Ala Arg Leu Ala Ala Asp Val Ala Asp Val Pro Thr Val
    210                 215                 220

Val Ile Ala Arg Thr Asp Ala Glu Ala Ala Thr Leu Ile Thr Ser Asp
225                 230                 235                 240

Val Asp Glu Arg Asp Gln Pro Phe Ile Thr Gly Glu Arg Thr Arg Glu
                245                 250                 255

Gly Phe Tyr Arg Thr Lys Asn Gly Ile Glu Pro Cys Ile Ala Arg Ala
            260                 265                 270

Lys Ala Tyr Ala Pro Phe Ala Asp Leu Ile Trp Met Glu Thr Gly Thr
        275                 280                 285

Pro Asp Leu Glu Ala Ala Arg Gln Phe Ser Glu Ala Val Lys Ala Glu
    290                 295                 300

Tyr Pro Asp Gln Met Leu Ala Tyr Asn Cys Ser Pro Ser Phe Asn Trp
305                 310                 315                 320

Lys Lys His Leu Asp Asp Ala Thr Ile Ala Lys Phe Gln Lys Glu Leu
                325                 330                 335

Ala Ala Met Gly Phe Lys Phe Gln Phe Ile Thr Leu Ala Gly Phe His
            340                 345                 350

Ala Leu Asn Tyr Ser Met Phe Asp Leu Ala Tyr Gly Tyr Ala Gln Asn
        355                 360                 365

Gln Met Ser Ala Tyr Val Glu Leu Gln Glu Arg Glu Phe Ala Ala Glu
    370                 375                 380

Glu Arg Gly Tyr Thr Ala Thr Lys His Gln Arg Glu Val Gly Ala Gly
385                 390                 395                 400

Tyr Phe Asp Arg Ile Ala Thr Thr Val Asp Pro Asn Ser Ser Thr Thr
                405                 410                 415

Ala Leu Thr Gly Ser Thr Glu Glu Gly Gln Phe His
            420                 425

<210> SEQ ID NO 19
<211> LENGTH: 75
<212> TYPE: PRT
<213> ORGANISM: Mycobacterium tuberculosis

<400> SEQUENCE: 19

Val Ile Ala Gly Val Asp Gln Ala Leu Ala Ala Thr Gly Gln Ala Ser
1               5                   10                  15

Gln Arg Ala Ala Gly Ala Ser Gly Gly Val Thr Val Gly Val Gly Val
            20                  25                  30

Gly Thr Glu Gln Arg Asn Leu Ser Val Val Ala Pro Ser Gln Phe Thr
        35                  40                  45

Phe Ser Ser Arg Ser Pro Asp Phe Val Asp Glu Thr Ala Gly Gln Ser
    50                  55                  60

Trp Cys Ala Ile Leu Gly Leu Asn Gln Phe His
65                  70                  75

<210> SEQ ID NO 20
<211> LENGTH: 741
<212> TYPE: PRT
<213> ORGANISM: Mycobacterium tuberculosis

<400> SEQUENCE: 20

```
Met Thr Asp Arg Val Ser Val Gly Asn Leu Arg Ile Ala Arg Val Leu
1               5                   10                  15

Tyr Asp Phe Val Asn Asn Glu Ala Leu Pro Gly Thr Asp Ile Asp Pro
            20                  25                  30

Asp Ser Phe Trp Ala Gly Val Asp Lys Val Val Ala Asp Leu Thr Pro
        35                  40                  45

Gln Asn Gln Ala Leu Leu Asn Ala Arg Asp Glu Leu Gln Ala Gln Ile
    50                  55                  60

Asp Lys Trp His Arg Arg Val Ile Glu Pro Ile Asp Met Asp Ala
65                  70                  75                  80

Tyr Arg Gln Phe Leu Thr Glu Ile Gly Tyr Leu Leu Pro Glu Pro Asp
                85                  90                  95

Asp Phe Thr Ile Thr Thr Ser Gly Val Asp Ala Glu Ile Thr Thr Thr
            100                 105                 110

Ala Gly Pro Gln Leu Val Val Pro Val Leu Asn Ala Arg Phe Ala Leu
            115                 120                 125

Asn Ala Ala Asn Ala Arg Trp Gly Ser Leu Tyr Asp Ala Leu Tyr Gly
130                 135                 140

Thr Asp Val Ile Pro Glu Thr Asp Gly Ala Glu Lys Gly Pro Thr Tyr
145                 150                 155                 160

Asn Lys Val Arg Gly Asp Lys Val Ile Ala Tyr Ala Arg Lys Phe Leu
            165                 170                 175

Asp Asp Ser Val Pro Leu Ser Ser Gly Ser Phe Gly Asp Ala Thr Gly
                180                 185                 190

Phe Thr Val Gln Asp Gly Gln Leu Val Val Ala Leu Pro Asp Lys Ser
            195                 200                 205

Thr Gly Leu Ala Asn Pro Gly Gln Phe Ala Gly Tyr Thr Gly Ala Ala
    210                 215                 220

Glu Ser Pro Thr Ser Val Leu Leu Ile Asn His Gly Leu His Ile Glu
225                 230                 235                 240

Ile Leu Ile Asp Pro Glu Ser Gln Val Gly Thr Thr Arg Ala Gly
                245                 250                 255

Val Lys Asp Val Ile Leu Glu Ser Ala Ile Thr Thr Ile Met Asp Phe
            260                 265                 270

Glu Asp Ser Val Ala Ala Val Asp Ala Ala Asp Lys Val Leu Gly Tyr
    275                 280                 285

Arg Asn Trp Leu Gly Leu Asn Lys Gly Asp Leu Ala Ala Ala Val Asp
    290                 295                 300

Lys Asp Gly Thr Ala Phe Leu Arg Val Leu Asn Arg Asp Arg Asn Tyr
305                 310                 315                 320

Thr Ala Pro Gly Gly Gly Gln Phe Thr Leu Pro Gly Arg Ser Leu Met
                325                 330                 335

Phe Val Arg Asn Val Gly His Leu Met Thr Asn Asp Ala Ile Val Asp
            340                 345                 350

Thr Asp Gly Ser Glu Val Phe Glu Gly Ile Met Asp Ala Leu Phe Thr
            355                 360                 365

Gly Leu Ile Ala Ile His Gly Leu Lys Ala Ser Asp Val Asn Gly Pro
    370                 375                 380

Leu Ile Asn Ser Arg Thr Gly Ser Ile Tyr Ile Val Lys Pro Lys Met
385                 390                 395                 400

His Gly Pro Ala Glu Val Ala Phe Thr Cys Glu Leu Phe Ser Arg Val
                405                 410                 415

Glu Asp Val Leu Gly Leu Pro Gln Asn Thr Met Lys Ile Gly Ile Met
```

```
                420             425             430
Asp Glu Glu Arg Arg Thr Thr Val Asn Leu Lys Ala Cys Ile Lys Ala
            435             440             445

Ala Ala Asp Arg Val Val Phe Ile Asn Thr Gly Phe Leu Asp Arg Thr
            450             455             460

Gly Asp Glu Ile His Thr Ser Met Glu Ala Gly Pro Met Val Arg Lys
465             470             475             480

Gly Thr Met Lys Ser Gln Pro Trp Ile Leu Ala Tyr Glu Asp His Asn
            485             490             495

Val Asp Ala Gly Leu Ala Ala Gly Phe Ser Gly Arg Ala Gln Val Gly
            500             505             510

Lys Gly Met Trp Thr Met Thr Glu Leu Met Ala Asp Met Val Glu Thr
            515             520             525

Lys Ile Ala Gln Pro Arg Ala Gly Ala Ser Thr Ala Trp Val Pro Ser
            530             535             540

Pro Thr Ala Ala Thr Leu His Ala Leu His Tyr His Gln Val Asp Val
545             550             555             560

Ala Ala Val Gln Gln Gly Leu Ala Gly Lys Arg Arg Ala Thr Ile Glu
            565             570             575

Gln Leu Leu Thr Ile Pro Leu Ala Lys Glu Leu Ala Trp Ala Pro Asp
            580             585             590

Glu Ile Arg Glu Glu Val Asp Asn Asn Cys Gln Ser Ile Leu Gly Tyr
            595             600             605

Val Val Arg Trp Val Asp Gln Gly Val Gly Cys Ser Lys Val Pro Asp
            610             615             620

Ile His Asp Val Ala Leu Met Glu Asp Arg Ala Thr Leu Arg Ile Ser
625             630             635             640

Ser Gln Leu Leu Ala Asn Trp Leu Arg His Gly Val Ile Thr Ser Ala
            645             650             655

Asp Val Arg Ala Ser Leu Glu Arg Met Ala Pro Leu Val Asp Arg Gln
            660             665             670

Asn Ala Gly Asp Val Ala Tyr Arg Pro Met Ala Pro Asn Phe Asp Asp
            675             680             685

Ser Ile Ala Phe Leu Ala Ala Gln Glu Leu Ile Leu Ser Gly Ala Gln
            690             695             700

Gln Pro Asn Gly Tyr Thr Glu Pro Ile Leu His Arg Arg Arg Arg Glu
705             710             715             720

Phe Lys Ala Arg Ala Ala Glu Lys Pro Ala Pro Ser Asp Arg Ala Gly
            725             730             735

Asp Asp Ala Ala Arg
            740

<210> SEQ ID NO 21
<211> LENGTH: 943
<212> TYPE: PRT
<213> ORGANISM: Mycobacterium tuberculosis

<400> SEQUENCE: 21

Val Thr Ser Lys Ser Val Asn Ser Phe Gly Ala His Asp Thr Leu Lys
1               5               10              15

Val Gly Glu Lys Ser Tyr Gln Ile Tyr Arg Leu Asp Ala Val Pro Asn
            20              25              30

Thr Ala Lys Leu Pro Tyr Ser Leu Lys Val Leu Ala Glu Asn Leu Leu
            35              40              45
```

```
Arg Asn Glu Asp Gly Ser Asn Ile Thr Lys Asp His Ile Glu Ala Ile
 50                  55                  60

Ala Asn Trp Asp Pro Lys Ala Glu Pro Ser Ile Glu Ile Gln Tyr Thr
 65                  70                  75                  80

Pro Ala Arg Val Val Met Gln Asp Phe Thr Gly Val Pro Cys Ile Val
                 85                  90                  95

Asp Leu Ala Thr Met Arg Glu Ala Ile Ala Asp Leu Gly Gly Asn Pro
            100                 105                 110

Asp Lys Val Asn Pro Leu Ala Pro Ala Asp Leu Val Ile Asp His Ser
            115                 120                 125

Val Ile Ala Asp Leu Phe Gly Arg Ala Asp Ala Phe Glu Arg Asn Val
130                 135                 140

Glu Ile Glu Tyr Gln Arg Asn Gly Glu Arg Tyr Gln Phe Leu Arg Trp
145                 150                 155                 160

Gly Gln Gly Ala Phe Asp Asp Phe Lys Val Val Pro Pro Gly Thr Gly
                165                 170                 175

Ile Val His Gln Val Asn Ile Glu Tyr Leu Ala Ser Val Val Met Thr
            180                 185                 190

Arg Asp Gly Val Ala Tyr Pro Asp Thr Cys Val Gly Thr Asp Ser His
            195                 200                 205

Thr Thr Met Val Asn Gly Leu Gly Val Leu Gly Trp Gly Val Gly Gly
210                 215                 220

Ile Glu Ala Glu Ala Ala Met Leu Gly Gln Pro Val Ser Met Leu Ile
225                 230                 235                 240

Pro Arg Val Val Gly Phe Arg Leu Thr Gly Glu Ile Gln Pro Gly Val
                245                 250                 255

Thr Ala Thr Asp Val Val Leu Thr Val Thr Glu Met Leu Arg Gln His
            260                 265                 270

Gly Val Val Gly Lys Phe Val Glu Phe Tyr Gly Glu Gly Val Ala Glu
            275                 280                 285

Val Pro Leu Ala Asn Arg Ala Thr Leu Gly Asn Met Ser Pro Glu Phe
290                 295                 300

Gly Ser Thr Ala Ala Ile Phe Pro Ile Asp Glu Glu Thr Ile Lys Tyr
305                 310                 315                 320

Leu Arg Phe Thr Gly Arg Thr Pro Glu Gln Val Ala Leu Val Glu Ala
                325                 330                 335

Tyr Ala Lys Ala Gln Gly Met Trp His Asp Pro Lys His Glu Pro Glu
            340                 345                 350

Phe Ser Glu Tyr Leu Glu Leu Asn Leu Ser Asp Val Val Pro Ser Ile
            355                 360                 365

Ala Gly Pro Lys Arg Pro Gln Asp Arg Ile Ala Leu Ala Gln Ala Lys
370                 375                 380

Ser Thr Phe Arg Glu Gln Ile Tyr His Tyr Val Gly Asn Gly Ser Pro
385                 390                 395                 400

Asp Ser Pro His Asp Pro His Ser Lys Leu Asp Glu Val Val Glu Glu
                405                 410                 415

Thr Phe Pro Ala Ser Asp Pro Gly Gln Leu Thr Phe Ala Asn Asp Asp
            420                 425                 430

Val Ala Thr Asp Glu Thr Val His Ser Ala Ala His Ala Asp Gly
            435                 440                 445

Arg Val Ser Asn Pro Val Arg Val Lys Ser Asp Glu Leu Gly Glu Phe
450                 455                 460

Val Leu Asp His Gly Ala Val Val Ile Ala Ala Ile Thr Ser Cys Thr
```

-continued

```
            465                 470                 475                 480
        Asn Thr Ser Asn Pro Glu Val Met Leu Gly Ala Ala Leu Leu Ala Arg
                        485                 490                 495
        Asn Ala Val Glu Lys Gly Leu Thr Ser Lys Pro Trp Val Lys Thr Thr
                        500                 505                 510
        Ile Ala Pro Gly Ser Gln Val Asn Asp Tyr Tyr Asp Arg Ser Gly
                        515                 520                 525
        Leu Trp Pro Tyr Leu Glu Lys Leu Gly Phe Tyr Leu Val Gly Tyr Gly
                        530                 535                 540
        Cys Thr Thr Cys Ile Gly Asn Ser Gly Pro Leu Pro Glu Glu Ile Ser
        545                 550                 555                 560
        Lys Ala Val Asn Asp Asn Asp Leu Ser Val Thr Ala Val Leu Ser Gly
                        565                 570                 575
        Asn Arg Asn Phe Glu Gly Arg Ile Asn Pro Asp Val Lys Met Asn Tyr
                        580                 585                 590
        Leu Ala Ser Pro Pro Leu Val Ile Ala Tyr Ala Leu Ala Gly Thr Met
                        595                 600                 605
        Asp Phe Asp Phe Gln Thr Gln Pro Leu Gly Gln Asp Lys Asp Gly Lys
                        610                 615                 620
        Asn Val Phe Leu Arg Asp Ile Trp Pro Ser Gln Gln Asp Val Ser Asp
        625                 630                 635                 640
        Thr Ile Ala Ala Ala Ile Asn Gln Glu Met Phe Thr Arg Asn Tyr Ala
                        645                 650                 655
        Asp Val Phe Lys Gly Asp Asp Arg Trp Arg Asn Leu Pro Thr Pro Ser
                        660                 665                 670
        Gly Asn Thr Phe Glu Trp Asp Pro Asn Ser Thr Tyr Val Arg Lys Pro
                        675                 680                 685
        Pro Tyr Phe Glu Gly Met Thr Ala Lys Pro Glu Pro Val Gly Asn Ile
                        690                 695                 700
        Ser Gly Ala Arg Val Leu Ala Leu Leu Gly Asp Ser Val Thr Thr Asp
        705                 710                 715                 720
        His Ile Ser Pro Ala Gly Ala Ile Lys Pro Gly Thr Pro Ala Ala Arg
                        725                 730                 735
        Tyr Leu Asp Glu His Gly Val Asp Arg Lys Asp Tyr Asn Ser Phe Gly
                        740                 745                 750
        Ser Arg Arg Gly Asn His Glu Val Met Ile Arg Gly Thr Phe Ala Asn
                        755                 760                 765
        Ile Arg Leu Arg Asn Gln Leu Leu Asp Asp Val Ser Gly Gly Tyr Thr
                        770                 775                 780
        Arg Asp Phe Thr Gln Pro Gly Gly Pro Gln Ala Phe Ile Tyr Asp Ala
        785                 790                 795                 800
        Ala Gln Asn Tyr Ala Ala Gln His Ile Pro Leu Val Val Phe Gly Gly
                        805                 810                 815
        Lys Glu Tyr Gly Ser Gly Ser Ser Arg Asp Trp Ala Ala Lys Gly Thr
                        820                 825                 830
        Leu Leu Leu Gly Val Arg Ala Val Ile Ala Glu Ser Phe Glu Arg Ile
                        835                 840                 845
        His Arg Ser Asn Leu Ile Gly Met Gly Val Ile Pro Leu Gln Phe Pro
                        850                 855                 860
        Glu Gly Lys Ser Ala Ser Ser Leu Gly Leu Asp Gly Thr Glu Val Phe
        865                 870                 875                 880
        Asp Ile Thr Gly Ile Asp Val Leu Asn Asp Gly Lys Thr Pro Lys Thr
                        885                 890                 895
```

Val Cys Val Gln Ala Thr Lys Gly Asp Gly Ala Thr Ile Glu Phe Asp
                900                 905                 910

Ala Val Val Arg Ile Asp Thr Pro Gly Glu Ala Asp Tyr Tyr Arg Asn
            915                 920                 925

Gly Gly Ile Leu Gln Tyr Val Leu Arg Asn Ile Leu Lys Ser Gly
        930                 935                 940

<210> SEQ ID NO 22
<211> LENGTH: 95
<212> TYPE: PRT
<213> ORGANISM: Mycobacterium tuberculosis

<400> SEQUENCE: 22

Met Thr Glu Gln Gln Trp Asn Phe Ala Gly Ile Glu Ala Ala Ala Ser
 1               5                  10                  15

Ala Ile Gln Gly Asn Val Thr Ser Ile His Ser Leu Leu Asp Glu Gly
            20                  25                  30

Lys Gln Ser Leu Thr Lys Leu Ala Ala Ala Trp Gly Gly Ser Gly Ser
        35                  40                  45

Glu Ala Tyr Gln Gly Val Gln Gln Lys Trp Asp Ala Thr Ala Thr Glu
    50                  55                  60

Leu Asn Asn Ala Leu Gln Asn Leu Ala Arg Thr Ile Ser Glu Ala Gly
65                  70                  75                  80

Gln Ala Met Ala Ser Thr Glu Gly Asn Val Thr Gly Met Phe Ala
                85                  90                  95

<210> SEQ ID NO 23
<211> LENGTH: 714
<212> TYPE: DNA
<213> ORGANISM: Listeria monocytogenes

<400> SEQUENCE: 23
ttaatttaat tttccccaag tagcaggaca tgctaaataa aaccattcat ctaatttagg      60
ggcatatctt ttgagataat caagattttg tacataaaag catgaatttt tatacacgat     120
aactttctct tgctttaatt tggaaataat tctgctaaca gctgagctat gtgcgatgcc     180
acttgaatat cctaactcct gcattgttaa attatccagt gtaatcttga tgccatcagg     240
agtttcttta ccatacacat aggtcaggat taaaagttga ccgcaaatag agccaagctt     300
cccgttaatc gaaaaatcat taaatttagc tagactgtat gaaacttgtt tttgtagggt     360
ttggaaaaca tagaaaaagt gcgtaagatt tttgctcagt agttctttta gttcgtttat     420
tttgataacg tatgcggtag cctgctcgct aatgacttct aaattataat agccaaccga     480
tgtttctgta tcaataaagc cagacattat aacgaaagcc cctttgtagt attgtaaatt     540
catgatggtc ccgttctcgc taatactcgt gagctttgtg ataccatcat atagaaaaat     600
acaatattct tgtggatccc attggttaaa aataagttct tttttatgaa attgttttgg     660
ttttatcccg ttagtttcta aatattttt gaattcttct gcttgagcgt tcat            714

<210> SEQ ID NO 24
<211> LENGTH: 333
<212> TYPE: DNA
<213> ORGANISM: Mycobacterium tuberculosis

<400> SEQUENCE: 24
ttcgacaccc ggttgatgcg gctggaagac gagatgaaag aggggcgcta cgaggtacgc      60
gcggagcttc ccggggtcga ccccgacaag gacgtcgaca ttatggtccg cgatggtcag     120

```
ctgaccatca aggccgagcg caccgagcag aaggacttcg acggtcgctc ggaattcgcg      180
tacggttcct tcgttcgcac ggtgtcgctg ccggtaggtg ctgacgagga cgacattaag      240
gccacctacg acaagggcat tcttactgtg tcggtggcgg tttcggaagg gaagccaacc      300
gaaaagcaca ttcagatccg gtccaccaac tga                                  333

<210> SEQ ID NO 25
<211> LENGTH: 722
<212> TYPE: DNA
<213> ORGANISM: Mycobacterium tuberculosis

<400> SEQUENCE: 25
atgagtcttc gcctggtgtc cccgatcaag gcgtttgcgg acggcattgt ggccgttgct       60
atcgcggttg tcctgatgtt cggtctggcc aatacaccgc gagcggtggc agccgatgaa      120
cgtctgcagt tcaccgcaac cacgctcagc ggtgctccct tcgatggcgc aagcctgcaa      180
ggcaagccgg cggtgttgtg gttctggacg ccgtggtgcc cgttctgcaa cgcagaagcc      240
cccagcctca gccaggtagc ggccgctaat ccggcggtca ccttcgtcgg aatcgccacc      300
cgcgccgacg tcggggcgat gcagagcttt gtctcgaagt acaacctgaa tttcaccaac      360
ctcaatgacg ccgatggtgt gatctgggcc cgctacaacg tgccttggca accggcattt      420
gtgttctatc gcgcggacgg cacatcgacg ttcgtcaaca ccccaccgc ggccatgtct       480 caggacgagc tgtccggccg ggtggctgcg ctgacgtcct gacccggtga acgaggcgct      540
gatcggtttg gcgttcgccg ccgggttggt ggctgcgctg aacccatgcg ggtttgccat      600
gttgccggcc tacctgctgt tggtggtgta tgggcaggat tcggcgggcc ggacggggcc      660
gcttagcgca gtgggccgag cggcagccgc cacggtcggg atggcgctgg gcttcttgac      720
gg                                                                    722

<210> SEQ ID NO 26
<211> LENGTH: 480
<212> TYPE: DNA
<213> ORGANISM: Mycobacterium tuberculosis

<400> SEQUENCE: 26
atgaagctca ccacaatgat caagacggca gtagcggtcg tggccatggc ggccatcgcg       60
acctttgcgg caccggtcgc gttggctgcc tatcccatca ccggaaaact tggcagtgag      120
ctaacgatga ccgacaccgt tggccaagtc gtgctcggct ggaaggtcag tgatctcaaa      180
tccagcacgc cagtcatccc cggctatccg gtggccggcc aggtctggga ggccactgcc      240
acggtcaatg cgattcgcgg cagcgtcacg cccgcggtct cgcagttcaa tgcccgcacc      300
gccgacggca tcaactaccg ggtgctgtgg caagccgcgg gccccgacac cattagcgga      360
gccactatcc cccaaggcga acaatcgacc ggcaaaatct acttcgatgt caccggccca      420
tcgccaacca tcgtcgcgat gaacaacggc atggaggatc tgctgatttg ggagccgtag      480

<210> SEQ ID NO 27
<211> LENGTH: 624
<212> TYPE: DNA
<213> ORGANISM: Mycobacterium tuberculosis

<400> SEQUENCE: 27
gtggccgaat acaccttgcc agacctggac tgggactacg gagcactgga accgcacatc       60
tcgggtcaga tcaacgagct tcaccacagc aagcaccacg ccacctacgt aaagggcgcc      120
```

-continued aatgacgccg tcgccaaact cgaagaggcg cgcgccaagg aagatcactc agcgatcttg 180
ctgaacgaaa agaatctagc tttcaacctc gccggccacg tcaatcacac catctggtgg 240
aagaacctgt cgcctaacgg tggtgacaag cccaccggcg aactcgccgc agccatcgcc 300
gacgcgttcg gttcgttcga caagttccgt gcgcagttcc acgcggccgc taccaccgtg 360
caggggtcgg gctgggcggc actgggctgg gacacactcg gcaacaagct gctgatattc 420
caggtttacg accaccagac gaacttcccg ctaggcattg ttccgctgct gctgctcgac 480
atgtgggaac acgccttcta cctgcagtac aagaacgtca aagtcgactt tgccaaggcg 540
ttttggaacg tcgtgaactg ggccgatgtg cagtcacggt atgcggccgc gacctcgcag 600
accaaggggt tgatattcgg ctga 624

<210> SEQ ID NO 28
<211> LENGTH: 687
<212> TYPE: DNA
<213> ORGANISM: Mycobacterium tuberculosis

<400> SEQUENCE: 28
gtgcgcatca agatcttcat gctggtcacg gctgtcgttt tgctctgttg ttcgggtgtg 60
gccacggccg cgcccaagac ctactgcgag gagttgaaag gcaccgatac cggccaggcg 120
tgccagattc aaatgtccga cccggcctac aacatcaaca tcagcctgcc cagttactac 180
cccgaccaga agtcgctgga aaattacatc gcccagacgc gcgacaagtt cctcagcgcg 240
gccacatcgt ccactccacg cgaagccccc tacgaattga atatcacctc ggccacatac 300
cagtccgcga taccgccgcg tggtacgcag gccgtggtgc tcaaggtcta ccagaacgcc 360
ggcggcacgc acccaacgac cacgtacaag gccttcgatt gggaccaggc ctatcgcaag 420
ccaatcacct atgacacgct gtggcaggct gacaccgatc cgctgccagt cgtcttcccc 480
attgtgcaag gtgaactgag caagcagacc ggacaacagg tatcgatagc gccgaatgcc 540
ggcttggacc cggtgaatta tcagaacttc gcagtcacga acgacggggt gattttcttc 600
ttcaacccgg gggagttgct gcccgaagca gccggcccaa cccaggtatt ggtcccacgt 660
tccgcgatcg actcgatgct ggcctag 687

<210> SEQ ID NO 29
<211> LENGTH: 900
<212> TYPE: DNA
<213> ORGANISM: Mycobacterium tuberculosis

<400> SEQUENCE: 29
atgaagggtc ggtcggcgct gctgcgggcg ctctggattg ccgcactgtc attcgggttg 60
ggcggtgtcg cggtagccgc ggaacccacc gccaaggccg ccccatacga gaacctgatg 120
gtgccgtcgc cctcgatggg ccgggacatc ccggtggcct tcctagccgg tgggccgcac 180
gcggtgtatc tgctggacgc cttcaacgcc ggcccggatg tcagtaactg ggtcaccgcg 240
ggtaacgcga tgaacacgtt ggcgggcaag gggatttcgg tggtggcacc ggccggtggt 300
gcgtacagca tgtacaccaa ctgggagcag gatggcagca agcagtggga caccttcttg 360
tccgctgagc tgcccgactg gctggccgct aaccggggct tggcccccgg tggccatgcg 420
gccgttggcg ccgctcaggg cggttacggg gcgatggcgc tggcggcctt ccacccccgac 480 cgcttcggct tcgctggctc gatgtcgggc tttttgtacc cgtcgaacac caccaccaac 540
ggtgcgatcg cggcgggcat gcagcaattc ggcggtgtgg acaccaacgg aatgtgggga 600
gcaccacagc tgggtcggtg gaagtggcac gacccgtggg tgcatgccag cctgctggcg 660

```
caaaacaaca cccgggtgtg ggtgtggagc ccgaccaacc cgggagccag cgatcccgcc      720
gccatgatcg gccaagccgc cgaggcgatg ggtaacagcc gcatgttcta caaccagtat      780
cgcagcgtcg gcgggcacaa cggacacttc gacttcccag ccagcggtga caacggctgg      840
ggctcgtggg cgccccagct gggcgctatg tcgggcgata tcgtcggtgc gatccgctaa      900

<210> SEQ ID NO 30
<211> LENGTH: 978
<212> TYPE: DNA
<213> ORGANISM: Mycobacterium tuberculosis

<400> SEQUENCE: 30
atgacagacg tgagccgaaa gattcgagct tggggacgcc gattgatgat cggcacggca       60
gcggctgtag tccttccggg cctggtgggg cttgccggcg agcggcaac cgcgggcgcg      120 ttctcccggc cggggctgcc ggtcgagtac ctgcaggtgc cgtcgccgtc gatgggccgc      180
gacatcaagg ttcagttcca gagcggtggg aacaactcac ctgcggttta tctgctcgac      240
ggcctgcgcg cccaagacga ctacaacggc tgggatatca acaccccggc gttcgagtgg      300
tactaccagt cgggactgtc gatagtcatg ccggtcggcg ggcagtccag cttctacagc      360
gactggtaca gcccggcctg cggtaaggct ggctgccaga cttacaagtg ggaaaccttc      420
ctgaccagcg agctgccgca atggttgtcc gccaacaggg ccgtgaagcc caccggcagc      480
gctgcaatcg gcttgtcgat ggccggctcg tcggcaatga tcttggccgc ctaccacccc      540
cagcagttca tctacgccgg ctcgctgtcg gccctgctgg acccctctca ggggatgggg      600
cctagcctga tcggcctcgc gatgggtgac gccggcggtt acaaggccgc agacatgtgg      660
ggtccctcga gtgaccccgg catgggagcg aacgacccta cgcagcagat ccccaagctg      720
gtcgcaaaca acacccggct atgggtttat tgcgggaacg gcaccccgaa cgagttgggc      780
ggtgccaaca tacccgccga gttcttggag aacttcgttc gtagcagcaa cctgaagttc      840
caggatgcgt acaacgccgc gggcgggcac aacgccgtgt tcaacttccc gcccaacggc      900
acgcacagct gggagtactg gggcgctcag ctcaacgcca tgaagggtga cctgcagagt      960
tcgttaggcg ccggctga                                                   978

<210> SEQ ID NO 31
<211> LENGTH: 1017
<212> TYPE: DNA
<213> ORGANISM: Mycobacterium tuberculosis

<400> SEQUENCE: 31
atgcagcttg ttgacagggt tcgtggcgcc gtcacgggta tgtcgcgtcg actcgtggtc       60
ggggccgtcg gcgcggccct agtgtcgggt ctggtcggcg ccgtcggtgg cacggcgacc      120 gcggggggcat tttcccggcc gggcttgccg gtggagtacc tgcaggtgcc gtcgccgtcg      180
atgggccgtg acatcaaggt ccaattccaa agtggtggtg ccaactcgcc cgccctgtac      240
ctgctcgacg gcctgcgcgc gcaggacgac ttcagcggct gggacatcaa caccccggcg      300
ttcgagtggt acgaccagtc gggcctgtcg gtggtcatgc cggtgggtgg ccagtcaagc      360
ttctactccg actggtacca gcccgcctgc ggcaaggccg gttgccagac ttacaagtgg      420
gagaccttcc tgaccagcga gctgccgggg tggctgcagg ccaacaggca cgtcaagccc      480
accggaagcg ccgtcgtcgg tctttcgatg gctgcttctt cggcgctgac gctggcgatc      540
tatcaccccc agcagttcgt ctacgcggga gcgatgtcgg gcctgttgga ccccctcccag      600
```

```
gcgatgggtc ccaccctgat cggcctggcg atgggtgacg ctggcggcta caaggcctcc      660
gacatgtggg gcccgaagga ggacccggcg tggcagcgca acgacccgct gttgaacgtc      720
gggaagctga tcgccaacaa caccgcgtc tgggtgtact gcggcaacgg caagccgtcg       780
gatctgggtg caacaacct gccggccaag ttcctcgagg gcttcgtgcg gaccagcaac       840
atcaagttcc aagacgccta caacgccggt ggcggccaca acggcgtgtt cgacttcccg      900
gacagcggta cgcacagctg ggagtactgg ggcgcgcagc tcaacgctat gaagcccgac      960
ctgcaacggg cactgggtgc cacgcccaac accgggcccg cgcccaggg cgcctag          1017
```

<210> SEQ ID NO 32
<211> LENGTH: 738
<212> TYPE: DNA
<213> ORGANISM: Mycobacterium tuberculosis

<400> SEQUENCE: 32

```
atggccaagt tggcccgagt agtgggccta gtacaggaag agcaacctag cgacatgacg       60
aatcacccac ggtattcgcc accgccgcag cagccgggaa ccccaggtta tgctcagggg      120
cagcagcaaa cgtacagcca gcagttcgac tggcgttacc caccgtcccc gccccgcag      180 ccaacccagt accgtcaacc ctacgaggcg ttgggtggta cccggccggg tctgataccct    240 ggcgtgattc cgaccatgac gccccctcct gggatggttc gccaacgccc tcgtgcaggc      300
atgttggcca tcggcgcgt gacgatagcg gtggtgtccg ccggcatcgg cggcgcggcc      360
gcatccctgg tcgggttcaa ccgggcaccc gccggcccca gcggcggccc agtggctgcc      420
agcgcggcgc caagcatccc gcagcaaac atgccgccgg ggtcggtcga acaggtggcg      480
gccaaggtgg tgcccagtgt cgtcatgttg gaaaccgatc tgggccgcca gtcggaggag      540
ggctccggca tcattctgtc tgccgagggg ctgatcttga ccaacaacca cgtgatcgcg      600
gcggccgcca agcctcccct gggcagtccg ccgccgaaaa cgacggtaac cttctctgac      660
gggcggaccg caccttcac ggtggtgggg gctgaccca ccagtgatat cgccgtcgtc        720
cgtgttcagg gcgtctcc                                                    738
```

<210> SEQ ID NO 33
<211> LENGTH: 978
<212> TYPE: DNA
<213> ORGANISM: Mycobacterium tuberculosis

<400> SEQUENCE: 33

```
atgcatcagg tggaccccaa cttgacacgt cgcaagggac gattggcggc actggctatc       60
gcggcgatgg ccagcgccag cctggtgacc gttgcggtgc ccgcgaccgc caacgccgat      120
ccggagccag cgccccggt acccacaacg gccgcctcgc cgccgtcgac cgctgcagcg       180
ccacccgcac cggcgacacc tgttgccccc ccaccaccgg ccgccgccaa cacgccgaat      240
gcccagccgg gcgatcccaa cgcagcacct ccgccggccg acccgaacgc accgccgcca      300
cctgtcattg ccccaaacgc acccccaacct gtccggatcg acaacccggt tggaggattc     360
agcttcgcgc tgcctgctgg ctgggtggag tctgacgccg cccacttcga ctacggttca     420
gcactcctca gcaaaaccac cggggacccg ccatttcccg gacagccgcc gccggtggcc      480
aatgacaccc gtatcgtgct cggccggcta gaccaaaagc tttacgccag cgccgaagcc      540
accgactcca aggccgcggc ccggttgggc tcggacatgg gtgagttcta tatgccctac      600
ccgggcaccc ggatcaacca ggaaaccgtc tcgctcgacg ccaacggggt gtctggaagc      660
gcgtcgtatt acgaagtcaa gttcagcgat ccgagtaagc cgaacggcca gatctggacg      720
```

-continued

```
ggcgtaatcg gctcgcccgc ggcgaacgca ccggacgccg ggccccctca gcgctggttt    780
gtggtatggc tcgggaccgc caacaacccg gtggacaagg gcgcggccaa ggcgctggcc    840
gaatcgatcc ggcctttggt cgccccgccg ccggcgccgg caccggctcc tgcagagccc    900
gctccggcgc cggcgccggc cggggaagtc gctcctaccc cgacgacacc gacaccgcag    960
cggaccttac cggcctga                                                  978
```

<210> SEQ ID NO 34
<211> LENGTH: 1437
<212> TYPE: DNA
<213> ORGANISM: Mycobacterium tuberculosis

<400> SEQUENCE: 34

```
gtgacggaaa agacgcccga cgacgtcttc aaacttgcca aggacgagaa ggtcgaatat     60
gtcgacgtcc ggttctgtga cctgcctggc atcatgcagc acttcacgat tccggcttcg    120
gcctttgaca agagcgtgtt tgacgacggc ttggcctttg acggctcgtc gattcgcggg    180
ttccagtcga tccacgaatc cgacatgttg cttcttcccg atcccgagac ggcgcgcatc    240
gacccgttcc gcgcggccaa gacgctgaat atcaacttct ttgtgcacga cccgttcacc    300
ctggagccgt actcccgcga cccgcgcaac atcgcccgca aggccgagaa ctacctgatc    360
agcactggca tcgccgacac cgcatacttc ggcgccgagg ccgagttcta cattttcgat    420
tcggtgagct tcgactcgcg cgccaacggc tccttctacg aggtggacgc catctcgggg    480
tggtggaaca ccggcgcggc gaccgaggcc gacggcagtc ccaaccgggg ctacaaggtc    540
cgccacaagg gcgggtattt cccagtggcc cccaacgacc aatacgtcga cctgcgcgac    600
aagatgctga ccaacctgat caactccggc ttcatcctgg agaagggcca ccacgaggtg    660
ggcagcggcg gacaggccga gatcaactac cagttcaatt cgctgctgca cgccgccgac    720
gacatgcagt tgtacaagta catcatcaag aacaccgcct ggcagaacgg caaaacggtc    780
acgttcatgc ccaagccgct gttcggcgac aacgggtccg gcatgcactg tcatcagtcg    840
ctgtggaagg acggggcccc gctgatgtac gacgagacgg gttatgccgg tctgtcggac    900
acggcccgtc attacatcgg cggcctgtta caccacgcgc cgtcgctgct ggccttcacc    960
aacccgacgg tgaactccta caagcggctg gttcccggtt acgaggcccc gatcaacctg   1020
gtctatagcc agcgcaaccg gtcggcatgc gtgcgcatcc cgatcaccgg cagcaacccg   1080
aaggccaagc ggctggagtt ccgaagcccc gactcgtcgg gcaacccgta tctggcgttc   1140
tcggccatgc tgatggcagg cctggacggt atcaagaaca agatcgagcc gcaggcgccc   1200
gtcgacaagg atctctacga gctgccgccg gaagaggccg cgagtatccc gcagactccg   1260
acccagctgt cagatgtgat cgaccgtctc gaggccgacc acgaatacct caccgaagga   1320
ggggtgttca caaacgacct gatcgagacg tggatcagtt tcaagcgcga aaacgagatc   1380
gagccggtca acatccggcc gcatccctac gaattcgcgc tgtactacga cgtttaa      1437
```

<210> SEQ ID NO 35
<211> LENGTH: 1878
<212> TYPE: DNA
<213> ORGANISM: Mycobacterium tuberculosis

<400> SEQUENCE: 35

```
atggctcgtg cggtcgggat cgacctcggg accaccaact ccgtcgtctc ggttctggaa     60
ggtggcgacc cggtcgtcgt cgccaactcc gagggctcca ggaccacccc gtcaattgtc    120
```

| | |
|---|---|
| gcgttcgccc gcaacggtga ggtgctggtc ggccagcccg ccaagaacca ggcagtgacc | 180 |
| aacgtcgatc gcaccgtgcg ctcggtcaag cgacacatgg gcagcgactg gtccatagag | 240 |
| attgacggca agaaatacac cgcgccggag atcagcgccc gcattctgat gaagctgaag | 300 |
| cgcgacgccg aggcctacct cggtgaggac attaccgacg cggttatcac gacgcccgcc | 360 |
| tacttcaatg acgcccagcg tcaggccacc aaggacgccg gccagatcgc cggcctcaac | 420 |
| gtgctgcgga tcgtcaacga gccgaccgcg gccgcgctgg cctacggcct cgacaagggc | 480 |
| gagaaggagc agcgaatcct ggtcttcgac ttgggtggtg gcactttcga cgtttccctg | 540 |
| ctggagatcg gcgagggtgt ggttgaggtc cgtgccactt cgggtgacaa ccacctcggc | 600 |
| ggcgacgact gggaccagcg ggtcgtcgat tggctggtgg acaagttcaa gggcaccagc | 660 |
| ggcatcgatc tgaccaagga caagatggcg atgcagcggc tgcggaagc cgccgagaag | 720 |
| gcaaagatcg agctgagttc gagtcagtcc acctcgatca acctgcccta catcaccgtc | 780 |
| gacgccgaca gaacccgtt gttcttagac gagcagctga cccgcgcgga gttccaacgg | 840 |
| atcactcagg acctgctgga ccgcactcgc aagccgttcc agtcggtgat cgctgacacc | 900 |
| ggcatttcgg tgtcggagat cgatcacgtt gtgctcgtgg gtggttcgac ccggatgccc | 960 |
| gcggtgaccg atctggtcaa ggaactcacc ggcggcaagg aacccaacaa gggcgtcaac | 1020 |
| cccgatgagg ttgtcgcggt gggagccgct ctgcaggccg gcgtcctcaa gggcgaggtg | 1080 |
| aaagacgttc tgctgcttga tgttacccg ctgagcctgg gtatcgagac caagggcggg | 1140 |
| gtgatgacca ggctcatcga gcgcaacacc acgatcccca ccaagcggtc ggagactttc | 1200 |
| accaccgccg acgacaacca accgtcggtg cagatccagg tctatcaggg ggagcgtgag | 1260 |
| atcgccgcgc acaacaagtt gctcgggtcc ttcgagctga ccggcatccc gccggcgccg | 1320 |
| cgggggattc cgcagatcga ggtcactttc gacatcgacg ccaacggcat tgtgcacgtc | 1380 |
| accgccaagg acaagggcac cggcaaggag aacacgatcc gaatccagga aggctcgggc | 1440 |
| ctgtccaagg aagacattga ccgcatgatc aaggacgccg aagcgcacgc cgaggaggat | 1500 |
| cgcaagcgtc gcgaggaggc cgatgttcgt aatcaagccg agacattggt ctaccagacg | 1560 |
| gagaagttcg tcaaagaaca gcgtgaggcc gaggtggtt cgaaggtacc tgaagacacg | 1620 |
| ctgaacaagg ttgatgccgc ggtggcggaa gcgaaggcgg cacttggcgg atcggatatt | 1680 |
| tcggccatca gtcggcgat ggagaagctg ggccaggagt cgcaggctct ggggcaagcg | 1740 |
| atctacgaag cagctcaggc tgcgtcacag gccactggcg ctgcccaccc cggcggcgag | 1800 |
| ccgggcggtg cccaccccgg ctcggctgat gacgttgtgg acgcggaggt ggtcgacgac | 1860 |
| ggccgggagg ccaagtga | 1878 |

<210> SEQ ID NO 36
<211> LENGTH: 291
<212> TYPE: DNA
<213> ORGANISM: Mycobacterium tuberculosis

<400> SEQUENCE: 36

| | |
|---|---|
| atgtcgcaaa tcatgtacaa ctaccccgcg atgttgggtc acgccgggga tatggccgga | 60 |
| tatgccggca cgctgcagag cttgggtgcc gagatcgccg tggagcaggc cgcgttgcag | 120 |
| agtgcgtggc agggcgatac cgggatcacg tatcaggcgt ggcaggcaca gtggaaccag | 180 |
| gccatggaag atttggtgcg ggcctatcat gcgatgtcca gcacccatga agccaacacc | 240 |
| atggcgatga tgcccgcga cacggccgaa gccgccaaat ggggcggcta g | 291 |

<210> SEQ ID NO 37
<211> LENGTH: 435
<212> TYPE: DNA
<213> ORGANISM: Mycobacterium tuberculosis

<400> SEQUENCE: 37

| | | | | | |
|---|---|---|---|---|---|
| atggccacca | cccttcccgt | tcagcgccac | ccgcggtccc | tcttcccga | gttttctgag | 60 |
| ctgttcgcgg | ccttcccgtc | attcgccgga | ctccggccca | ccttcgacac | ccggttgatg | 120 |
| cggctggaag | acgagatgaa | agaggggcgc | tacgaggtac | gcgcggagct | tcccggggtc | 180 |
| gaccccgaca | aggacgtcga | cattatggtc | cgcgatggtc | agctgaccat | caaggccgag | 240 |
| cgcaccgagc | agaaggactt | cgacggtcgc | tcggaattcg | cgtacggttc | cttcgttcgc | 300 |
| acggtgtcgc | tgccggtagg | tgctgacgag | gacgacatta | aggccaccta | cgacaagggc | 360 |
| attcttactg | tgtcggtggc | ggtttcggaa | gggaagccaa | ccgaaaagca | cattcagatc | 420 |
| cggtccacca | actga | | | | | 435 |

<210> SEQ ID NO 38
<211> LENGTH: 1287
<212> TYPE: DNA
<213> ORGANISM: Mycobacterium tuberculosis

<400> SEQUENCE: 38

| | | | | | |
|---|---|---|---|---|---|
| atgtctgtcg | tcggcacccc | gaagagcgcg | gagcagatcc | agcaggaatg | ggacacgaac | 60 |
| ccgcgctgga | aggacgtcac | ccgcacctac | tccgccgagg | acgtcgtcgc | cctccagggc | 120 |
| agcgtggtcg | aggagcacac | gctggcccgc | gcggtgcgg | aggtgctgtg | ggagcagctg | 180 |
| cacgacctcg | agtgggtcaa | cgcgctgggc | gcgctgaccg | gcaacatggc | cgtccagcag | 240 |
| gtgcgcgccg | gcctgaaggc | catctacctg | tcgggctggc | aggtcgccgg | cgatgccaac | 300 |
| ctgtccgggc | acacctaccc | cgaccagagc | ctgtatcccg | ccaactcggt | gccgcaggtg | 360 |
| gtccgccgga | tcaacaacgc | actgcagcgc | gccgaccaga | tcgccaagat | cgagggcgat | 420 |
| acttcggtgg | agaactggct | ggcgccgatt | gtcgccgacg | gcgaggccgg | ctttggcggc | 480 |
| gcgctcaacg | tctacgagct | gcagaaagcc | ctgatcgccg | cgggcgttgc | gggttcgcac | 540 |
| tgggaggacc | agttggcctc | tgagaagaag | tgcgccacc | tgggcggcaa | ggtgttgatc | 600 |
| ccgacccagc | agcacatccg | cactttgacg | tctgctcggc | tcgcggccga | tgtggctgat | 660 |
| gttcccacgg | tggtgatcgc | ccgtaccgac | gccgaggcgg | ccacgctgat | cacctccgac | 720 |
| gtcgacgagc | gcgaccagcc | gttcatcacc | ggcgagcgca | cccgggaagg | cttctaccgc | 780 |
| accaagaacg | gcatcgagcc | ttgcatcgct | cgggcgaagg | cctacgcccc | gttcgccgac | 840 |
| ttgatctgga | tggagaccgg | taccccggac | ctcgaggccg | cccggcagtt | ctccgaggcg | 900 |
| gtcaaggcg | agtacccgga | ccagatgctg | gcctacaact | gctcgccatc | gttcaactgg | 960 |
| aaaaagcacc | tcgacgacgc | caccatcgcc | aagttccaga | aggagctggc | agccatgggc | 1020 |
| ttcaagttcc | agttcatcac | gctggccggc | ttccatgcgc | tgaactactc | gatgttcgat | 1080 |
| ctggcctacg | gctacgccca | gaaccagatg | agcgcgtatg | tcgaactgca | ggaacgcgag | 1140 |
| ttcgccgccg | aagaacgggg | ctacaccgcg | accaagcacc | agcgcgaggt | cggcgccggc | 1200 |
| tacttcgacc | ggattgccac | caccgtggac | ccgaattcgt | cgaccaccgc | gttgaccggt | 1260 |
| tccaccgaag | agggccagtt | ccactag | | | | 1287 |

<210> SEQ ID NO 39
<211> LENGTH: 228
<212> TYPE: DNA

<213> ORGANISM: Mycobacterium tuberculosis

<400> SEQUENCE: 39
gtgatagcgg gcgtcgacca ggcgcttgca gcaacaggcc aggctagcca gcgggcggca 60
ggcgcatctg gtggggtcac cgtcggtgtc ggcgtgggca cggaacagag gaacctttcg 120
gtggttgcac cgagtcagtt cacatttagt tcacgcagcc cagattttgt ggatgaaacc 180
gcaggtcaat cgtggtgcgc gatactggga ttgaaccagt ttcactag 228

<210> SEQ ID NO 40
<211> LENGTH: 2226
<212> TYPE: DNA
<213> ORGANISM: Mycobacterium tuberculosis

<400> SEQUENCE: 40
atgacagatc gcgtgtcggt gggcaacttg cgcatcgctc gggtgctcta cgacttcgtg 60
aacaatgaag ccctgcctgg caccgatatc gacccggaca gcttctgggc gggcgtcgac 120
aaggtcgtcg ccgacctgac ccgcagaac caagctctgt tgaacgcccg cgacgagctg 180
caggcgcaga tcgacaagtg gcaccggcgt cgggtgatcg agcccatcga catggatgcc 240
taccgccagt tcctcaccga gatcggctac ctgcttcccg aacctgatga cttcaccatc 300
accacgtccg gtgtcgacgc tgagatcacc acgaccgccg gcccccagct ggtggtgccg 360
gtgctcaacg cgcggtttgc tctgaacgcg gccaacgctc gctggggctc cctctacgac 420
gccttgtatg gcaccgatgt catccccgag accgacggcg ccgaaaaagg ccccacgtac 480
aacaaggttc gtggcgacaa ggtgatcgcg tatgcccgca agttcctcga cgacagtgtt 540
ccgctgtcgt cgggttcctt tggcgacgcc accggtttca cagtgcagga tggccagctc 600
gtggttgcct tgccggataa gtccaccggc ctggccaacc ccggccagtt cgccggctac 660
accggcgcag ccgagtcgcc gacatcggtg ctgctaatca atcacggttt gcacatcgag 720
atcctgatcg atccggagtc gcaggtcggc accaccgacc gggccggcgt caaggacgtg 780
atcctggaat ccgcgatcac cacgatcatg gacttcgagg actcggtggc cgccgtggac 840
gccgccgaca aggtgctggg ttatcggaac tggctcggcc tgaacaaggg cgacctggca 900
gcagcggtag acaaggacgg caccgctttc ctgcgggtgc tcaataggga ccggaactac 960
accgcacccg gcggtggcca gttcacgctg cctggacgca gcctcatgtt cgtccgcaac 1020
gtcggtcact tgatgacgaa tgacgccatc gtcgacactg acggcagcga ggtgttcgaa 1080
ggcatcatgg atgccctatt caccggcctg atcgccatcc acgggctaaa ggccagcgac 1140
gtcaacgggc cgctgatcaa cagccgcacc ggctccatct acatcgtcaa gccgaagatg 1200
cacggtccgg ccgaggtggc gtttacctgc gaactgttca gccgggttga agatgtgctg 1260
gggttgccgc aaaacaccat gaagatcggc atcatggacg aggaacgccg gaccacggtc 1320
aacctcaagg cgtgcatcaa agctgccgcg gaccgcgtgg tgttcatcaa caccgggttc 1380
ctggaccgca ccggcgatga aatccacacc tcgatggagg ccggcccgat ggtgcgcaag 1440
ggcaccatga agagccagcc gtggatcttg gcctacgagg accacaacgt cgatgccggc 1500
ctggccgccg ggttcagcgg ccgagcccag gtcggcaagg gcatgtggac aatgaccgag 1560
ctgatggccg acatggtcga gacaaaaatc gcccagccgc gcgccggggc cagcaccgcc 1620
tgggttccct ctcccactgc ggccaccctg catgcgctgc actaccacca ggtcgacgtc 1680
gccgcggtgc aacaaggact ggcggggaag cgtcgcgcca ccatcgaaca attgctgacc 1740
attccgctgg ccaaggaatt ggcctgggct cccgacgaga tccgcgaaga ggtcgacaac 1800

```
aactgtcaat ccatcctcgg ctacgtggtt cgctgggttg atcaaggtgt cggctgctcg    1860
aaggtgcccg acatccacga cgtcgcgctc atggaggacc gggccacgct gcgaatctcc    1920
agccaattgt tggccaactg gctgcgccac ggtgtgatca ccagcgcgga tgtgcgggcc    1980
agcttggagc ggatggcgcc gttggtcgat cgacaaaacg cgggcgacgt ggcataccga    2040
ccgatggcac ccaacttcga cgacagtatc gccttcctgg ccgcgcagga gctgatcttg    2100
tccggggccc agcagcccaa cggctacacc gagccgatcc tgcaccgacg tcgtcgggag    2160
tttaaggccc gggccgctga aagccggccc ccatcggaca gggccggtga cgatgcggcc    2220
cgctag                                                               2226
```

<210> SEQ ID NO 41
<211> LENGTH: 2832
<212> TYPE: DNA
<213> ORGANISM: Mycobacterium tuberculosis

<400> SEQUENCE: 41

```
gtgactagca aatctgtgaa ctcattcgga gcccacgaca ccctgaaggt cggcgaaaag      60
agttaccaga tctatcgtct cgacgccgtc cccaataccg cgaaactccc ctacagcctc    120
aaagtgctcg ccgagaacct gttgcgcaac gaggacggca gcaacatcac caaggaccac    180
atcgaggcca tcgccaactg ggaccctaag gccgagccca gcatcgagat ccagtacacg    240
cccgcccggg tggtgatgca ggacttcacc ggcgtaccgt gcatcgtcga cttggccacc    300
atgcgcgagg cgatcgccga tctgggcggc aaccccgaca aggtcaaccc gctggcgccc    360
gcagacttgg tgatcgacca ctcggtgatc gccgatttgt tcggccgcgc cgacgcattc    420
gagcgcaacg tcgaaatcga ataccagcgc aacggtgagc gttaccaatt cctgcgctgg    480
ggccaaggcg ctttcgacga cttcaaagtg gtgccgccgg caccggcat cgtgcaccag    540 gtcaatatcg agtacctggc cagcgtggtg atgactcgcg acggagtggc ctaccccgac    600
acctgcgtgg gcaccgactc acacaccacc atggtcaacg gcctgggtgt gctcgggtgg    660
ggtgtcggcg gcatcgaggc ggaggccgcg atgctgggtc agccggtatc gatgctgatc    720
ccgcgggtcg tgggtttcag gttgaccggc gagatccagc cggagtcac cgccaccgac    780 gtggtgttga ccgtcaccga gatgctgcgc cagcacggcg tcgtcggcaa attcgtcgag    840
ttctacggcg agggcgtggc cgaggtgccg ctggccaacc cgccaccct gggcaacatg    900 agtcccgaat cggttccac cgcagcgatt ttcccgatcg acgaagaaac catcaagtat    960
ctgcggttta ccggtcgcac gccggagcag gtcgcactgg tcgaggccta cgccaaggcg    1020
cagggcatgt ggcacgatcc caagcacgag ccggagttct cggaatacct cgaactcaac    1080
ctatccgacg tggtgccgtc gatcgccgga ccaaagcgtc cacaggaccg aatcgcgttg    1140
gcgcaagcca aatcaacatt ccgcgagcag atttaccact atgtcggcaa tggttccccg    1200 gattccccc acgacccgca ctcgaagctg acgaggtag tcgaggagac attcccggcc    1260
agcgacccgg ggcagctgac gttcgccaac gacgacgtcg ccactgacga aaccgtgcac    1320
tcggctgccg cgcatgccga tggcggggtg agcaacccag tgcgggtgaa gtcggacgaa    1380
ctcggcgaat tcgtgctcga ccacggcgcg gtggtgattg ccgcgatcac gtcctgcacc    1440
aacacctcca accccgaagt aatgctgggc gcggcgctgc tggcccgcaa cgccgtcgaa    1500
aagggactga cctcgaagcc gtgggtgaag accacgattg ccccgggctc gcaagtggtc    1560
aacgactact acgacagatc cggcctgtgg ccgtatctgg agaagctcgg cttctatctg    1620
```

```
gtcggctacg gctgcaccac ctgcatcggc aactccgggc cgctgcccga ggaaatctca   1680
aaagcggtta acgacaacga cctttcggtg accgcggtac tgtccggcaa ccggaacttc   1740
gagggccgta tcaacccaga cgtgaagatg aactacctgg catcgccgcc gctggtcatc   1800
gcctacgcgc tggccgggac catggacttc gacttccaaa cccagccgct cggtcaagac   1860
aaagacggta agaacgtttt tctccgcgat atctggccat cgcagcagga tgtctccgac   1920
accatcgccg cggcgatcaa ccaggagatg ttcacccgca actacgccga cgtgttcaag   1980
ggcgacgacc gctggcgcaa cctgccaacc ccgagcggca cacctttga gtgggacccg     2040 aattcgacct acgtgcgcaa gccgccgtat ttcgagggga tgacagccaa acccgaaccg   2100
gtcggcaaca tcagcggtgc ccgggtgctg gcgctgctcg gtgattcggt gaccaccgac   2160
cacatctccc ccgccggcgc catcaagccc ggaactcccg cggcgcgcta cctcgacgaa   2220
cacggtgtcg accgcaagga ctacaactcc ttcggttctc gccgcggcaa ccacgaggtg   2280
atgattcgtg gcaccttcgc caacatccgg ctgcgtaacc aactgctaga cgacgtgtcc   2340
ggcggttata cccgcgactt cacccagccg ggcggtccgc aggcgttcat ctacgacgcc   2400
gcgcagaact atgcggcgca acacattccg ctggttgtgt tcggcggcaa agagtacggg   2460
tcgggttcgt cacgggactg ggcggccaaa ggcacattgc tactgggcgt gcgggcggtg   2520
atcgccgagt cattcgagcg gatccaccgg tccaacctga tcggcatggg cgtgatcccg   2580
ctgcagttcc ccgaaggaaa gtcagcgtcg tcgtttggga ctcgacggtac cgaggtcttc   2640 gacatcaccg gtatcgacgt gcttaacgac ggcaagacac ccaagacggt gtgcgtccag   2700
gccaccaagg gcgacggcgc cacgatcgag ttcgacgccg tggtgcgcat cgacacccccc   2760 ggtgaggcgg actactaccg caacggcggc atcctgcagt acgtgctgcg caacatactg   2820
aagtcaggct ga                                                         2832

<210> SEQ ID NO 42
<211> LENGTH: 288
<212> TYPE: DNA
<213> ORGANISM: Mycobacterium tuberculosis

<400> SEQUENCE: 42
atgacagagc agcagtggaa tttcgcgggt atcgaggccg cggcaagcgc aatccaggga     60
aatgtcacgt ccattcattc cctccttgac gaggggaagc agtccctgac caagctcgca    120
gcggcctggg gcggtagcgg ttcggaggcg taccagggtg tccagcaaaa atgggacgcc    180
acggctaccg agctgaacaa cgcgctgcag aacctggcgc ggacgatcag cgaagccggt    240
caggcaatgg cttcgaccga aggcaacgtc actgggatgt tcgcatag                 288

<210> SEQ ID NO 43
<211> LENGTH: 1920
<212> TYPE: DNA
<213> ORGANISM: Listeria monocytogenes

<400> SEQUENCE: 43
gtgggattaa acagatttat gcgtgcgatg atggtggttt tcattactgc caattgcatt     60
acgattaacc ccgacataat atttgcagcg acagatagcg aagattctag tctaaacaca    120
gatgaatggg aagaagaaaa aacagaagag caaccaagcg aggtaaatac gggaccaaga    180
tacgaaactg cacgtgaagt aagttcacgt gatattaaag aactagaaaa atcgaataaa    240
gtgagaaata cgaacaaagc agacctaata gcatgttga agaaaaagc agaaaaaggt    300 ccaaatatca ataataacaa cagtgaacaa actgagaatg cggctataaa tgaagaggct    360
```

```
tcaggagccg accgaccagc tatacaagtg gagcgtcgtc atccaggatt gccatcggat      420
agcgcagcgg aaattaaaaa aagaaggaaa gccatagcat catcggatag tgagcttgaa      480
agccttactt atccggataa accaacaaaa gtaaataaga aaaagtggc gaaagagtca       540 gttgcggatg cttctgaaag tgacttagat tctagcatgc agtcagcaga tgagtcttca      600
ccacaacctt taaaagcaaa ccaacaacca ttttccccta aagtatttaa aaaaataaaa      660
gatgcgggga aatgggtacg tgataaaatc gacgaaaatc ctgaagtaaa gaaagcgatt      720
gttgataaaa gtgcagggtt aattgaccaa ttattaacca aaaagaaaag tgaagaggta      780
aatgcttcgg acttcccgcc accacctacg gatgaagagt taagacttgc tttgccagag      840
acaccaatgc ttcttggttt taatgctcct gctacatcag aaccgagctc attcgaattt      900
ccaccaccac ctacggatga agagttaaga cttgctttgc cagagacgcc aatgcttctt      960
ggttttaatg ctcctgctac atcggaaccg agctcgttcg aatttccacc gcctccaaca     1020
gaagatgaac tagaaatcat ccgggaaaca gcatcctcgc tagattctag ttttacaaga     1080
ggggatttag ctagtttgag aaatgctatt aatcgccata gtcaaaattt ctctgatttc     1140
ccaccaatcc caacagaaga agagttgaac gggagaggcg gtagaccaac atctgaagaa     1200
tttagttcgc tgaatagtgg tgattttaca gatgacgaaa acagcgagac aacagaagaa     1260
gaaattgatc gcctagctga tttaagagat agaggaacag aaaacactc aagaaatgcg      1320 ggtttttac cattaaatcc gtttgctagc agcccggttc cttcgttaag tccaaaggta     1380
tcgaaaataa gcgcaccggc tctgataagt gacataacta aaaaaacgcc atttaagaat     1440
ccatcacagc cattaaatgt gtttaataaa aaaactacaa cgaaaacagt gactaaaaaa     1500
ccaacccctg taaagaccgc accaaagcta gcagaacttc ctgccacaaa accacaagaa     1560
accgtactta gggaaaataa acacccttt atagaaaaac aagcagaaac aaacaagcag      1620
tcaattaata tgccgagcct accagtaatc caaaaagaag ctacagagag cgataaagag     1680
gaaatgaaac cacaaaccga ggaaaaatg gtagaggaaa gcgaatcagc taataacgca      1740
aacggaaaaa atcgttctgc tggcattgaa gaaggaaaac taattgctaa agtgcagaa      1800 gacgaaaaag cgaaggaaga accagggaac catacgacgt taattcttgc aatgttagct     1860
attggcgtgt tctctttagg ggcgtttatc aaaattattc aattaagaaa aataattaa      1920
```

<210> SEQ ID NO 44
<211> LENGTH: 529
<212> TYPE: PRT
<213> ORGANISM: Listeria monocytogenes

<400> SEQUENCE: 44

```
Met Lys Lys Ile Met Leu Val Phe Ile Thr Leu Ile Leu Val Ser Leu
  1               5                  10                  15

Pro Ile Ala Gln Gln Thr Glu Ala Lys Asp Ala Ser Ala Phe Asn Lys
             20                  25                  30

Glu Asn Ser Ile Ser Ser Met Ala Pro Pro Ala Ser Pro Pro Ala Ser
         35                  40                  45

Pro Lys Thr Pro Ile Glu Lys Lys His Ala Asp Glu Ile Asp Lys Tyr
     50                  55                  60

Ile Gln Gly Leu Asp Tyr Asn Lys Asn Asn Val Leu Val Tyr His Gly
 65                  70                  75                  80

Asp Ala Val Thr Asn Val Pro Pro Arg Lys Gly Tyr Lys Asp Gly Asn
                 85                  90                  95
```

-continued

```
Glu Tyr Ile Val Val Glu Lys Lys Lys Ser Ile Asn Gln Asn Asn
                100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
        130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Lys Asn Ala Thr Lys Ser
                165                 170                 175

Asn Val Asn Asn Ala Val Asn Thr Leu Val Glu Arg Trp Asn Glu Lys
        180                 185                 190

Tyr Ala Gln Ala Tyr Pro Asn Val Ser Ala Lys Ile Asp Tyr Asp Asp
        195                 200                 205

Glu Met Ala Tyr Ser Glu Ser Gln Leu Ile Ala Lys Phe Gly Thr Ala
        210                 215                 220

Phe Lys Ala Val Asn Asn Ser Leu Asn Val Asn Phe Gly Ala Ile Ser
225                 230                 235                 240

Glu Gly Lys Met Gln Glu Val Ile Ser Phe Lys Gln Ile Tyr Tyr
                245                 250                 255

Asn Val Asn Val Asn Glu Pro Thr Arg Pro Ser Arg Phe Phe Gly Lys
        260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
        290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
                340                 345                 350

Lys Asp Glu Val Gln Ile Ile Asp Gly Asn Leu Gly Asp Leu Arg Asp
        355                 360                 365

Ile Leu Lys Lys Gly Ala Thr Phe Asn Arg Glu Thr Pro Gly Val Pro
370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
                420                 425                 430

Ile Ser Trp Asp Glu Val Asn Tyr Asp Pro Glu Gly Asn Glu Ile Val
        435                 440                 445

Gln His Lys Asn Trp Ser Glu Asn Asn Lys Ser Lys Leu Ala His Phe
        450                 455                 460

Thr Ser Ser Ile Tyr Leu Pro Gly Asn Ala Arg Asn Ile Asn Val Tyr
465                 470                 475                 480

Ala Lys Glu Cys Thr Gly Leu Ala Trp Glu Trp Arg Thr Val Ile
                485                 490                 495

Asp Asp Arg Asn Leu Pro Leu Val Lys Asn Arg Asn Ile Ser Ile Trp
        500                 505                 510

Gly Thr Thr Leu Tyr Pro Lys Tyr Ser Asn Lys Val Asp Asn Pro Ile
```

-continued 515 520 525

Glu

<210> SEQ ID NO 45
<211> LENGTH: 1589
<212> TYPE: DNA
<213> ORGANISM: Listeria monocytogenes

<400> SEQUENCE: 45
atgaaaaaaa taatgctagt ttttattaca cttatattag ttagtctacc aattgcgcaa 60
caaactgaag caaaggatgc atctgcattc aataaagaaa attcaatttc atccatggca 120
ccaccagcat ctccgcctgc aagtcctaag acgccaatcg aaaagaaaca cgcggatgaa 180
atcgataagt atatacaagg attggattac aataaaaaca atgtattagt ataccacgga 240
gatgcagtga caaatgtgcc gccaagaaaa ggttacaaag atggaaatga atatattgtt 300
gtggagaaaa agaagaaatc catcaatcaa aataatgcag acattcaagt tgtgaatgca 360
atttcgagcc taacctatcc aggtgctctc gtaaaagcga attcggaatt agtagaaaat 420
caaccagatg ttctccctgt aaaacgtgat tcattaacac tcagcattga tttgccaggt 480
atgactaatc aagacaataa aatcgttgta aaaaatgcca ctaaatcaaa cgttaacaac 540
gcagtaaata cattagtgga aagatggaat gaaaaatatg ctcaagctta tccaaatgta 600
gtgcaaaaat tgattatgat gacgaaatgg cttacagtga atcacaatta attgcgaaat 660
ttggtacagc atttaaagct gtaaataata gcttgaatgt aaacttcggc gcaatcagtg 720
aagggaaaat gcaagaagaa gtcattagtt ttaaacaaat ttactataac gtgaatgtta 780
atgaacctac aagaccttcc agatttttcg gcaaagctgt tactaaagag cagttgcaag 840
cgcttggagt gaatgcagaa aatcctcctg catatatctc aagtgtggcg tatggccgtc 900
aagtttattt gaaattatca actaattccc atagtactaa agtaaaagct gcttttgatg 960
ctgccgtaag cggaaaatct gtctcaggtg atgtagaact aacaaatatc atcaaaaatt 1020
cttccttcaa agccgtaatt tacggaggtt ccgcaaaaga tgaagttcaa atcatcgacg 1080
gcaacctcgg agacttacgc gatattttga aaaaaggcgc tacttttaat cgagaaacac 1140
caggagttcc cattgcttat acaacaaact tcctaaaaga caatgaatta gctgttatta 1200
aaaacaactc agaatatatt gaaacaactt caaaagctta tacagatgga aaaattaaca 1260
tcgatcactc tggaggatac gttgctcaat tcaacatttc ttgggatgaa gtaaattatg 1320
atcctgaagg taacgaaatt gttcaacata aaaactggag cgaaaacaat aaaagcaagc 1380
tagctcattt cacatcgtcc atctatttgc caggtaacgc gagaaatatt aatgtttacg 1440
ctaaagaatg cactggttta gcttgggaat ggtggagaac ggtaattgat gaccggaact 1500
taccacttgt gaaaaataga aatatctcca tctggggcac cacgctttat ccgaaatata 1560
gtaataaagt agataatcca atcgaataa 1589

<210> SEQ ID NO 46
<211> LENGTH: 1893
<212> TYPE: DNA
<213> ORGANISM: Listeria monocytogenes

<400> SEQUENCE: 46
gtgaaagaaa agcacaaccc aagaaggaag tattgtttaa tctcaggttt agctattatt 60
tttagtttat ggataattat tggaaacggg gcgaaagtac aagcggagac tatcaccgtg 120
ccaacgccaa tcaagcaaat tttttcagat gatgcttttg cagaaacaat caaagacaat 180

```
ttaaagaaaa aaagtgtgac agatgcagtg acacaaaatg aattaaatag tatagatcaa    240
atcattgcga ataatagtga tattaaatcc gttcaaggaa ttcagtattt acccaatgtg    300
acaaagttat ttttaaacgg gaataaaacta acagatataa agcccttagc aaacttgaaa   360
aatttaggat ggcttttttt agacgaaaat aaagttaagg acctaagttc gctcaaggat    420
ttaaaaaaat taaaatcact ttctttggag cataatggta taagtgatat aaacggactt    480
gttcatttac cacagctgga aagtttgtat ttgggaaata ataaaataac ggatataacg    540
gttctttcac gtttaactaa actggatact ttgtctctcg aagataacca aattagtgat    600
attgtgccac ttgcaggttt aactaaattg cagaacctat atttaagtaa aaatcacata    660
agcgatttaa gagcattagc aggacttaaa aatctagatg ttttagaatt atttagccaa    720
gaatgtctta ataagcctat taatcatcaa tctaatttgg ttgttccgaa tacagtgaaa    780
aacactgatg ggtcgttagt gactccagaa ataataagtg atgatggcga ttatgaaaaa    840
cctaatgtta aatggcattt accagaattt acaaatgaag tgagttttat tttctatcag    900
ccagtcacta ttggaaaagc aaaagcaaga tttcatggga gagtaaccca accactgaaa    960
gaggtttaca cagtaagtta tgatgttgat ggaacggtaa taaaaacaaa agtagaagca   1020
gggacgcgga taactgcacc taaacctccg actaaacaag gctatgtttt taaaggatgg   1080
tatactgaaa aaaatggtgg gcatgagtgg aatttttaata cggattatat gtccggaaat   1140
gattttactt tgtacgcagt atttaaagcg gaaacgaccg aaaaagcagt caacttaacc   1200
cgctatgtca aatatattcg cgggaatgca ggcatctaca aacttccacg agaagataac   1260
tcgcttaaac aaggaactct agcctcgcac cgctgtaaag ctctaactgt tgatagagaa   1320
gcccgaaatg gcggaaaatt atggtacagg ttaaaaaata ttggctggac taaagcggaa   1380
aacctttcct tagaccgata cgataaaatg gaatatgaca aaggggttac cgcttatgca   1440
agagtgagaa atgcgtctgg aaattcggtt tggacaaaac cctacaacac agccggcgct   1500
aaacacgtga ataagctatc ggtctaccaa ggtaaaaata tgcgtatctt gcgcgaagcc   1560
aaaacaccaa ttactacatg gtatcaatt agcattggtg gtaaagtaat tggttgggtc   1620
gatacccgag cacttaacac attctacaaa caaagcatgg aaaagccaac ccgtttaact   1680
cgttatgtca gcgccaataa agctggcgaa tcgtactata aagtcccggt agcagataat   1740
ccagtcaaaa ggggtacttt agccaagtat aaaaatcaaa agttaattgt tgattgtcaa   1800
gcaaccatcg aaggtcaact ttggtaccga ataaggacta gttccacttt cattggttgg   1860
acgaaagcag ctaatttaag ggcacagaaa taa                                 1893
```